(12) United States Patent
Wooten

(10) Patent No.: US 7,491,501 B2
(45) Date of Patent: Feb. 17, 2009

(54) METHODS FOR IDENTIFYING MODULATORS OF INTRACELLULAR AGGREGATE FORMATION

(75) Inventor: Marie W. Wooten, Auburn, AL (US)

(73) Assignee: Auburn University, Auburn, AL (US)

(*) Notice: Subject to any disclaimer, the term of this patent is extended or adjusted under 35 U.S.C. 154(b) by 254 days.

(21) Appl. No.: 10/991,197

(22) Filed: Nov. 17, 2004

(65) Prior Publication Data

US 2005/0130896 A1 Jun. 16, 2005

Related U.S. Application Data

(60) Provisional application No. 60/520,835, filed on Nov. 17, 2003.

(51) Int. Cl.
*G01N 33/566* (2006.01)
*G01N 33/58* (2006.01)
*G01N 33/68* (2006.01)
*A61K 49/00* (2006.01)

(52) U.S. Cl. .................... 435/7.21; 435/7.8
(58) Field of Classification Search .................. None
See application file for complete search history.

(56) References Cited

U.S. PATENT DOCUMENTS

| 5,866,318 A * | 2/1999 | Rydel et al. ............... 435/4 |
| 6,232,066 B1 * | 5/2001 | Felder et al. ............... 435/6 |
| 6,291,645 B1 | 9/2001 | Shin et al. ............... 530/350 |
| 2004/0171085 A1 * | 9/2004 | Joazeiro ............... 435/7.2 |

OTHER PUBLICATIONS

Vadlamudi 1998. FEBS Letters 435:138-142.*
Ishida et al. 1996. Journal of Biological Chemistry 271:28745-28748.*
Rudinger, In "Peptide Hormones" (ed., J.A. Parsons) University Park Press, Baltimore, pp. 1-7 (1976).*
Geetha et al. 2003. Program No. 786.3 2003 Abstract Viewer/Itinerary Planner. Washington DC: Society for Neuroscience, 2003.*
Seibenhener 2004. Molecular and Cellular Biochemistry 24:8055-8068.*
Geetha et al., 2003, "The atypical protein kinase C-interacting protein p62 serves as an adaptor for TRAF6-mediated ubiquitination of the nerve growth factor receptor TrkA", poster presented at Nov. 12, 2003 at the Annual Meeting of the Society for Neuroscience.*
Johnston 1998. Journal of Cell Biology 143:1883-1898.*
Sanz et al. 2000. EMBO J. 1576-1586.*
Joung, et al.; 1996; Molecular Cloning of a Phosphotyrosine-Independent Ligand of the p56[lck] SH2 Domain; Proc. Natl. Acad. Sci. USA; 93:5991-5995.
International Search Report and Written Opinion for application PCT/US04/38454, dated May 9, 2008.

* cited by examiner

*Primary Examiner*—Daniel E. Kolker
(74) *Attorney, Agent, or Firm*—Thomas, Kayden, Horstemeyer & Risley, LLP

(57) ABSTRACT

Methods and compositions for modulating the formation of intracellular aggregates are provided, in particular TRAF6 mediated intracellular aggregate formation. Additionally, methods and compositions for identifying modulators of intracellular aggregate formation are provided, for example methods for identifying compositions that inhibit or reduce the formation of intracellular aggregate formation.

11 Claims, 30 Drawing Sheets

SEQUENCE LISTING

```
<160> NUMBER OF SEQ ID NOS: 9

<210> SEQ ID NO 1
<211> LENGTH: 440
<212> TYPE: PRT
<213> ORGANISM: homo sapiens
<220> FEATURE:
<221> NAME/KEY: misc
<222> LOCATION: (1)..(440)
<223> OTHER INFORMATION: p62

<400> SEQUENCE: 1

Met Ala Ser Leu Thr Val Lys Ala Tyr Leu Leu Gly Lys Glu Asp Ala
1               5                   10                  15

Ala Arg Glu Ile Arg Arg Phe Ser Phe Cys Cys Ser Pro Glu Pro Glu
            20                  25                  30

Ala Glu Ala Glu Ala Ala Ala Gly Pro Gly Pro Cys Glu Arg Leu Leu
        35                  40                  45

Ser Arg Val Ala Ala Leu Phe Pro Ala Leu Arg Pro Gly Gly Phe Gln
    50                  55                  60

Ala His Tyr Arg Asp Glu Asp Gly Asp Leu Val Ala Phe Ser Ser Asp
65                  70                  75                  80

Glu Glu Leu Thr Met Ala Met Ser Tyr Val Lys Asp Asp Ile Phe Arg
                85                  90                  95
```

```
Ile Tyr Ile Lys Glu Lys Lys Glu Cys Arg Arg Asp His Arg Pro Pro
            100                 105                 110
Cys Ala Gln Glu Ala Pro Arg Asn Met Val His Pro Asn Val Ile Cys
        115                 120                 125
Asp Gly Cys Asn Gly Pro Val Val Gly Thr Arg Tyr Lys Cys Ser Val
    130                 135                 140
Cys Pro Asp Tyr Asp Leu Cys Ser Val Cys Glu Gly Lys Gly Leu His
145                 150                 155                 160
Arg Gly His Thr Lys Leu Ala Phe Pro Ser Pro Phe Gly His Leu Ser
                165                 170                 175
Glu Gly Phe Ser His Ser Arg Trp Leu Arg Lys Val Lys His Gly His
            180                 185                 190
Phe Gly Trp Pro Gly Trp Glu Met Gly Pro Pro Gly Asn Trp Ser Pro
        195                 200                 205
Arg Pro Pro Arg Ala Gly Glu Ala Arg Pro Gly Pro Thr Ala Glu Ser
    210                 215                 220
Ala Ser Gly Pro Ser Glu Asp Pro Ser Val Asn Phe Leu Lys Asn Val
225                 230                 235                 240
Gly Glu Ser Val Ala Ala Ala Leu Ser Pro Leu Gly Ile Glu Val Asp
                245                 250                 255
Ile Asp Val Glu His Gly Gly Lys Arg Ser Arg Leu Thr Pro Val Ser
            260                 265                 270
Pro Glu Ser Ser Ser Thr Glu Glu Lys Ser Ser Gln Pro Ser Ser
        275                 280                 285
Cys Cys Ser Asp Pro Ser Lys Pro Gly Gly Asn Val Glu Gly Ala Thr
    290                 295                 300
Gln Ser Leu Ala Glu Gln Met Arg Lys Ile Ala Leu Glu Ser Glu Gly
305                 310                 315                 320
Arg Pro Glu Glu Gln Met Glu Ser Asp Asn Cys Ser Gly Gly Asp Asp
                325                 330                 335
Asp Trp Thr His Leu Ser Ser Lys Glu Val Asp Pro Ser Thr Gly Glu
            340                 345                 350
Leu Gln Ser Leu Gln Met Pro Glu Ser Glu Gly Pro Ser Ser Leu Asp
        355                 360                 365
Pro Ser Gln Glu Gly Pro Thr Gly Leu Lys Glu Ala Ala Leu Tyr Pro
    370                 375                 380
His Leu Pro Pro Glu Ala Asp Pro Arg Leu Ile Glu Ser Leu Ser Gln
385                 390                 395                 400
Met Leu Ser Met Gly Phe Ser Asp Glu Gly Gly Trp Leu Thr Arg Leu
                405                 410                 415
Leu Gln Thr Lys Asn Tyr Asp Ile Gly Ala Ala Leu Asp Thr Ile Gln
            420                 425                 430
Tyr Ser Lys His Pro Pro Leu
        435                 440
```

<210> SEQ ID NO 2
<211> LENGTH: 385
<212> TYPE: PRT
<213> ORGANISM: artificial
<220> FEATURE:
<223> OTHER INFORMATION: artificial sequence - p62 truncation

<400> SEQUENCE: 2

```
Met Ala Ser Leu Thr Val Lys Ala Tyr Leu Leu Gly Lys Glu Asp Ala
1               5                   10                  15
```

```
Ala Arg Glu Ile Arg Arg Phe Ser Phe Cys Cys Ser Pro Glu Pro Glu
            20                  25                  30

Ala Glu Ala Glu Ala Ala Gly Pro Gly Pro Cys Glu Arg Leu Leu
        35                  40                  45

Ser Arg Val Ala Ala Leu Phe Pro Ala Leu Arg Pro Gly Gly Phe Gln
    50                  55                  60

Ala His Tyr Arg Asp Glu Asp Gly Asp Leu Val Ala Phe Ser Ser Asp
65                  70                  75                  80

Glu Glu Leu Thr Met Ala Met Ser Tyr Val Lys Asp Asp Ile Phe Arg
                85                  90                  95

Ile Tyr Ile Lys Glu Lys Lys Glu Cys Arg Arg Asp His Arg Pro Pro
            100                 105                 110

Cys Ala Gln Glu Ala Pro Arg Asn Met Val His Pro Asn Val Ile Cys
            115                 120                 125

Asp Gly Cys Asn Gly Pro Val Val Gly Thr Arg Tyr Lys Cys Ser Val
130                 135                 140

Cys Pro Asp Tyr Asp Leu Cys Ser Val Cys Glu Gly Lys Gly Leu His
145                 150                 155                 160

Arg Gly His Thr Lys Leu Ala Phe Pro Ser Pro Phe Gly His Leu Ser
                165                 170                 175

Glu Gly Phe Ser His Ser Arg Trp Leu Arg Lys Val Lys His Gly His
                180                 185                 190

Phe Gly Trp Pro Gly Trp Glu Met Gly Pro Pro Gly Asn Trp Ser Pro
            195                 200                 205

Arg Pro Pro Arg Ala Gly Glu Ala Arg Pro Gly Pro Thr Ala Glu Ser
    210                 215                 220

Ala Ser Gly Pro Ser Glu Asp Pro Ser Val Asn Phe Leu Lys Asn Val
225                 230                 235                 240

Gly Glu Ser Val Ala Ala Ala Leu Ser Pro Leu Gly Ile Glu Val Asp
                245                 250                 255

Ile Asp Val Glu His Gly Gly Lys Arg Ser Arg Leu Thr Pro Val Ser
            260                 265                 270

Pro Glu Ser Ser Ser Thr Glu Glu Lys Ser Ser Ser Gln Pro Ser Ser
            275                 280                 285

Cys Cys Ser Asp Pro Ser Lys Pro Gly Gly Asn Val Glu Gly Ala Thr
290                 295                 300

Gln Ser Leu Ala Glu Gln Met Arg Lys Ile Ala Leu Glu Ser Glu Gly
305                 310                 315                 320

Arg Pro Glu Glu Gln Met Glu Ser Asp Asn Cys Ser Gly Gly Asp Asp
                325                 330                 335

Asp Trp Thr His Leu Ser Ser Lys Glu Val Asp Pro Ser Thr Gly Glu
            340                 345                 350

Leu Gln Ser Leu Gln Met Pro Glu Ser Glu Gly Pro Ser Ser Leu Asp
            355                 360                 365

Pro Ser Gln Glu Gly Pro Thr Gly Leu Lys Glu Ala Ala Leu Tyr Pro
    370                 375                 380

His
385

<210> SEQ ID NO 3
<211> LENGTH: 6
<212> TYPE: PRT
<213> ORGANISM: artificial
<220> FEATURE:
<223> OTHER INFORMATION: TRAF6 artificial binding site
```

```
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc
<222> LOCATION: (6)..(6)
<223> OTHER INFORMATION: X = C, N, Q, T, S or G.

<400> SEQUENCE: 3

Pro Xaa Glu Xaa Xaa Xaa
1               5

<210> SEQ ID NO 4
<211> LENGTH: 32
<212> TYPE: PRT
<213> ORGANISM: artificial
<220> FEATURE:
<223> OTHER INFORMATION: artificial sequence for cell permeable peptide

<400> SEQUENCE: 4

Ala Ala Val Ala Leu Leu Pro Ala Val Leu Leu Ala Leu Leu Ala Pro
1               5                   10                  15

Glu Ser Ala Ser Gly Pro Ser Glu Asp Pro Ser Val Asn Phe Leu Lys
            20                  25                  30

<210> SEQ ID NO 5
<211> LENGTH: 32
<212> TYPE: PRT
<213> ORGANISM: artificial
<220> FEATURE:
<223> OTHER INFORMATION: artificial sequence - control cell permeable
      peptide

<400> SEQUENCE: 5

Ala Ala Val Ala Leu Leu Pro Ala Val Leu Leu Ala Leu Leu Ala Pro
1               5                   10                  15

Glu Ser Ala Ser Gly Ala Ser Ala Asp Ala Ser Val Asn Phe Leu Lys
            20                  25                  30

<210> SEQ ID NO 6
<211> LENGTH: 16
<212> TYPE: PRT
<213> ORGANISM: artificial
<220> FEATURE:
<223> OTHER INFORMATION: TRAF6 inhibitory peptide

<400> SEQUENCE: 6

Glu Ser Ala Ser Gly Pro Ser Glu Asp Pro Ser Val Asn Phe Leu Lys
1               5                   10                  15

<210> SEQ ID NO 7
<211> LENGTH: 5
<212> TYPE: PRT
<213> ORGANISM: artificial
<220> FEATURE:
<223> OTHER INFORMATION: TRAF6 binding motif
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
```

```
<400> SEQUENCE: 7

Pro Xaa Glu Xaa Xaa
1               5

<210> SEQ ID NO 8
<211> LENGTH: 11
<212> TYPE: PRT
<213> ORGANISM: Human immunodeficiency virus

<400> SEQUENCE: 8

Tyr Gly Arg Lys Lys Arg Arg Gln Arg Arg
1               5                   10

<210> SEQ ID NO 9
<211> LENGTH: 9
<212> TYPE: PRT
<213> ORGANISM: artificial
<220> FEATURE:
<223> OTHER INFORMATION: protein transduction domain

<400> SEQUENCE: 9

Arg Lys Lys Arg Arg Gln Arg Arg Arg
1               5
```

METHODS FOR IDENTIFYING MODULATORS OF INTRACELLULAR AGGREGATE FORMATION

CROSS-REFERENCE TO RELATED APPLICATION

This application claims benefit of and priority to U.S. Provisional Patent Application No. 60/520,835 filed on Nov. 17, 2003, and where permissible, is incorporated by reference in its entirety.

STATEMENT RELATING TO FEDERALLY SPONSORED WORK OR DEVELOPMENT

Aspects of the disclosure were funded, in part, by Grant Nos. 5 R21 NS044847-02 and NS-33661 awarded by the National Institutes of Health. The US government may have certain rights in the claimed subject matter.

BACKGROUND

1. Technical Field

Aspects of the disclosed subject matter are generally related to methods and compositions for reducing or inhibiting aggregate formation, in particular intracellular aggregate formation mediated by p62.

2. Related Art

Neurodegeneration is a broad pathology of the nervous system and is found in diseases such as Alzheimer's disease (AD), Parkinson's disease, ALS, head trauma, epilepsy and stroke. As many as 4.5 million Americans are believed to suffer from AD alone. The specific cause of neurodegeneration in any particular disease or disorder often remains a mystery; however, research is beginning to reveal a common theme among neurodegenerative diseases. It appears that disorders of protein shape or protein accumulation may contribute to neurodegeneration. Indeed, many neurodegenerative diseases including AD are characterized by ubiquitin-positive proteinaceous aggregates or inclusion bodies.

Although neurodegenerative diseases affect a large number of individuals, there are few therapies available to treat or prevent these disorders. Some existing therapies include, for example, the transplantation of stem cells into areas of the brain. The heterologous transplantation of stem cells obtained from a source other than the patient presents both ethical and practical problems. The transplantation of embryonic stem cells is ethically controversial because the stem cells are obtained from embryos. Moreover, it is unclear whether such transplanted cells can survive in the patient over the long term and successfully ameliorate or prevent neurodegeneration. With the discovery of neural stem cells or adult stem cells, the possibility of autogolous transplantation has become possible. However, these neural or adult stem cells must be located, successfully cultivated, and induced to differentiate into the needed cells or tissue.

Other therapies include the use of small molecules. One small molecule therapy includes the administration of dopamine to treat patients suffering with Parkinson's Disease; however, dopamine treats symptoms of Parkinson's Disease, for example tremors. Dopamine does not appear to treat the underlying cause of Parkinson's Disease, nor does it appear to prevent the progression of the disease. In addition, the therapeutic effects of dopamine begin to wear-off in increasingly shorter times the longer a patient has been on the drug.

Thus, there is a need for methods and compositions for treating neurological pathologies and for identifying additional compositions for the treatment of neurological pathologies.

SUMMARY

Methods and compositions for modulating the formation of intracellular aggregates are provided. Additionally, methods and compositions for identifying modulators of intracellular aggregate formation are provided, for example methods for identifying compositions that inhibit or reduce the formation of intracellular aggregate formation.

One aspect, among others, provides a pharmaceutical composition comprising a p62 modulator, a TRAF6 modulator, an E3 ligase modulator, a prodrug, a pharmaceutically acceptable salt, or combinations thereof in an amount sufficient to interfere with TRAF6 oligomerization. One particular aspect provides a pharmaceutical composition comprising an active ingredient that interferes or inhibits the interaction or oligomerization of TRAF6 with p62 and thereby prevents or reduces intracellular aggregate formation.

Another aspect provides a method for identifying a modulator of intracellular aggregate formation by determining oligomerization of TRAF6 or fragment thereof in the presence of a test compound, and selecting the test compound that reduces or inhibits TRAF6 oligomerization and optionally inhibits or reduces intracellular aggregate formation.

Yet another aspect provides a method for treating a neurological pathology by administering to a host an effective or therapeutic amount of a p62 modulator, a TRAF6 modulator, an E3 ligase modulator, a prodrug, a pharmaceutically acceptable salt, or combinations thereof, wherein the modulator interferes with the interaction between TRAF6 and another polypeptide, for example p62, and optionally reduces or inhibits the formation of intracellular aggregates.

Other compositions, methods, features, and advantages of the present disclosure will be or become apparent to one with skill in the art upon examination of the following drawings and detailed description. It is intended that all such additional compositions, methods, features, and advantages be included within this description, be within the scope of the present disclosure, and be protected by the accompanying claims.

DETAILED DESCRIPTION

Figure 1A:
FIG. 1A shows a diagram of p62 constructs including myc-tagged wild-type (WT) p62; full-length p62 (amino acids 1 to 440); p62ΔN-term, a construct missing amino acids 1 to 229; and p62ΔUBA, a construct missing the UBA domain (amino acids 386 to 440).

It has been discovered that the N terminus of p62 targets its interaction with the proteasome, and the C-terminal UBA domain (amino acids 386 to 440) interacts with K63-polyubiquitinated substrates p62 acts as a shuttling factor for delivery of polyubiquitinated substrates to the proteasome for degradation. Modulating the interaction of p62 with K63-polyubiquitinated substrates directly or indirectly through TRAF6 has been discovered to inhibit or reduce the formation of insoluble polypeptide aggregates in cells. Compositions and methods for modulating p62 function either directly or indirectly are provided. Methods for identifying other modulators of p62 function are also provided.

The present disclosure may be understood more readily by reference to the following detailed description and the Examples included therein. Before the present compounds, compositions and methods are disclosed and described, it is to be understood that this disclosure is not limited to specific pharmaceutical carriers, or to particular pharmaceutical formulations or administration regimens, as such may, of course, vary. It is also to be understood that the terminology used herein is for the purpose of describing particular embodiments only and is not intended to be limiting.

The term "aggregate" or "inclusion" refers to a combination of substances in a cell having decreased solubility compared to the individual components of the aggregate. Representative aggregates comprise two or more polypeptides. The polypeptides can be the same or different. Generally, the aggregate is an insoluble conglomeration of one or more polypeptides. Exemplary polypeptide components include, but are not limited to, p62, ubiquitin, tau, TRAF6, fragments thereof, or a combination thereof.

The term "organism" or "host" refers to any living entity comprised of at least one cell. A living organism can be as simple as, for example, a single eukaryotic cell or as complex as a mammal, including a human being. "Pharmaceutically acceptable salt" refers to those salts which retain the biological effectiveness and properties of the free bases and which are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like.

A "pharmaceutical composition" refers to a mixture of one or more of the compounds described herein, or pharmaceutically acceptable salts thereof, with other chemical components, such as physiologically acceptable carriers and excipients. The purpose of a pharmaceutical composition is to facilitate administration of a compound to an organism.

As used herein, a "pharmaceutically acceptable carrier" refers to a carrier or diluent that does not cause significant irritation to an organism and does not abrogate the biological activity and properties of the administered compound.

An "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

The term "prodrug" refers to an agent, including nucleic acids and proteins, which is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Harper, N.J. (1962). Drug Latentiation in Jucker, ed. Progress in Drug Research, 4:221-294; Morozowich et al. (1977). Application of Physical Organic Principles to Prodrug Design in E. B. Roche ed. Design of Biopharmaceutical Properties through Prodrugs and Analogs, APhA; Acad. Pharm. Sci.; E. B. Roche, ed. (1977). Bioreversible Carriers in Drug in Drug Design, Theory and Application, APhA; H. Bundgaard, ed. (1985) Design of Prodrugs, Elsevier; Wang et al. (1999) Prodrug approaches to the improved delivery of peptide drug, Curr. Pharm. Design. 5(4):265-287; Pauletti et al. (1997). Improvement in peptide bioavailability: Peptidomimetics and Prodrug Strategies, Adv. Drug. Delivery Rev. 27:235-256; Mizen et al. (1998). The Use of Esters as Prodrugs for Oral Delivery of β-Lactam antibiotics, Pharm. Biotech. 11,: 345-365; Gaignault et al. (1996). Designing Prodrugs and Bioprecursors I. Carrier Prodrugs, Pract. Med. Chem. 671-696; M. Asgharnejad (2000). Improving Oral Drug Transport Via Prodrugs, in G. L. Amidon, P. I. Lee and E. M. Topp, Eds., Transport Processes in Pharmaceutical Systems, Marcell Dekker, p. 185-218; Balant et al. (1990) Prodrugs for the improvement of drug absorption via different routes of administration, Eur. J. Drug Metab. Pharmacokinet., 15(2): 143-53; Balimane and Sinko (1999). Involvement of multiple transporters in the oral absorption of nucleoside analogues, Adv. Drug Delivery Rev., 39(1-3):183-209; Browne (1997). Fosphenytoin (Cerebyx), Clin. Neuropharmacol. 20(1): 1-12; Bundgaard (1979). Bioreversible derivatization of drugs—principle and applicability to improve the therapeutic effects of drugs, Arch. Pharm. Chemi. 86(1): 1-39; H. Bundgaard, ed. (1985) Design of Prodrugs, New York: Elsevier; Fleisher et al. (1996). Improved oral drug delivery: solubility limitations overcome by the use of prodrugs, Adv. Drug Delivery Rev. 19(2): 115-130; Fleisher et al. (1985). Design of prodrugs for improved gastrointestinal absorption by intestinal enzyme targeting, Methods Enzymol. 112: 360-81; Farquhar D, et al. (1983). Biologically Reversible Phosphate-Protective Groups, J. Pharm. Sci., 72(3): 324-325; Han, H. K. et al. (2000). Targeted prodrug design to optimize drug delivery, AAPS PharmSci., 2(1): E6; Sadzuka Y. (2000). Effective prodrug liposome and conversion to active metabolite, Curr Drug Metab., 1(1):31-48; D. M. Lambert (2000) Rationale and applications of lipids as prodrug carriers, Eur. J. Pharm. Sci., 11 Suppl 2:S15-27; Wang, W. et al. (1999) Prodrug approaches to the improved delivery of peptide drugs. Curr. Pharm. Des., 5(4):265-87.

The term "nucleic acid" is a term of art that refers to a string of at least two base-sugar-phosphate combinations. For naked DNA delivery, a polynucleotide contains more than 120 monomeric units since it must be distinguished from an oligonucleotide. However, for purposes of delivering RNA, RNAi and siRNA, either single or double stranded, a polynucleotide contains 2 or more monomeric units. Nucleotides are the monomeric units of nucleic acid polymers. The term includes deoxyribonucleic acid (DNA) and ribonucleic acid (RNA). RNA may be in the form of a tRNA (transfer RNA), snRNA (small nuclear RNA), rRNA (ribosomal RNA), mRNA (messenger RNA), anti-sense RNA, RNAi, siRNA, and ribozymes. The term also includes PNAs (peptide nucleic acids), phosphorothioates, and other variants of the phosphate backbone of native nucleic acids. Anti-sense is a polynucleotide that interferes with the function of DNA and/or RNA. Natural nucleic acids have a phosphate backbone, artificial nucleic acids may contain other types of backbones, but contain the same bases.

The term "polypeptides" includes proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gin, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of the disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamnine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within +1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gin, His), (Asp: Glu, Cys, Ser), (Gin: Asn), (Glu: Asp), (Gly: Ala), (His: Asn, Gin), (lie: Leu, Val), (Leu: lie, Val), (Lys: Arg), (Met: Leu, Tyr), (Ser: Thr), (Thr: Ser), (Tip: Tyr), (Tyr: Trp, Phe), and (Val: lie, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

"Identity," as known in the art, is a relationship between two or more polypeptide sequences, as determined by comparing the sequences. In the art, "identity" also means the degree of sequence relatedness between polypeptide as determined by the match between strings of such sequences. "Identity" and "similarity" can be readily calculated by known methods, including, but not limited to, those described in (Lesk, A. M., Ed. (1988) Computational Molecular Biology, Oxford University Press, New York; Smith, D. W., Ed. (1993) Biocomputing: Infomatics and Genome Projects. Academic Press, New York; Griffin, A. M., and Griffin, H. G., Eds. (1994) Computer Analysis of Sequence Data: Part I, Humana Press, New Jersey; von Heinje, G. (1987) Sequence Analysis in Molecular Biology, Academic Press; Gribskov, M. and Devereux, J., Eds. (1991) Sequence Analysis Primer. M Stockton Press, New York; Carillo, H. and Lipman, D. (1988) SIAM J Applied Math., 48, 1073).

Preferred methods to determine identity are designed to give the largest match between the sequences tested. Methods to determine identity and similarity are codified in publicly available computer programs. The percent identity between two sequences can be determined by using analysis software (i.e., Sequence Analysis Software Package of the Genetics Computer Group, Madison Wis.) that incorporates the Needelman and Wunsch, ((1970) J. Mol. Biol., 48, 443-453) algorithm (e.g., NBLAST, and XBLAST).

By way of example, a polypeptide sequence may be identical to the reference sequence, that is be 100% identical, or it may include up to a certain integer number of amino acid alterations as compared to the reference sequence such that the % identity is less than 100%. Such alterations are selected from: at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

As used herein, the term "purified" and like terms relate to the isolation of a molecule or compound in a form that is substantially free (at least 60% free, preferably 75% free, and most preferably 90% free) from other components normally associated with the molecule or compound in a native environment.

As used herein, the term "treating" includes alleviating the symptoms associated with a specific disorder or condition and/or preventing or eliminating said symptoms.

"Operably linked" refers to a juxtaposition wherein the components are configured so as to perform their usual function. For example, control sequences or promoters operably linked to a coding sequence are capable of effecting the expression of the coding sequence, and an organelle localization sequence operably linked to the protein will direct the linked protein to be localized at the specific organelle.

As used herein, the term "exogenous DNA" or "exogenous nucleic acid sequence" or "exogenous polynucleotide" refers to a nucleic acid sequence that was introduced into a cell or organelle from an external source. Typically the introduced exogenous sequence is a recombinant sequence.

As used herein, the term "transfection" refers to the introduction of a nucleic acid sequence into the interior of a membrane enclosed space of a living cell, including introduction of the nucleic acid sequence into the cytosol of a cell as well as the interior space of a mitochondria, nucleus or chloroplast. The nucleic acid may be in the form of naked DNA or RNA, associated with various proteins or the nucleic acid may be incorporated into a vector.

As used herein, the term "vector" is used in reference to a vehicle used to introduce a nucleic acid sequence into a cell. A viral vector is virus that has been modified to allow recombinant DNA sequences to be introduced into host cells or cell organelles.

The term "heterologous" means derived from a separate genetic source, a separate organism, or a separate species. Thus, a heterologous antigen is an antigen from a first genetic source expressed by a second genetic source. The second genetic source is typically a vector.

The term "recombinant" generally refers to a non-naturally occurring nucleic acid, nucleic acid construct, or polypeptide. Such non-naturally occurring nucleic acids include combinations of DNA molecules of different origin that are joined using molecular biology technologies, or natural nucleic acids that have been modified, for example that have deletions, substitutions, inversions, insertions, etc. Recombinant also refers to the polypeptide encoded by the recombinant nucleic acid. Non-naturally occurring nucleic acids or polypeptides include nucleic acids and polypeptides modified by man.

Having defined some of the terms herein, the various embodiments of the disclosure will be described.

Sequestosome 1/p62

One embodiment of the present disclosure provides compositions and methods for modulating, disrupting, interfering, increasing, or inhibiting sequestosome 1/p62 (also referred to as p62) function or availability either directly or indirectly. p62 is a cellular protein which was initially identified as a phosphotyrosine independent ligand of the src homology 2 (SH2) domain of $p56^{lck}$. The protein was cloned by two independent groups as a counteracting protein of the atypical PKC, zeta, and is also named ZIP: zeta PKC interacting protein. p62 was shown to bind ubiquitin noncovalently and sequester into cytoplasmic aggregates. At its C-terminus p62 possesses a ubiquitin associating domain (UBA), amino acids 386-434, that binds polyubiquitin chains. In addition, p62 possesses several other structural motifs. At its N-terminus p62 possesses an acidic interaction domain (AID/PB1) that binds the atypical protein kinase C zeta, followed by a binding site for the RING finger protein TRAF6, and two PEST sequences. The N-terminal PB1 motif of p62 shares considerable structural homology with the Ub1 motif that binds to the proteasome.

The data provided in this disclosure show that p62 can be characterized as a polyubiquitin shuttling factor, interacting with ubiquitinated substrates through its UBA domain and the proteasome through its N-terminal PB1 domain. Aggregates of polyubiquitin may accumulate in the cytoplasm over time if proteins involved in the shuttling of polyubiquitinated substrates, such as p62, fail to target proteins for degradation.

Accumulation of polyubiquitinated proteins into insoluble aggregates is a hallmark of many neurodegenerative diseases. The molecular mechanism by which these aggregates form is poorly understood. However, disturbances in the ubiquitin proteasome pathway have been linked as an underlying factor in the pathogenesis of several diseases.

Accordingly, another embodiment provides a pharmaceutical composition comprising a p62 modulator, a prodrug, or pharmaceutically acceptable salt thereof in an amount sufficient to interfere with TRAF6 interaction with p62 and thereby prevent or reduce intracellular aggregate formation. The pharmaceutical composition can be used to treat disorders or symptoms arising at least in part from the formation of intracellular aggregates, in particular p62-mediated aggregate formation. Exemplary disorders or diseases include, but are not limited to, Alzheimer's Disease, Paget's Disease, Huntington's Disease, Parkinson's Disease or ALS. In some embodiments, the pharmaceutical composition prevents or reduces the formation of intracellular aggregates comprising K63 polyubiquitinated substrates. Exemplary K63 polyubiquitinated substrates include, but are not limited to, polypeptides such as tau. It will be appreciated that any polypeptide modified with ubiquitin via a K63 linkage is within the scope of the present disclosure.

Ubiquitin is a small polypeptide of 76 amino acids that can be covalently attached to other proteins, and p62 has been shown to interact in a noncovalent fashion with polyubiquitin chains. Conjugation of ubiquitin to substrate proteins requires three enzymes: a ubiquitin-activating enzyme (E1), a ubiquitin-conjugating enzyme (E2), and a ubiquitin ligase (E3). Initially, E1 activates ubiquitin by forming a high-energy thioester intermediate with the C-terminal glycine using ATP. The activated ubiquitin is sequentially transferred to E2 and then to E3 which catalyzes isopeptide bond formation between the activated C-terminal glycine of ubiquitin and an $\epsilon$-amino group of a lysine residue in the substrate. However, only HECT-type E3s can form thioester bonds with ubiquitin. While RING E3s such as TRAF6 do not. Consequently, the isopeptide bond that is formed between ubiquitin and the substrate could be formed by either E2 or E3. Following the linkage of the first ubiquitin, additional molecules of ubiquitin are attached to the previously conjugated moiety to form branched polyubiquitin chains employing lysine (K) linkage K29, K48, or K63. It has been proposed that the fate of a substrate may depend on the length of the chain as well as the lysine linkage (K29, K48, or K63) involved In forming the chain. Proteins which possess K48 chains target proteins to the proteasome, whereas ubiquitin chains composed of K63 have been shown to possess a role aside from that of proteasomal targeting. Ubiquitin itself can be modified at all seven lysine residues, suggesting that chains of K6, K11, K27, and K33, as well as those of K29, K48, and K63, may be found in vivo, thereby enhancing the diversity of polyubiquitin chains.

Another embodiment provides methods and compositions for modulating the the formation and/or degradation of K63 polyubiquitinated substrates. Compositions that modulate the attachment of ubitiquitin to a substrate, for example, a polypeptide, at the K63 position of ubiquitin can be identified and selected using the disclosed methods and compositions. In one embodiment, compounds that modulate the activity or availability of E3 ligases can be identified and selected. An exemplary E3 ligase includes, but is not limited to, TRAF6. An exemplary TRAF6 modulator includes, but is not limited to, a polypeptide TRAF6 inhibitor according to (SEQ ID NO. 1 or 2).

Modulators of TRAF6 activity or availability can interact with TRAF6 either directly or indirectly. For example, a polypeptide modulator can bind to TRAF6 or otherwise interact with TRAF6. In one embodiment, the TRAF6 modulator comprises a polypeptide that interacts with TRAF6 and modulates, for example inhibits, the E3 ligase activity of TRAF6. Compositions disclosed herein or identified using the disclosed methods can modulate the activity or bioavailability of TRAF6 and/or p62 by modulating the ability of TRAF6 and/or p62 to form complexes with other molecules or proteins. Modulating the ability of p62 or TRAF6 to form oligomers with other substances including, but not limited to polypeptides can reduce or prevent the formation of intracellular aggregates.

In a particular embodiment, the p62 inhibitor comprises a TRAF6 inhibitor. The TRAF6 inhibitor can bind to TRAF6 and prevent or interfere with the interaction of p62 with TRAF6. An exemplary TRAF6 inhibitor includes, but is not limited to, polypeptides, small molecules, antisense nucleic acids, enzymatic nucleic acids, antibodies, and the like. Representative peptides that inhibit TRAF6, for example, by binding to TRAF6, include, but are not limited to, a peptide comprising or consisting of amino acid sequence P-X-E-X-X-X' (SEQ ID NO. 3), wherein X is any amino acid and X' is selected from the group consisting of C, N, Q, T, S or G.

The inhibitory peptide can optionally include a protein transduction domain (PDT). PDTs are known in the art and include HIV-TAT, poly-arginine sequences, and the like. "Protein Transduction Domain" or PTD refers to a polypeptide, polynucleotide, carbohydrate, or organic or inorganic compounds that facilitates traversing a lipid bilayer, micelle, cell membrane, organelle membrane, or vesicle membrane. A PTD attached to another molecule facilitates the molecule traversing membranes, for example going from extracellular space to intracellular space, or cytosol to within an organelle. Exemplary PTDs include, but are not limited to, HIV TAT YGRKKRRQRRR (SEQ ID NO. 8) or RKKRRQRRR (SEQ ID NO. 9); 11 Arginine residues, or positively charged polypeptides or polynucleotides having 8-15 residues, preferably 9-11 residues and Kaposi fibroblast growth factor signal peptide.

It has also been discovered that p62 colocalizes to ubiquitin/tau-containing aggregates in hippocampus and cortex in patients with Alzheimer's disease (AD), but is sparse or absent from normal age-matched brain free from tangles. The appearance of p62 in AD brain is particularly intriguing since p62 accumulates in neurofibrillary tangles and colocalizes with hyperphosphorylated tau. Furthermore, the activity of the proteasome is decreased during the course of AD, while the neurotoxic amyloid beta peptide ($A\beta_{1-42}$) has been shown to bind the proteasome and block its activity as well. Thus, multiple factors may contribute to aggregate formation in AD brain. Therefore, the presence of p62 within neurofibrillary tangles (NFTs) raises the possibility that p62's ability to shuttle polyubiquitinated tau contributes to formation of tau aggregates and may play a contributing factor to the pathogenesis of AD.

Accordingly, another embodiment provides a method for treating a neurological pathology comprising administering to a host an effective or therapeutic amount of a p62 modulator, wherein the p62 modulator interferes with the interaction between TRAF6 and p62 and reduces or inhibits the formation of intracellular aggregates. The host can be any host suffering from a neuropathology. Typically, the host is a mammal, for example a human. Exemplary neuropathologies that can be treated, include but are not limited to Alzheimer's Disease, Huntington's Disease, Parkinson's Disease, and ALS.

In a particular embodiment, the p62 modulator comprises a TRAF6 inhibitor, for example a peptide inhibitor or a small molecule inhibitor. Small molecule inhibitors refer to organic compounds having at least one carbon atom that can bind to TRAF6, a substrate of TRAF6, p62, or both and inhibit or reduce the function of p62 by interfering with the interaction of TRAF6 with p62. A representative peptide inhibitor includes, but is not limited to, a peptide having an amino acid sequence P-X-E-X-X (SEQ ID NO. 7), wherein X is any amino acid or amino acid sequence P-X-E-X-X-X' (SEQ ID NO. 3), wherein X is any amino acid and X' is selected from the group consisting of C, N, Q, T, S or G.

Preventing or reducing protein aggregation by inhibition of E3 ubiquitin ligase activity can be an effective therapy for the treatment of neuropathologies in which aggregates are formed. Impairment of the proteasome by either the neurotoxic Aβ peptide or pharmacological inhibitors results in accumulation of tau-Ub within insoluble aggregates that compromise cell survival. In one embodiment, inhibition of TRAF6-p62 interaction blocks neurbtrophin-induced tau polyubiquitination, prevents aggregate formation, and thereby enhances cell survival.

Another embodiment provides a method for treating proteasome dysfunction comprising contacting a cell having a dysfunctional proteasome with a p62 modulator, wherein the p62 modulator disrupts interaction between p62 and TRAF6 and reduces intracellular aggregate formation. Proteasome dysfunction refers to a reduced ability or inability of the proteasome to degrade proteins.

Screening

The disclosure also provides methods for identifying p62 modulators and/or modulators of TRAF6 oligomerization. As used herein the term "test compound" or "modulator" refers to any molecule that may potentially inhibit or enhance p62 activity, for example p62 mediated aggregate formation and or TRAF6 oligomerization. Representative modulators inhibit or reduce activity or expression of p62 or TRAF6, inhibit the activity of TRAF6, p62, or a combination thereof, or interfere with the interaction of TRAF6 with p62. The test compound or modulator can be a protein or fragment thereof, a small molecule, or even a nucleic acid molecule. Some test compounds and modulators can be compounds that are structurally related to p62 or TRAF6 polypeptides. Using lead compounds to help develop improved compounds is known as "rational drug design" and includes not only comparisons with known inhibitors and activators, but predictions relating to the structure of target molecules.

One embodiment provides a method for identifying modulators of p62 mediate aggregate formation including assaying binding of p62 polypeptide, a homologue, or fragment thereof to TRAF6 or K63-polyubiquitinated substrates, and selecting the test compound that promotes or interferes with p62 mediated aggregate formation compared to a control compound.

Another embodiment provides a method for identifying modulators of p62 mediated aggregate formation comprising assaying binding of p62 polypeptide, a homologue, or fragment thereof to TRAF6, K63 polyubiquitinated substrates, a combination thereof, or fragments thereof in the presence of a test compound, and selecting the test compound that promotes or interferes with p62 interaction with TRAF6, K63 polyubiquitinated substrates, or combinations thereof and optionally promotes or interferes with p62 aggregate formation or p62 aggregate dissolution.

Still another embodiment provides a method for identifying modulators of TRAF6 oligomerization comprising assaying binding of TRAF6, a homologue, or fragment thereof to polypeptides or fragments thereof in the presence of a test compound, and selecting the test compound that promotes or interferes with TRAF6 interaction with the polypeptides.

Such compounds can be screened further for the ability to prevent or reduce intracellular aggregate formation with the disclosed methods. The identified compounds can modulate the formation of oligomers comprising TRAF6 and one or more polypeptides.

In another embodiment, small molecule libraries that are believed to meet the basic criteria for useful drugs can be screened to identify useful compounds. Screening of such libraries, including combinatorially generated libraries (e.g., expression libraries), is a rapid and efficient way to screen large numbers of related (and unrelated) compounds for activity. Combinatorial approaches also lend themselves to rapid evolution of potential drugs by the creation of second, third and fourth generation compounds modeled of active, but otherwise undesirable compounds.

Test compounds may include fragments or parts of naturally-occurring compounds, or may be found as active combinations of known compounds, which are otherwise inactive. Compounds isolated from natural sources, such as animals, bacteria, fungi, plant sources, including leaves and bark, and marine samples can be assayed as candidates for the presence of potentially useful pharmaceutical agents. It will be understood that the pharmaceutical agents to be screened could also be derived or synthesized from chemical compositions or man-made compounds. Thus, it is understood that the test compound identified by embodiments of the present disclosure may be peptide, polypeptide, polynucleotide, small molecule inhibitors, small molecule inducers, organic or inorganic, or any other compounds that may be designed based on known inhibitors or stimulators.

Other suitable modulators include antisense molecules, catalytic nucleic acids such as ribozymes, and antibodies (including single chain antibodies), each of which would be specific for p62, TRAF6 or both. For example, an antisense molecule that binds to a translational or transcriptional start site, or splice junctions, are within the scope of a test compound.

In addition to the modulating compounds initially identified, other sterically similar compounds may be formulated to mimic the key portions of the structure of the modulators, for example TRAF6 interaction domains. Such compounds, which may include peptidomimetics of peptide modulators, may be used in the same manner as the initial modulators.

An inhibitor or activator according to the present disclosure may be one which exerts its inhibitory or activating effect upstream, downstream, directly, or indirectly on p62 mediated aggregate formation or dissolution. In one embodiment, the inhibition or activation by an identified modulator results in the modulation of p62 or TRAF6 biological activity or expression as compared to that observed in the absence of the added test compound.

Screening for Modulators of p62 Activity

Embodiments of the present disclosure include methods for identifying modulators of the function, expression, or bioavailability of p62 and/or TRAF6, in particular the function of p62 and/or TRAF6 in p62 mediated aggregate formation. Direct modulation refers to a physical interaction between the modulator and p62, TRAF6, or binding sites thereof, for example binding of the modulator to a region of p62 or TRAF6. Indirect modulation of p62 mediated aggregate formation can be accomplished when the modulator physically associates with a cofactor, second protein or second biological molecule that interacts with p62 or TRAF6 or a polyubiquitinated substrate either directly or indirectly. Additionally, indirect modulation would include modulators that affect the expression or the translation of RNA encoding p62 or TRAF6.

In some embodiments, the assays can include random screening of large libraries of test compounds. Alternatively, the assays may be used to focus on particular classes of compounds suspected of modulating the function or expression of p62 or TRAF6 as a result of the classes of compounds containing a specific structure or motif.

Assays can include determinations of p62 or TRAF6 expression, protein expression, protein activity, p62-TRAF6 interaction, or binding activity. Other assays can include determinations of nucleic acid transcription or translation, for example mRNA levels, mRNA stability, mRNA degradation, transcription rates, and translation rates.

In one embodiment, the identification of a p62 mediated aggregate formation modulator is based on the function of p62 and/or TRAF6 in the presence and absence of a test compound. The test compound or modulator can be any substance that alters or is believed to alter the function of p62, in particular the interaction of p62, TRAF6 and K63 polyubiquitinated substrates. Typically, a modulator will be selected that reduces, eliminates, or mitigates p62 mediated aggregate formation.

One exemplary method includes contacting p62 or TRAF6 with at least a first test compound, and assaying for an interaction between p62 or TRAF6 and the first test compound with an assay. The assaying can include determining p62 mediated aggregate formation.

Specific assay endpoints or interactions that may be measured in the disclosed embodiments include, but are not limited to, assaying for aggregate formation, p62 or TRAF6 down regulation or turnover. These assay endpoints may be assayed using standard methods such as FACS, FACE, ELISA, Northern blotting and/or Western blotting. Moreover, the assays can be conducted in cell free systems, in isolated cells, genetically engineered cells, immortalized cells, or in organisms including transgenic animals.

Other screening methods include using labeled p62 or TRAF6 to identify a test compound. p62 or TRAF6 can be labeled using standard labeling procedures that are well known and used in the art. Such labels include, but are not limited to, radioactive, fluorescent, biological and enzymatic tags.

Another embodiment provides a method for identifying a modulator of p62 or TRAF6 expression by determining the effect a test compound has on the expression of p62 or TRAF6 in neural cells. For example neural cells expressing p62 or TRAF6 can be contacted with a test compound. p62 or TRAF6 expression can be determined by detecting p62 or TRAF6 protein expression or p62 or TRAF6 mRNA transcription or translation. Suitable cells for this assay include, but are not limited to, immortalized cell lines, primary cell culture, or cells engineered to express p62 or TRAF6 or variants thereof. Compounds that modulate the expression of p62 or TRAF6, in particular that decrease the expression or bioavailability of p62 or TRAF6, can be selected. Compounds that modulate the expression of p62 or TRAF6, in particular that increase the expression or bioavailability of p62 or TRAF6, can also be selected.

Phage Display

One embodiment for identifying modulators of p62 or TRAF6 includes using phage display technology to identify polypeptides that specifically bind to p62 or TRAF6 and do not substantially bind to other polypeptides. Phage technology uses bacteriophages, viruses that contain single stranded DNA within a protein cylinder. Within the genome of the bacteriophage (pIII or pVIII regions usually), DNA sequences that encode for various peptides can be inserted. These inserted sequences encode for peptides that are displayed on the capsid (or outer cylinder) of the bacteriophage. Thus, bacteriophage libraries contain bacteriophages of great diversity in their ligand structure. Depending on the length and complexity of the peptide attached to the bacteriophage, libraries can contain billions of different peptide structures and thus billions of unique bacteriophages.

Phage display technology can be used to find a masking ligand against p62 or TRAF6 or p62 or TRAF6 binding sites. Generally, the method starts by fixing p62 or TRAF6 to a substrate, for example sepharose beads that have terminal amino groups can be used. With a common crosslinking strategy, the amine structure on the beads will attach to a carboxyl group on p62 or TRAF6.

After it is verified that p62 or TRAF6 is attached to the sepharose beads through the use of a sulfate group assay, phage libraries will be mixed with the beads. Those bacteriophage that possess ligands with an affinity for p62 or TRAF6 will bind to the p62 or TRAF6/sepharose bead complex. Those that do not will be washed away. The phage that are bound to the bead complex are then eluted using various buffers.

Once eluted, phage with affinity for p62 or TRAF6 will then be introduced to a K91 bacteria strain. The viruses will then infect these bacteria and insert their DNA into the host's DNA, thereby using the bacteria to make more bacteriophage. The amplified bacteriophage contain populations that are more concentrated with ligands of higher affinity for SE p62 or TRAF6. The phage can be harvested from the bacteria cultures and then passed again through a p62 or TRAF6/sepharose bead complex for further purification. Typically, there are three purification steps (where phage will be introduced to beads with p62 or TRAF6 and phage will be amplified using bacteria hosts).

After purification of phage, the ligands on these purified species can be sequenced using an independent laboratory. Once sequenced, affinity of these ligands will be verified using a p62 or TRAF6-ligand assay.

Once it is established that the ligand binds to p62 or TRAF6, the ligand can be tested using cell culture techniques. Cells expressing p62 and TRAF6 can be plated on culture plates, and a test compound can be introduced to such plates with or without application of the ligand with affinity to p62 or TRAF6. If the ligand masks p62 or TRAF6 intracellularly, reduced p62-mediated aggregate formation should be detected.

In Vitro Assays

Another embodiment provides for in vitro assays for the identification of p62 mediated aggregate formation modulators. Such assays generally use isolated molecules, can be run quickly and in large numbers, thereby increasing the amount of information obtainable in a short period of time. A variety of vessels may be used to run the assays, including test tubes, plates, dishes and other surfaces such as dipsticks or beads.

One example of a cell free assay is a binding assay. While not directly addressing function, the ability of a modulator to bind to a target molecule, for example a nucleic acid encoding p62 or TRAF6, in a specific fashion is strong evidence of a related biological effect. Such a molecule can bind to a p62 or TRAF6 nucleic acid and modulate expression of p62 or TRAF6, for example upregulate or down regulate expression of p62 or TRAF6. The binding of a molecule to a target may, in and of itself, be inhibitory, due to steric, allosteric or charge—charge interactions or may downregulate or inactivate p62 or TRAF6. The target may be either free in solution, fixed to a support, expressed in or on the surface of a cell. Either the target or the compound may be labeled, thereby permitting determining of binding. Usually, the target will be the labeled species, decreasing the chance that the labeling will interfere with or enhance binding. Competitive binding formats can be performed in which one of the agents is labeled, and one may measure the amount of free label versus bound label to determine the effect on binding.

A technique for high throughput screening of compounds is described in WO 84/03564. Large numbers of small peptide test compounds are synthesized on a solid substrate, such as plastic pins or some other surface. Bound polypeptide is detected by various methods.

Cell Assays

Other embodiments include methods of screening compounds for their ability to modulate p62 activity in cells. Various cell lines can be utilized for such screening assays, including cells specifically engineered for this purpose. Suitable cells include, but are not limited to, mammalian cells. Cells can also be engineered to express p62 or TRAF6 or a modulator of p62 or TRAF6 or a combination of both p62 or TRAF6 or a modulator of p62 or TRAF6. Furthermore, those of skill in the art will appreciate that stable or transient transfections, which are well known and used in the art, may be used in the disclosed embodiments.

For example, a transgenic cell comprising an expression vector can be generated by introducing the expression vector into the cell. The expression vector can encode, for example, GFP-p62. The introduction of DNA into a cell or a host cell is well known technology in the field of molecular biology and is described, for example, in Sambrook et al., Molecular Cloning 3rd Ed. (2001). Methods of transfection of cells include calcium phosphate precipitation, liposome mediated transfection, DEAE dextran mediated transfection, electroporation, ballistic bombardment, and the like. Alternatively, cells may be simply transfected with the disclosed expression vector using conventional technology described in the references and examples provided herein. The host cell can be a prokaryotic or eukaryotic cell, or any transformable organism that is capable of replicating a vector and/or expressing a heterologous gene encoded by the vector. Numerous cell lines and cultures are available for use as a host cell, and they can be obtained through the American Type Culture Collection (ATCC), which is an organization that serves as an archive for living cultures and genetic materials (www.atcc.org).

A host cell can be selected depending on the nature of the transfection vector and the purpose of the transfection. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE, La Jolla, Calif.). Alternatively, bacterial cells such as E. coli LE392 could be used as host cells for phage viruses. Eukaryotic cells that can be used as host cells include, but are not limited to, yeast, insects and mammals. Examples of mammalian eukaryotic host cells for replication and/or expression of a vector include, but are not limited to, HeLa, NIH3T3, Jurkat, 293, Cos, CHO, Saos, and PC12. Examples of yeast strains include, but are not limited to, YPH499, YPH500 and YPH501. Many host cells from various cell types and organisms are available and would be known to one of skill in the art. Similarly, a viral vector may be used in conjunction with either an eukaryotic or prokaryotic host cell, particularly one that is permissive for replication or expression of the vector.

Depending on the assay, culture may be required. The cell is examined using any of a number of different physiologic assays. Alternatively, molecular analysis may be performed, for example, looking at protein expression, mRNA expression (including differential display of whole cell or polyA RNA) and others.

One particular assay provides a method for identifying modulators of p62-mediated aggregate formation including the steps of determining binding of TRAF6 or a fragment thereof to p62 or a fragment thereof in the presence of a test compound and selecting the test compound that reduces or inhibits TRAF6 binding to p62 and reduces or inhibits intracellular aggregate formation.

Detection of TRAF6 interaction with p62 in the presence of a test compound compared to TRAF6 interaction with p62 in the absence of the test compound can be determined using conventional techniques. For example, one or more of p62, TRAF6, or the test compound can be labeled with a detectable label. Representative detectable labels include, but are not limited to radioisotopes, fluorophores, chromophores, enzymes, biotin-streptavidin, nanoparticles, metal particles, quantum dots, and the like. In one example, unlabeled p62 or unlabeled TRAF6 can be fixed to a solid support, for example a membrane, plate, pin, comb, resin, column, or the like. Labeled test compound can be applied to the unlabeled p62 or unlabeled TRAF6 on the solid support, for example under non-denaturing conditions. Excess labeled test compound can be washed away, and any bound labeled test compound can be eluted. Detection of label in the eluate indicates that the test compound interacts with p62 or TRAF6. It will be appreciated that the test compound can be fixed to the solid support and labeled p62 or TRAF6 can be added thereto to determined binding or interaction with the test compound.

Once a compound has been identified as interacting with p62 or TRAF6, the test compound can then be assayed for the ability to reduce or inhibit p62 mediated aggregate formation. An exemplary method includes contacting a cell engineered to express a detectable p62 polypeptide, for example GFP-p62 fusion polypeptide. The engineered cell can be contacted with the test compound and an aggregate inducing agent. The cell can then be assayed for the formation of aggregates containing or associated with the GFP-p62 fusion protein. A reduction in the formation of aggregates in the presence of the test compound and the aggregate inducing agent compared to the aggregate inducing agent alone indicates the test compound is an inhibitor of aggregate formation.

The cell engineered to express a detectable p62 polypeptide can optionally be engineered to express a detectable TRAF6 polypeptide. The association of the detectable p62 polypeptide with the detectable TRAF6 polypeptide inside the cell can then be detected by identifying each polypeptide independently and overlaying their respective positions in the cell. Alternatively, the polypeptides can fluoresce at different emission wavelengths. If the polypeptides are associated in the cell, the fluorescence can be combined to produce a color different from the emission of the fluorescent p62 or the fluorescent TRAF6 polypeptide.

Detectable changes in fluorescence indicative or p62-TRAF6 interaction can also occur by fluorescence energy resonance transfer (FRET) between a fluorescently labeled p62 and a fluorescently labeled TRAF6. In one embodiment, GFP-62 can be expressed in a cell, and TRAF6 can be labeled with Alexa546. Alexa-TRAF6 can be introduced into the cytoplasm of the cells expressing GFP-62 by microinjection into the cytoplasm, shear loading, LIPOFECTAMINE, or operably linking the labeled protein to a PTD. A 488 ex/598 em filter set can be used to detect FRET. FRET can occur from GFP-p62 to Alexa-TRAF6 when the two labeled polypeptides interact or are in close proximity to each other. Compounds that reduce or increase detectable FRET can be selected.

In vivo Assays

In vivo assays involve the use of various animal models, including non-human transgenic animals that have been engineered to have specific defects, or carry markers that can be used to measure the ability of a test compound to reach and affect different cells within the organism. Due to their size, ease of handling, and information on their physiology and genetic make-up, mice are a preferred embodiment, especially for transgenic animals. However, other animals are suitable as well, including rats, rabbits, hamsters, guinea pigs, gerbils, woodchucks, cats, dogs, sheep, goats, pigs, cows, horses and monkeys (including chimps, gibbons and baboons). Assays for modulators may be conducted using an animal model derived from any of these species.

In such assays, one or more test compounds are administered to an animal, and the ability of the test compound(s) to alter one or more characteristics, as compared to a similar animal not treated with the test compound(s), identifies a modulator. The characteristics may be any of those discussed above with regard to the function of a particular compound (e.g., enzyme, receptor, hormone) or cell (e.g., growth or regeneration), or instead a broader indication nerve cell regeneration, axonal growth or regeneration, or the like.

Other embodiments provide methods of screening for a test compound that modulates the function of p62 mediated aggregate formation. In these embodiments, a representative method generally includes the steps of administering a test compound to the animal and determining the ability of the test compound to reduce one or more characteristics of p62 mediated aggregate formation.

Treatment of these animals with test compounds will involve the administration of the compound, in an appropriate form, to the animal. Administration will be by any route that could be utilized for clinical or non-clinical purposes, including, but not limited to, oral, nasal, buccal, or even topical. Alternatively, administration may be by intratracheal instillation, bronchial instillation, intradermal, subcutaneous, intramuscular, intraperitoneal or intravenous injection. Specifically contemplated routes are systemic intravenous injection, regional administration via blood or lymph supply, or directly to an affected site.

Determining the effectiveness of a compound in vivo may involve a variety of different criteria. Also, measuring toxicity and dose response can be performed in animals in a more meaningful fashion than in in vitro or in cyto assays.

Expression Systems

Some embodiments of the present disclosure provided compositions containing p62 or TRAF6 modulators that can be expressed as encoded polypeptides or proteins. The engineering of DNA segment(s) for expression in a prokaryotic or eukaryotic system may be performed by techniques generally known to those of skill in recombinant expression. It is believed that virtually any expression system may be employed in the expression of the claimed nucleic and amino sequences.

Generally speaking, it may be more convenient to employ as the recombinant polynucleotide a cDNA version of the polynucleotide. It is believed that the use of a cDNA version will provide advantages in that the size of the gene will generally be much smaller and more readily employed to transfect the targeted cell than will a genomic gene, which will typically be up to an order of magnitude larger than the cDNA gene. However, the present disclosure does not exclude the possibility of employing a genomic version of a particular gene where desired.

As used herein, the terms "engineered" and "recombinant" cells are intended to refer to a cell into which an exogenous DNA segment or gene, such as a cDNA or gene has been introduced. Therefore, engineered cells are distinguishable from naturally occurring cells which do not contain a recombinantly introduced exogenous DNA segment or gene. Engineered cells are thus cells having a gene or genes introduced through the hand of man. Recombinant cells include those having an introduced cDNA or genomic DNA, and also include genes positioned adjacent to a promoter not naturally associated with the particular introduced gene.

To express a recombinant encoded polypeptide protease or proteinase inhibitor in accordance with the present disclosure one would prepare an expression vector that includes a polynucleotide under the control of one or more promoters. To bring a coding sequence "under the control of" a promoter, one positions the 5' end of the translational initiation site of the reading frame generally between about 1 and 50 nucleotides "downstream" of (i.e., 3' of) the chosen promoter. The "upstream" promoter stimulates transcription of the inserted DNA and promotes expression of the encoded recombinant protein. This is the meaning of "recombinant expression" in the context used here.

Many standard techniques are available to construct expression vectors containing the appropriate nucleic acids and transcriptional/translational control sequences in order to achieve protein or peptide expression in a variety of host-expression systems. Cell types available for expression include, but are not limited to, bacteria, such as E. coli and B. subtilis transformed with recombinant phage DNA, plasmid DNA or cosmid DNA expression vectors.

Certain examples of prokaryotic hosts are E. Coli strain RR1, E. coli LE392, E. coli B, E. coli$_X$ 1776 (ATCC No. 31537) as well as E. coli W3110 (F-, lambda-, prototrophic, ATCC No. 273325); bacilli such as Bacillus subtilis; and other enterobacteriaceae such as Salmonella typhimurium, Serratia marcescens, and various Pseudomonas species.

In general, plasmid vectors containing replicon and control sequences that are derived from species compatible with the host cell are used in connection with these hosts. The vector ordinarily carries a replication site, as well as marking sequences that are capable of providing phenotypic selection in transformed cells. For example, E. coli is often transformed using pBR322, a plasmid derived from an E. coli species. Plasmid pBR322 contains genes for ampicillin and tetracycline resistance and thus provides easy means for identifying transformed cells. The pBR322 plasmid, or other microbial plasmid or phage must also contain, or be modified to contain, promoters that can be used by the microbial organism for expression of its own proteins.

In addition, phage vectors containing replicon and control sequences that are compatible with the host microorganism can be used as transforming vectors in connection with these hosts. For example, the phage lambda may be utilized in making a recombinant phage vector that can be used to transform host cells, such as E. coli LE392.

Further useful vectors include pIN vectors and pGEX vectors, for use in generating glutathione S-transferase (GST) soluble fusion proteins for later purification and separation or cleavage. Other suitable fusion proteins are those with β-galactosidase, ubiquitin, or the like.

Promoters that are most commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

For expression in Saccharomyces, the plasmid YRp7, for example, is commonly used. This plasmid contains the trp1 gene, which provides a selection marker for a mutant strain of yeast lacking the ability to grow in tryptophan, for example ATCC No. 44076 or PEP4-1. The presence of the trp1 lesion as a characteristic of the yeast host cell genome then provides an effective environment for detecting transformation by growth in the absence of tryptophan.

Suitable promoting sequences in yeast vectors include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other suitable promoters, which have the additional advantage of transcription controlled by growth conditions, include the promoter region for alcohol dehydrogenase 2, isocytochrome C, acid phosphatase, degradative enzymes associated with nitrogen metabolism, the aforementioned glyceraldehyde-3-phosphate dehydrogenase, and enzymes responsible for maltose and galactose utilization.

In addition to micro-organisms, cultures of cells derived from multicellular organisms may also be used as hosts. In principle, any such cell culture is workable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing one or more coding sequences.

In a useful insect system, Autographica californica nuclearpolyhedrosis virus (AcNPV) is used as a vector to express foreign genes. The virus grows in Spodoptera frugiperda cells. The isolated nucleic acid coding sequences are cloned into non-essential regions (for example the polyhedron gene) of the virus and placed under control of an AcNPV promoter (for example, the polyhedron promoter). Successful insertion of the coding sequences results in the inactivation of the polyhedron gene and production of non-occluded recombinant virus (i.e., virus lacking the proteinaceous coat coded for by the polyhedron gene). These recombinant viruses are then used to infect Spodoptera frugiperda cells in which the inserted gene is expressed (e.g., U.S. Pat. No. 4,215,051, incorporated herein by reference).

Examples of useful mammalian host cell lines are VERO and HeLa cells, Chinese hamster ovary (CHO) cell lines, W138, BHK, COS-7, 293, HepG2, NIH3T3, RIN and MDCK cell lines. In addition, a host cell may be chosen that modulates the expression of the inserted sequences, or modifies and processes the gene product in the specific fashion desired.

Such modifications (e.g., glycosylation) and processing (e.g., cleavage) of protein products may be important for the function of the encoded protein.

Different host cells have characteristic and specific mechanisms for the post-translational processing and modification of proteins. Appropriate cell lines or host systems can be chosen to ensure the correct modification and processing of the foreign protein expressed. Expression vectors for use in mammalian cells ordinarily include an origin of replication (as necessary), a promoter located in front of the gene to be expressed, along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g., the adenovirus late promoter; the vaccinia virus 7.5K promoter). Further, it is also possible, and may be desirable, to utilize promoter or control sequences normally associated with the desired gene sequence, provided such control sequences are compatible with the host cell systems.

A number of viral based expression systems may be utilized, for example, commonly used promoters are derived from polyoma, Adenovirus 2, cytomegalovirus and Simian Virus 40 (SV40). The early and late promoters of SV40 virus are useful because both are obtained easily from the virus as a fragment which also contains the SV40 viral origin of replication. Smaller or larger SV40 fragments may also be used, provided there is included the approximately 250 bp sequence extending from the HindIII site toward the Bg/I site located in the viral origin of replication.

In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing proteins in infected hosts.

Specific initiation signals may also be required for efficient translation of the claimed isolated nucleic acid coding sequences. These signals include the ATG initiation codon and adjacent sequences. Exogenous translational control signals, including the ATG initiation codon, may additionally need to be provided. One of ordinary skill in the art would readily be capable of determining this need and providing the necessary signals. It is well known that the initiation codon must be in-frame (or in-phase) with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements or transcription terminators.

In eukaryotic expression, one will also typically desire to incorporate into the transcriptional unit an appropriate polyadenylation site if one was not contained within the original cloned segment. Typically, the poly A addition site is placed about 30 to 2000 nucleotides "downstream" of the termination site of the protein at a position prior to transcription termination.

For long-term, high-yield production of recombinant proteins, stable expression is preferred. For example, cell lines that stably express constructs encoding proteins may be engineered. Rather than using expression vectors that contain viral origins of replication, host cells can be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1-2 days in an enriched medium, and then are switched to a selective medium. The selectable marker in the recombinant plasmid confers resistance to the selection and allows cells to stably integrate the plasmid into their chromosomes and grow to form foci, which in turn can be cloned and expanded into cell lines.

A number of selection systems may be used, including, but not limited, to the herpes simplex virus thymidine kinase, hypoxanthine-guanine phosphoribosyltransferase and adenine phosphoribosyltransferase genes, in tk⁻, hgprt⁻ or aprt⁻ cells, respectively. Also, antimetabolite resistance can be used as the basis of selection for dhfr, which confers resistance to methotrexate; gpt, which confers resistance to mycophenolic acid; neo, which confers resistance to the aminoglycoside G-418; and hygro, which confers resistance to hygromycin.

It is contemplated that the isolated nucleic acids of the disclosure may be "overexpressed", i.e., expressed in increased levels relative to its natural expression in human cells, or even relative to the expression of other proteins in the recombinant host cell. Such overexpression may be assessed by a variety of methods, including radio-labeling and/or protein purification. However, simple and direct methods are preferred, for example, those involving SDS/PAGE and protein staining or immunoblotting, followed by quantitative analyses, such as densitometric scanning of the resultant gel or blot. A specific increase in the level of the recombinant protein or peptide in comparison to the level in natural human cells is indicative of overexpression, as is a relative abundance of the specific protein in relation to the other proteins produced by the host cell and, e.g., visible on a gel.

Purification of Expressed Proteins

Further aspects of the present disclosure concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state, i.e., in this case, relative to its purity within a cell extract. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50% or more of the proteins in the composition.

Various methods for quantifying the degree of purification of the protein or peptide will be known to those of skill in the art in light of the present disclosure. These include, for example, determining the specific activity of an active fraction, or assessing the number of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number". The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, polyethylene glycol, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater-fold purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., Biochem. Biophys. Res. Comm., 76:425, 1977). It will therefore be appreciated that under differing electrophoresis conditions, the apparent molecular weights of purified or partially purified expression products may vary.

Pharmaceutical Compositions

Pharmaceutical compositions and dosage forms of the disclosure include a pharmaceutically acceptable salt of disclosed compositions or compounds, including, but not limited to, peptides, or a pharmaceutically acceptable polymorph, solvate, hydrate, dehydrate, co-crystal, anhydrous, or amorphous form thereof. Specific salts of disclosed compounds include, but are not limited to, sodium, lithium, potassium salts, and hydrates thereof.

Pharmaceutical unit dosage forms of the compounds of this disclosure are suitable for oral, mucosal (e.g., nasal, sublingual, vaginal, buccal, or rectal), parenteral (e.g., intramuscular, subcutaneous, intravenous, intraarterial, or bolus injection), topical, or transdermal administration to a patient. Examples of dosage forms include, but are not limited to: tablets; caplets; capsules, such as hard gelatin capsules and soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the compositions of the disclosure will typically vary depending on their use. A parenteral dosage form may contain smaller amounts of the active ingredient than an oral dosage form used to treat the same disease or disorder. These and other ways in which specific dosage forms encompassed by this disclosure will vary from one another will be readily apparent to those skilled in the art. See, e.g., Remington's Pharmaceutical Sciences, 18th ed., Mack Publishing, Easton, Pa. (1990).

Pharmaceutical compositions and unit dosage forms of the disclosure typically also include one or more pharmaceutically acceptable excipients or diluents. Advantages provided by specific compounds of the disclosure, such as, but not limited to, increased solubility and/or enhanced flow, purity, or stability (e.g., hygroscopicity) characteristics can make them better suited for pharmaceutical formulation and/or administration to patients than the prior art. Suitable excipients are well known to those skilled in the art of pharmacy or pharmaceutics, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets or capsules may contain excipients not suited for use in parenteral dosage forms. The suitability of a particular excipient may also depend on the specific active ingredients in the dosage form. For example, the decomposition of some active ingredients can be accelerated by some excipients such as lactose, or when exposed to water. Active ingredients that include primary or secondary amines are particularly susceptible to such accelerated decomposition.

The disclosure further encompasses pharmaceutical compositions and dosage forms that include one or more compounds that reduce the rate by which an active ingredient will decompose. Such compounds, which are referred to herein as "stabilizers," include, but are not limited to, antioxidants such as ascorbic acid, pH buffers, or salt buffers. In addition, pharmaceutical compositions or dosage forms of the disclosure may contain one or more solubility modulators, such as sodium chloride, sodium sulfate, sodium or potassium phosphate or organic acids. A specific solubility modulator is tartaric acid.

Like the amounts and types of excipients, the amounts and specific type of active ingredient in a dosage form may differ depending on factors such as, but not limited to, the route by which it is to be administered to patients. However, typical dosage forms of the compounds of the disclosure include a pharmaceutically acceptable salt, or a pharmaceutically acceptable polymorph, solvate, hydrate, dehydrate, co-crystal, anhydrous, or amorphous form thereof, in an amount of from about 10 mg to about 1000 mg, preferably in an amount of from about 25 mg to about 750 mg, more preferably in an amount of from 50 mg to 500 mg, even more preferably in an amount of from about 30 mg to about 100 mg.

Additionally, the compounds and/or compositions can be delivered using lipid- or polymer-based nanoparticles. For example, the nanoparticles can be designed to improve the pharmacological and therapeutic properties of drugs administered parenterally (Allen, T. M., Cullis, P. R. Drug delivery systems: entering the mainstream. Science. 303(5665):1818-22 (2004)).

Topical dosage forms of the disclosure include, but are not limited to, creams, lotions, ointments, gels, sprays, aerosols, solutions, emulsions, and other forms known to one of skill in the art. See, e.g., Remington's Pharmaceutical Sciences, 18th ed., Mack Publishing, Easton, Pa. (1990); and Introduction to Pharmaceutical Dosage Forms, 4th ed., Lea & Febiger, Philadelphia, Pa. (1985). For non-sprayable topical dosage forms, viscous to semi-solid or solid forms including a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as freon), or in a squeeze bottle. Moisturizers or humectants can also be added to pharmaceutical compositions and dosage forms if desired. Examples of such additional ingredients are well known in the art. See, e.g., Remington's Pharmaceutical Sciences, 18th Ed., Mack Publishing, Easton, Pa. (1990).

Transdermal and mucosal dosage forms of the compositions of the disclosure include, but are not limited to, ophthalmic solutions, patches, sprays, aerosols, creams, lotions, suppositories, ointments, gels, solutions, emulsions, suspensions, or other forms known to one of skill in the art. See, e.g., Remington's Pharmaceutical Sciences, 18th Ed., Mack Publishing, Easton, Pa. (1990); and Introduction to Pharmaceutical Dosage Forms, 4th Ed., Lea & Febiger, Philadelphia, Pa. (1985). Dosage forms suitable for treating mucosal tissues within the oral cavity can be formulated as mouthwashes, as oral gels, or as buccal patches. Additional transdermal dosage forms include "reservoir type" or "matrix type" patches, which can be applied to the skin and worn for a specific period of time to permit the penetration of a desired amount of active ingredient.

Examples of transdermal dosage forms and methods of administration that can be used to administer the active ingredient(s) of the disclosure include, but are not limited to, those disclosed in U.S. Pat. Nos.: 4,624,665; 4,655,767; 4,687,481; 4,797,284; 4,810,499; 4,834,978; 4,877,618; 4,880,633; 4,917,895; 4,927,687; 4,956,171; 5,035,894; 5,091,186; 5,163,899; 5,232,702; 5,234,690; 5,273,755; 5,273,756; 5,308,625; 5,356,632; 5,358,715; 5,372,579; 5,421,816; 5,466;465; 5,494,680; 5,505,958; 5,554,381; 5,560,922; 5,585,111; 5,656,285; 5,667,798; 5,698,217; 5,741,511; 5,747,783; 5,770,219; 5,814,599; 5,817,332; 5,833,647; 5,879,322; and 5,906,830, each of which are incorporated herein by reference in their entirety.

Suitable excipients (e.g., carriers and diluents) and other materials that can be used to provide transdermal and mucosal dosage forms encompassed by this disclosure are well known to those skilled in the pharmaceutical arts, and depend on the particular tissue or organ to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof, to form dosage forms that are non-toxic and pharmaceutically acceptable.

Depending on the specific tissue to be treated, additional components may be used prior to, in conjunction with, or subsequent to treatment with pharmaceutically acceptable salts of a p62 modulator of the disclosure. For example, penetration enhancers can be used to assist in delivering the active ingredients to or across the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as TWEEN 80 (polysorbate 80) and SPAN 60 (sorbitan monostearate).

The pH of a pharmaceutical composition or dosage form, or of the tissue to which the pharmaceutical composition or dosage form is applied, may also be adjusted to improve delivery of the active ingredient(s). Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of the active ingredient(s) so as to improve delivery. In this regard, stearates can serve as a lipid vehicle for the formulation, as an emulsifying agent or surfactant, and as a delivery-enhancing or penetration-enhancing agent. Different hydrates, dehydrates, co-crystals, solvates, polymorphs, anhydrous, or amorphous forms of the pharmaceutically acceptable salt of a p62 modulator can be used to further adjust the properties of the resulting composition.

Kits

Another embodiment provides a kit for assaying p62 mediated aggregate formation. An exemplary kit can contain a vector encoding GFP-p62 for transfecting a cell, for example, a mammalian cell. Alternatively, the kit can contain a cell expressing GFP-p62. The cell can be stably transfected with one or more GFP-p62 constructs, and can optionally overexpress GFP-62. The kit can also contain reagents, buffers, and culture reagents needed to culture the transfected cells.

The kit can also contain an aggregate inducing agent. A representative aggregate inducing agent includes, but is not limited to, N-acetyl-Leu-Leu-Norleu-AL (ALLN). Other components of the kit include, but are not limited to, reagents for detecting p62, a recombinant polypeptide, for example a polypeptide comprising SEQ ID NO. 1 or 2 operably linked to a protein transduction domain, a control peptide comprising SEQ ID NO. 5, reagents for detecting p62 (SEQ ID NO. 1), $p62_{1-385}$ (SEQ ID NO. 2), TRAF6, or a combination thereof, a mammalian cell engineered to express $p62_{1-385}$ (SEQ ID NO. 2); and an expression vector encoding $p62_{1-385}$, or a combination thereof.

Materials and Methods

Human Brain Samples—Postmortem adult human brain specimens (hippocampus) were obtained from the Harvard Brain Tissue Resource Center, McLean Hospital, Massachusetts, in accordance with the Institutional Review Board—approved guidelines. The samples were clinico-pathologically-verified for definite Alzheimer's disease (AD, Braak 6). The brain tissues were from both sexes with age of death ranging from 67-87 years. The postmortem interval was between 4.77 to 17.83 h. Control brain tissue was obtained from University of Alabama Birmingham, Alzheimer's Disease Research Center and was age matched at death and postmortem delay compared to samples taken from the AD patient's brain.

Cells, Antibodies and Reagents—Human embryonic kidney 293 cells (HEK 293) were grown in Dulbecco's Modified Eagle Medium (DMEM) supplemented with 10% fetal calf serum at 37° C. in a 5% CCh humidified incubator. PC12 cells were grown on plates coated with rat-tail collagen in DMEM containing 10% horse serum and 5% calf serum and antibiotics (50 units/ml penicillin and 50 mg/ml streptomycin). Subconfluent HEK 293 cells were transfected by the calcium phosphate method using a commercially available transfection kit (Specialty Media, Phillipsburg, Pa.) and PC12 cells using LipofectAMINE 2000 (Invitrogen Life Technologies). After 12 h transfection, the medium was removed and cells were rinsed once with phosphate-buffered saline (PBS) and incubated with fresh medium. The cells were lysed with SDS lysis buffer to detect covalent interaction (50 mM Tris-HCl pH 7.5, 150 mM Nad, 10 mM NaF, 0.5% Triton X-100, 1 mM $Na_3VO_4$ 1 mM phenylmethylsulfonyl fluoride, 2 µg/ml leupeptin, aprotinin and 1% SDS) or triton lysis buffer (SDS lysis buffer minus SDS) for non-covalent interaction. Protein concentration was determined using DC assay (Bio-Rad) for samples containing SDS lysis buffer or by Bradford procedure (Bio-Rad) for all samples without SDS, using bovine serum albumin (BSA) as a standard. Mouse anti-ubiquitin, anti-TRAF6 and goat anti-tau were purchased from Santa Cruz Biotechnologies (Santa Cruz, Calif.). 12E8 (p-tau) was generous gift from Dr. Gail Johnson, University of Alabama, Birmingham. Rabbit anti-UbcH7, ubiquitin K63 only and ubiquitin aldehyde Ub-H was from Boston Biochem (Cambridge, Mass., and rabbit anti-tau was purchased from DAKO (Carpinteria, Calif.). Mouse anti-Rpt1, 26S proteasome and ubiquitm-activating enzyme El (mammalian) were purchased from Affiniti Research Products (United Kingdom). Cycloheximide, ubiquitin and the inhibitors N-acetyl-Leu-Leu-Norleu-AL (ALLN), and chloroquine were bought from Sigma Aldrich. Z-Leu-Leu-Leu-CHO (MG1 32) was obtained from Biomol Research Laboratories, Inc. The TRAF6 inhibitor and control peptide were synthesized by Alpha Diagnostics, San Antonio, Tex., Aβ peptide 1-42 and 42-1 was synthesized by Biopeptide Co., San Diego, Calif. The live/dead viability/cytotoxicity kit was purchased from Molecular Probes (Eugene, Oreg.), horseradish peroxidase conjugated secondary antibody from Amersham Biosciences (Piscataway, N.J.) and SDS-PAGE reagents from Bio-Rad (Hercules, Calif.).

Isolation of inclusion bodies—The procedure was modified from the method for isolating inclusions from multiple system atrophy brains. Procedures were carried out at 4° C. unless otherwise stated. The hippocampus was homogenized using homogenization buffer (HB: 0.32 M sucrose, 50 mM Tris HCl at pH 7.4, 5 mM EDTA, 1 mg/ml leupeptin, 1 mg/ml pepstatin and 17.4 mg/ml phenylmethylsulfonyl fluoride), filtered through glass wool, followed by washing three times with HB and centrifuged at 1,000×g for 10 min to obtain a pellet. The pellet was dissolved in HB and percoll was added to a concentration of 14% (v/v). The sample was overlaid on 35% percoll (v/v in HB) and centrifuged for 30 min at 35,000×g. The material at the interface was collected and washed three times at 4,000×g for 10 min in 50 mM Tris-HCl-buffered saline at pH 7.4 containing 1 mg/ml leupeptin, 1 mg/ml pepstatin and 17.4 mg/ml phenylmethylsulfonyl fluoride. The pellet was suspended in TBS buffer containing 5 mM $MgCl_2$, 2 mM EGTA, 1 mg/ml leupeptin, 1 mg/ml pepstatin, 17.4 mg/ml phenylmethylsulfonyl fluoride and 1 µg/ml DNase I. The suspension was vigorously shaken and rotated overnight at 37° C. followed by washing three times in sucrose Tris buffer (STB 0.32 M sucrose, 50 mM Tris-HCl at pH 7.4, 1 mg/ml leupeptin, 1 mg/ml pepstatin and 17.4 mg/ml phenylmethylsulfonyl fluoride) at 4,000×g for 10 min. The resulting pellet was dissolved in 12% percoll (v/v in STB) and overlaid on 35% percoll (v/v in the STB). After centrifugation at 35,000×g for 30 min, the material banding just below the sample, 35% percoll interface, was collected and filtered through 20 mm nylon mesh (Small Parts Inc., Miami Lakes, Fla.). The protein amount was determined using Bradford reagent (Bio-Rad) and bovine serum albumin (BSA) as a standard.

p62 Coupled Dynabeads Pull Down Assay—To couple the Dynabeads with p62, 3 µg of affinity purified p62 rabbit antiserum was added to $10^7$-280 sheep anti-Rabbit IgG Dynabeads (Dynal Biotech Inc, Lake Success, N.Y.), and incubated for 24 h at 4° C. in a shaker. The antibody-coated Dynabeads were collected using a Magnetic Particle Concentrator (Dynal). Antibody coated Dynabeads were washed 4 times at 4° C. in washing buffer [PBS/FCS (1% fetal calf serum)]. To pull down the p62 from the inclusions, normal horse serum (10% v/v) was first added to the inclusions and rotated for 60 min at room temperature for blocking. The inclusions were incubated with 100 µl of p62 antibody coated Dynabeads (from 6-7×$10^8$ beads/ml) per mg of inclusion for 4 h at 4° C. The beads were washed three times with washing buffer (PBS/1% PCS) and collected in an Eppendorf tube by using a Magnetic Particle Concentrator. SDS-PAGE sample buffer was added to the beads, boiled to release the bound protein, followed by SDS-PAGE and immunoblotting.

Immunofluorescence staining—All steps were done at room temperature unless stated otherwise. The inclusion bodies were placed on poly-L-lysine coated 12 well slides (Cel-line/Erie Scientific Co., Portmouth, N.H.) and let partially dry. Inclusion bodies on the slides were fixed for 10 min in 3% paraformaldehyde (Electron Microscopy Sciences, Fort Washington, Pa.) and permeabilized with 0.1% Triton X-100 in PBS for 15 minutes. The inclusion bodies were incubated in blocking buffer (3% non fat dry milk in PBS) for 1 h, prior to incubation with primary antibodies at 4° C. overnight. After washing with PBS, the secondary antibody (Molecular Probes Inc., Eugene, Oreg.) in blocking buffer was applied for 1 h. After extensive washing in PBS, the samples were mounted using Vectashield (Vector Laboratories Inc., Burlingame, Calif.). The cells were fixed with 3% paraformaldehyde and processed similar to that of inclusion staining.

For Thioflavin S staining, the inclusions were fixed and incubated with 0.05% thioflavin S (Sigma) for 10 min, then washed three times with 80% ethanol. Cells were analyzed using a BioRad MRC 1024 Laser Scanning Confocal Microscope using 100×objective. The sizes of the inclusion bodies were measured using the software Metamorf.

Electron Microscopy—Samples were fixed with 2% paraformaldehyde and 0.5% glutaraldehyde in 0.1 M phosphate buffer at pH 7.4 for 2 h at 4° C. and post fixed for 2 h in 1% $OsO_4$, dehydrated in cold graded ethanol and embedded in LR White resin (Ted Pella, Inc., Redding, Calif.). Ultra thin sections (70 nm) on grids were blocked with 2% BSA in PBS for 1 h at room temperature and incubated with primary antibody at 4° C. overnight. The grids were then washed three times with PBS for 10 min, and incubated with 20 nm colloidal gold labeled protein A (Sigma) for 1 h at room temperature. In addition, controls were incubated with non related primary antibody and gold labeled secondary antibody. The grids were washed extensively with PBS, stained with aqueous 1% uranyl acetate and 0.4% lead citrate, air dried and examined on a Philips 301 electron microscope.

Immunoprecipitation and Western blotting—Each mg of lysate/inclusion bodies was incubated with 41 ng of primary antibody at 4° C. for 3 h and then with 50 µl of 50% agarose-coupled secondary antibody for 2 more hours at 4 C. The beads were washed three times with lysis buffer, eluted by adding SDS-PAGE sample buffer, and subjected to SDS-PAGE in 7.5-12% acrylamide gels. Immunoblotting was performed on nitrocellulose membranes and analyzed by western blotting with ECL detection reagents (Amersham Biosciences).

GST Pull-Down Assay—Glutathione beads coupled with p62 UBA domain were washed three times with binding buffer (20 mM Tris-HCl, pH 7.6, 50 mM NaCl, 0.1% Nonidet P-40, 0.5 M dithiothreitol, 1 mM phenylmethylsulfonyl fluoride) containing 25 µg/ml of BSA. For each mg of lysate, 2.5 µg of GST-UBA domain was added and rotated for 2 h at room temperature. The beads were washed 3 times with binding buffer and boiled in SDS-PAGE sample buffer, followed by separation employing a 7.5% SDS-gel, and western blotting with appropriate antibody.

In Vitro Ubiquitination and Deubiquitination Assay—His-tagged tau construct was expressed in HEK 293 cells by calcium phosphate method. The cells were collected, washed with PBS and lysed with SDS lysis buffer. The lysate was immunoprecipitated with tau antibody and bound to secondary antibody coupled with agarose beads. Fifty microliters of the reaction buffer (50 mM Tris pH 7.5, 2.5 mM MgCl$_2$, 2 mM DTT, 2 mM ATP) containing 100 ng E1, 200 ng UbcH7 (E2), 100 µg TRAF6 (E3) and 5 µg of GST-WT Ub, or its mutants K29R, K48R, and K63R Ub was added to the immunoprecipitated tau. The beads were incubated at 37° C. for 2 h by continuous shaking, then washed three times with reaction buffer. The proteins were released by boiling for 2 min in SDS-PAGE sample buffer, electrophoresed on 7.5% SDS-PAGE and western blotted with antibody to ubiquitin and tau. For the in vitro deubiquitination assay, the ubiquitinated tau was treated with 26S proteasome (40 or 80 nM) in 30 µl of buffer containing 50 mM Tris-HCl, pH 7.5, 2 mM MgCl$_2$, 2 mM ATP for 2 h at 37° C. The deubiquitination of tau by the 26S proteasome was blocked by the addition of ubiquitin aldehyde (Ub-H), an inhibitor of ubiquitin isopeptidases (1 or 10 µM). The samples were boiled in sample buffer, resolved by 7.5% SDS-PAGE and western blotted with anti-ubiquitin or anti-tau.

Triton Solubility of Tau—Briefly, cells were lysed using lysis buffer (50 mM Tris-HCl pH 7.5, 150 mM NaCl, 10 mM NaF, 1 mM NasVO$_4$; 1 mM phenylmethylsulfonyl fluoride, 2 µg/ml leupeptin and aprotinin which contains 1% Triton X-100, then centrifuged at 20,000×g for 1 h at 4° C. The Triton soluble supernatants were collected and the pellets were further resolved in lysis buffer containing 4% SDS and centrifuged at 20,000×g for 1 h at 22° C. Supernatant was referred to as 1% Triton insoluble fractions. Both fractions were immunoprecipitated with tau antibody, separated by SDS polyacrylamide gel electrophoresis and analyzed by western blotting.

Turnover of Tau—HEK cells were cotransfected either with antisense (AS) p62, myc-tagged p62 or K63R ubiquitin mutant along with tau. 24 h post transfection, the cells were treated with 20 µg/ml cycloheximide for 6 h, 12 h, 24 h and 36 h. After treatment, the cells were lysed with triton lysis buffer and protein was measured. Equal concentration of protein (30 µg) was separated by SDS-polyacrylamide gel electrophoresis and western blotted to assess the turnover of tau.

Cell Death Assay—Live and dead cells were identified with LIVE/DEAD Viability/Cytotoxicity Kit (Molecular Probes, Eugene, Oreg.) according to the manufacturer's instruction.

Cell Survival Assay—PC 2 cells were treated with 50 ng/ml NGF 24 h prior to addition of TRAF6 control or inhibitor peptide (75 µM). After 5 h, the cells were treated for an additional 24 h with or without MG132 (25 µM), Aβ peptide 42-1 or 1-42 (10 µM). Cell survival was measured by MTS assay.

EXAMPLES

Example 1

Figure 1B:
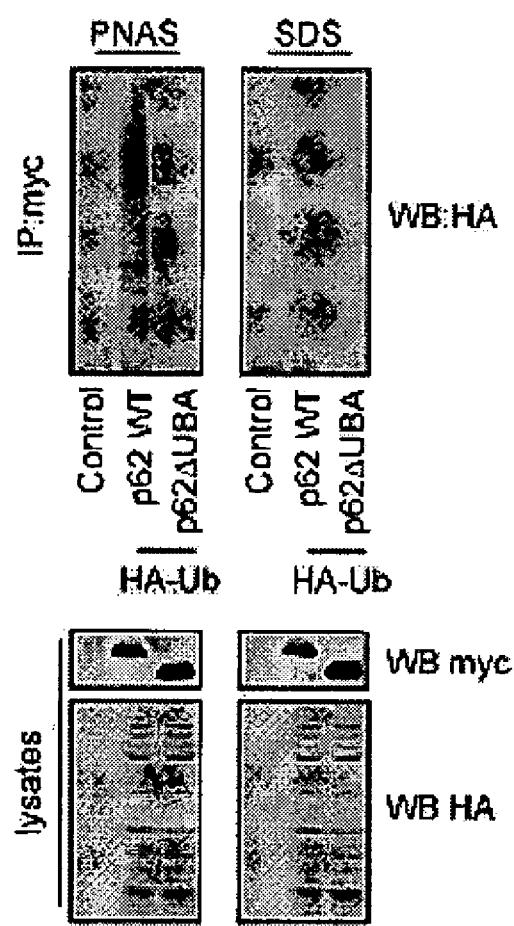
FIG. 1B shows a panel of immunoblots indicating that the UBA domain is necessary for p62 to interact with polyubiquitin.

UBA Domain Binds Polyubiquitin Noncovalently and is Required for Aggregate Formation Three tagged constructs were employed (FIG. 1A) and are as follows: (i) the full-length p62; (ii) p62ΔN-term, a construct missing amino acids 1 to 229; and (ii) p62ΔUBA, a construct missing the UBA domain at ammo acids 386 to 440. To establish the relationship between UBA polyubiquitin binding and aggregate formation, p62 binding to polyubiquitin in vivo was assessed. Full-length p62 or a mutant lacking the UBA domain was coexpressed with HA-tagged ubiquitin in HEK cells (FIG. 1B). Lysis and immunoprecipitation (IP) were carried out in either PNAS buffer (lacking SDS) or SDS lysis buffer (SDS) followed by SDS-PAGE and Western blotting (WB) for HA-tagged ubiquitin (FIG. 1B). The data show that the UBA domain is necessary for p62 to interact with polyubiquitin. The coimmunoprecipitated ubiquitin (HA) signal was not due to the covalent attachment of ubiquitin chains to p62 itself, because the signal was lost when the cells were lysed in an SDS-containing lysis buffer.

The UBA domain of p62 is required for polyubiquitin sequestration, whereas its N terminus was not (data not shown). In parallel p62 was able to sequester polyubiquitin in vivo. HEK cells were cotransfected with full-length p62, p62 lacking its UBA domain (p62ΔUBA), or a construct lacking its N terminus (p62ΔN-term) along with HA-tagged ubiquitin. The cotransfected cells were examined by confocal microscopy.

Figure 1C:
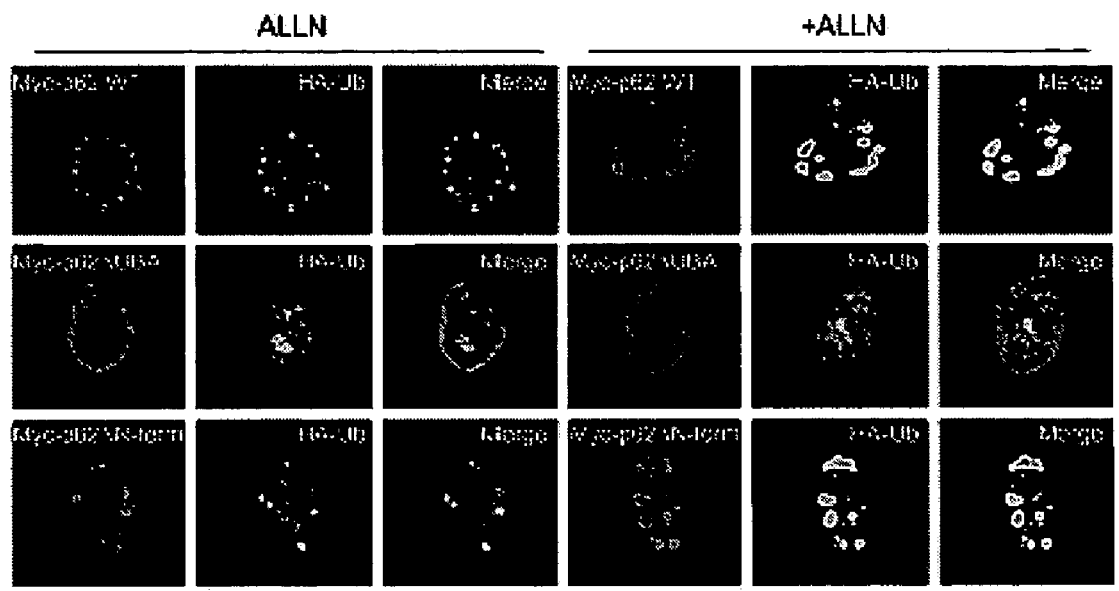
FIG. 1C is a panel of laser scanning confocal microscopy images of immunofluorescence staining for indicated p62 recombinant proteins.

FIG. 1C shows laser scanning confocal microscopy images of immunofluorescence staining for exogenous myc-p62 (red) and HA-ubiquitin (green) of wild-type myc-p62-expressing (top), myc-p62ΔUBA-expressing (middle), and myc-p62ΔN-term-expressing (bottom) HEK cells with (+) or without (−) proteasomal inhibitor ALLN (50 µM) for 24 h. Cells were incubated with rabbit anti-myc IgG or mouse anti-HA IgG and labeled with Texas Red-conjugated anti-rabbit antibodies (red) or Oregon Green-conjugated anti-mouse antibodies (green), respectively. Merged images with overlapping immunoreactivity are shown in yellow. Note that cells expressing p62 lacking its UBA domain (p62ΔUBA) fail to form aggregates or to colocalize with ubiquitin. All experiments were replicated three independent times with similar results. Small aggregates of p62 colocalized with ubiquitin which was dependant upon the presence of a UBA domain but not the N-terminal portion of p62. Aggregation may impair the proteasome or, alternatively, impaired proteasome activity may seed aggregates. Alternatively, impairment of the proteasome may enhance the formation of p62 aggregates containing polyubiquitin.

Upon the inhibition of proteasomal degradation by treatment with ALLN (or MG132 [data not shown]), large aggregates of p62 which contained sequestered polyubiquitin were visible (FIG. 1C). The average number of aggregates per cell was essentially similar with or without ALLN; however, the size of the aggregates increased from 6 to 8 microns to 12 to 14 microns upon treatment with ALLN. Additionally, the formation of the p62 aggregates was dependent upon microtubules since treatment with either vinblastine or nocodazole prevented their formation (data not shown). In summary, through its UBA domain, p62 Interacts with polyubiquitinated substrates, and the UBA domain is necessary for aggregate formation.

Example 2

Aggregates Compromise Cell Survival

The role of aggregates and their relationship to cell survival are controversial. It has been suggested that aggregates represent the cell's attempt to rid itself of misfolded proteins, and hence, cells possessing aggregates represent a population of cells that are surviving, whereas cells without, aggregates represent, dying cells, although these observations may be condition and/or cell type specific. Since cells transfected with p62 lacking a UBA domain failed to form aggregates, this system provided a means to address the role of aggregate formation in relation to cell survival. Viability of cells with p62 aggregates employing the Live/Dead Viability/Cytotoxicity assay was determined (Table 1).

TABLE 1

Relationship of p62 aggregates to cell survival

| | % of cells | | | |
|---|---|---|---|---|
| | With aggregates | | Without aggregates | |
| Treatment | Dead | Alive | Dead | Alive |
| Without ALLN | 39 | 61 | 65 | 35 |
| With ALLN | 52 | 48 | 62 | 38 |

Cells were scored as aggregate positive or negative based upon the expression of GFP-p62. Cells were scored as dead or alive employing either the green or red stain (Molecular Probes).

Figure 1D:
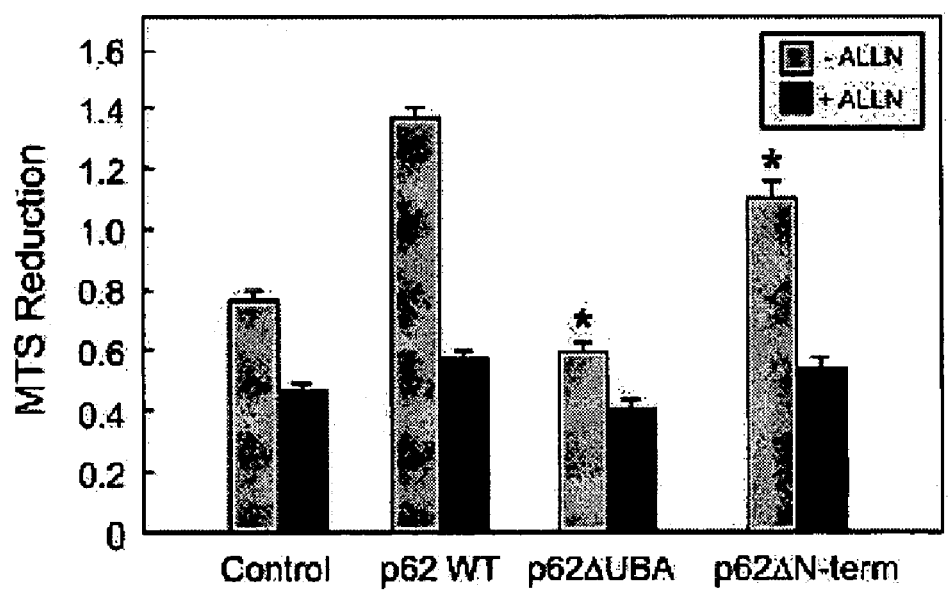
FIG. 1D is a bar graph showing survival of cells expressing the indicated p62 constructs.

In cells lacking aggregates, there was essentially no difference in the survival profile in the presence or absence of ALLN treatment. Aggregate-containing cells. Compared to those without aggregates. However, ALLN treatment decreased the number of living cells. The data indicate that aggregates are a characteristic of living cells; however, proteasomal inhibition drives aggregate-containing cells away from survival. On the population level, similar results were observed when the MTS assay was used (FIG. 1D). Deletion of the UBA domain blocked the survival-promoting effects of p62. By comparison, deletion of the N-terminal region of p62 had less drastic effects on cell survival. Induction of p62 aggregates by treatment with ALLN completely inhibited the cell survival-promoting effects of p62 (FIG. 1D).

In FIG. 1D HEK cells (in a 24-well plate) were transfected with myc-tagged wild-type p62, p62ΔUBA, or p62ΔN-term along with HA-tagged ubiquitin constructs. After 24 h of transfection, the cells were treated with or without ALLN (50 µM) for 30 h. Cell survival was assessed by the addition of MTS reagent for 2 h. Values plotted in FIG. 1D are means±standard error of the means of four different experiments. Survival was significantly diminished between the control and p62ΔUBA ($P<0.001$) and between wild-type p62 and p62ΔN-term ($P<0.001$).

Example 3 p62 Interacts with K63-Polyubiquitnated Substrates Through its UBA Domain

Polyubiquitin chains may be formed in vivo by three linkages within ubiquitin: K29, K48, and K63. Since each type chain may assume a different conformation, it has been suggested that each UBA domain may possess chain-specific recognition capabilities. To test the type of polyubiquitin chain recognized by the UBA domain of p62, HEK cells were transfected either with HA-tagged wild-type ubiquitin (IIA-Ub) or K29R, K48R, or K63R point, mutants of ubiquitin or with HA-tagged wild-type ubiquitin or K63R, K29,48R, or K29,48,63R mutants of ubiquitin. An equal protein concentration of cell lysate was interacted with the UBA domain of p62 in a pull-down assay. Binding of polyubiquitin chains was determined by Western blot, analysis with HA antibody to detect ubiquitin (WB:HA). The expression of ubiquitin constructs was verified by blotting an aliquot of the transfected cell lysate (40 µg) with HA tag antibody.

Figure 2A:
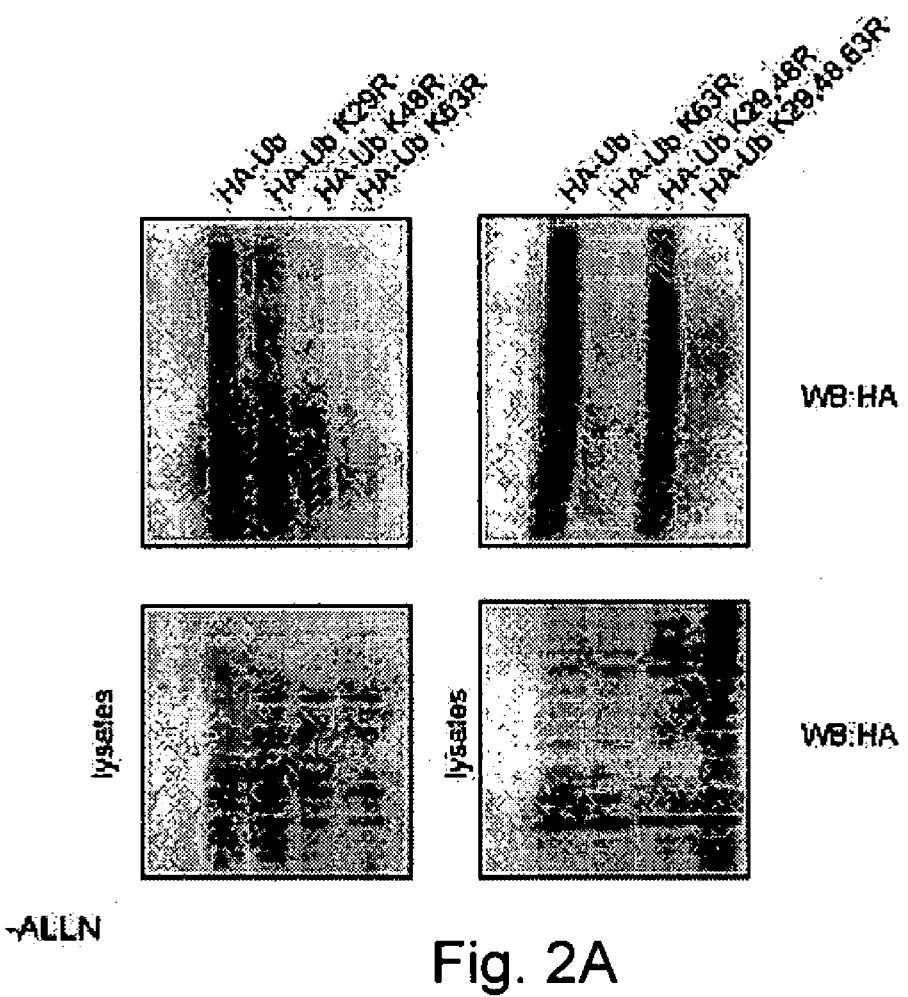
FIG. 2A is a panel of immunoblots using indicated ubiquitin constructs.

As shown in FIG. 2A, the UBA domain of p62 interacted with HA-tagged polyubiquitin chains. However, when K63 of ubiquitin was mutated to arginine (R), the ability of polyubiquitin to bind the UBA domain of p62 was completely inhibited, whereas binding was retained when either K29 or K48 was mutated to R. Although present, K48R chain interaction was somewhat diminished upon, mutation; however, this observation did not hold up in subsequent characterization studies (FIG. 2A, right top panel). In parallel interaction of the UBA domain of p62 with lysates prepared from cells expressing wild-type ubiquitin, K63R (lacking any K63-polyubiquitin chains), K29,48R (where the predominant pool of polyubiquitin expressed would be K63) or the triple mutant K29,48,63R (absence of the major polyubiquitin chains) was investigated. Binding to the UBA domain of p62 was observed only with lysates from cells expressing HA-tagged wild-type ubiquitin or K29,48R (FIG. 2A). As a control, the addition of increasing concentrations of K48 chains into the binding assay failed to compete for binding with K29,48R polyubiquitinated substrates (data not shown). The UBA domain of p62 also directly bound in vitro synthesized K63-polyubiquitin chains.

To assess the specificity of the p62 UBA pull-down assay at discriminating chain-specific interactions, the ability of hPLIC-2, a polyubiquitin-binding protein whose UBA domain chain-binding properties have not yet been characterized, to bind polyubiquitinated substrates was determined. Lysates prepared from cells expressing HA-tagged ubiquitin constructs revealed that the UBA domain of hPLIC-2 bound proteins with K48 chains but not those of K63 (data not shown). Collectively, these findings indicate that, the UBA domain of p62 binds proteins with K63-linked polyubiquitin chains.

Figure 2B:
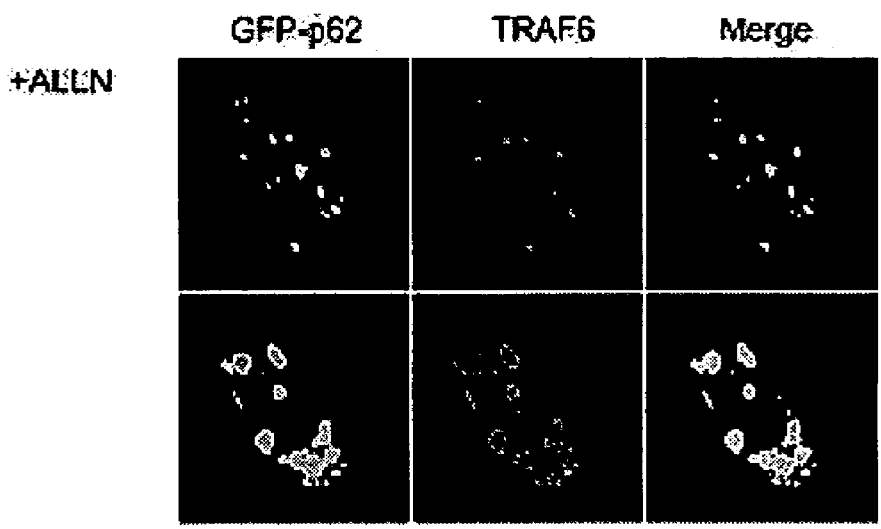
FIG. 2B is fluorescence micrographs of HEK cells transfected with GFP-p62.

To determine whether TRAF6 may become trapped along with p62 and ubiquitin within the large aggregates upon inhibition of the proteasome, the colocalization of TRAF6 with p62 was examined in the absence or presence of proteasomal inhibition (FIG. 2B). The smaller punctate p62 aggregates possessed colocalized TRAF6, revealing that these structures likely serve as a microenvironment for TRAF6-p62 signaling. The larger insoluble aggregates formed upon inhibition of the proteasome likewise accumulated large amounts of TRAF6 (FIG. 2B), which were shown to colocalize with polyubiquitin (FIG. 1C).

Since p62 possesses a binding site for TRAF6, a RING finger E3 ubiquitin ligase, TRAF6 may become trapped along with p62 and ubiquitin within the large aggregates upon inhibition of the proteasome. To test this idea, the colocalization of TRAF6 with p62 was examined in the absence or presence of proteasomal inhibition (FIG. 2B). The smaller punctate p62 aggregates possessed colocalized TRAF6, revealing that these structures likely serve as a microenvironment for TRAF6-p62 signaling. The larger insoluble aggregates formed upon inhibition of the proteasome likewise accumulated large amounts of TRAF6 (FIG. 2B), which were shown to colocalize with polyubiquitin (FIG. 1C).

Figure 2C:
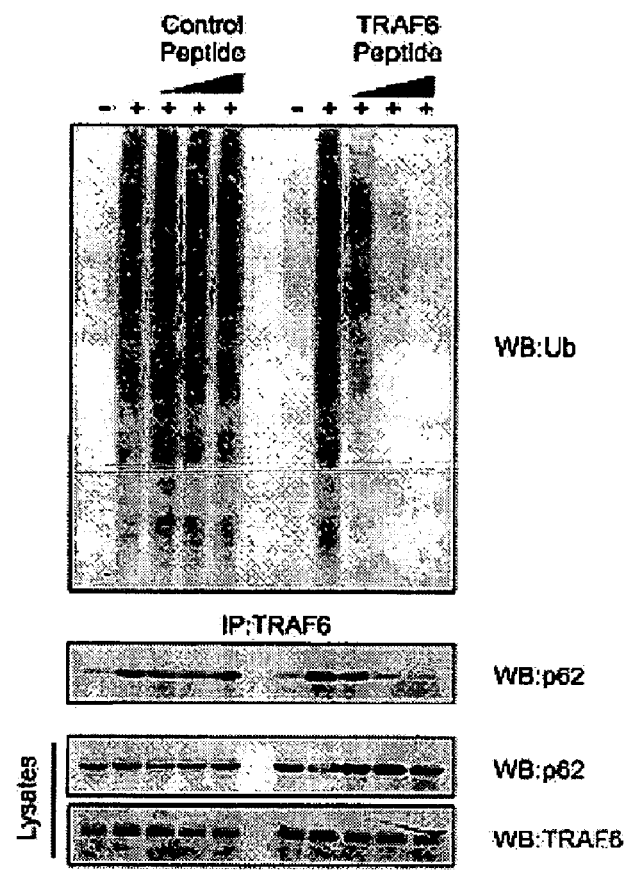
FIG. 2C shows a panel of immunoblots of HEK cells pretreated with TRAF6 inhibitory peptide.

As an E3 ligase, TRAF6 has been shown to selectively synthesize K63-polyubiquitin chains onto target substrates. p62 possesses a TRAF6-binding motif, and recent studies have shown that peptides homologous to this motif may competitively inhibit TRAF6 signaling or function. A peptide (plain type, SEQ ID NO. 6) containing the TRAF6-binding motif present in p62 (underlined type) along with the hydrophobic sequence containing the cell-permeable motif (italicized type) from Kaposi fibroblast growth factor signal sequence was synthesized (AAVALLPAVLLALLAP-ES-ASGPSEDPSVNFLK) (SEQ ID NO. 4) or a control peptide with mutant amino acids in the interaction motif (AAVA LLPAVLLALLAP-ESASGASADASVNFLK)(SEQ ID NO. 5). These studies reveal that the cell-permeable TRAF6 inhibitory peptide blocked p62-TRAF6 interaction in a dose-dependent fashion (FIG. 2C). HEK cells were treated or not with increasing doses of control or TRAF6 inhibitory peptide, followed by stimulation with IL-1. Lysates were prepared and included in a pull-down employing the UBA domain of p62. Should the p62-UBA domain bind K63-polyubiquitinated substrate proteins, a dose-dependent reduction in interaction of the lysates would occur with lysates prepared from cells pretreated with TRAF6 inhibitory peptide. In fact, this is what was found (FIG. 2C).

Figure 2D:
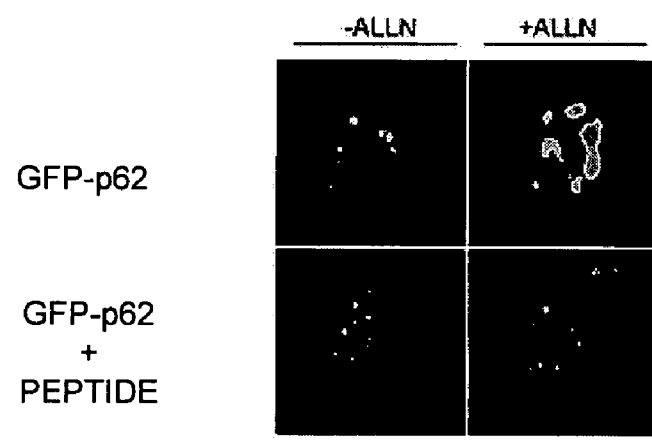
FIG. 2D is a panel of fluorescence micrographs of HEK cells transfected with GFP-p62 and treated with TRAF6 inhibitory peptide and ALLN.

Since TRAF6 localized to the large aggregates along with polyubiquitin (FIG. 2B), these aggregates may represent the failed attempt of the cell to rid itself of TRAF6-K63-polyubiquitinated substrates sequestered through interaction with the UBA domain. Hence, inhibition of TRAF6 interaction with p62 might prevent the formation of the aggregates. Pretreatment of cells with an inhibitory dose of TRAF6 peptide (but not control peptide [data not shown]) prior to treatment with ALLN resulted in a decrease in the size of the p62 aggregates (FIG. 2D). ALLN treatment caused 100% of the GFP-p62-expressing cells to accumulate large p62 aggregates. By comparison, treatment with TRAF6 peptide resulted in a 60% reduction in the formation of large aggregates. Altogether, these findings reveal that p62 binds proteins with K63 chains through its UBA domain and that p62 aggregates sequester TRAF6 as well as K63-polyubiquitinated substrates.

Example 3

Determinants of p62-Polyubiquitm Interaction and Aggregate Formation

Figure 3A:
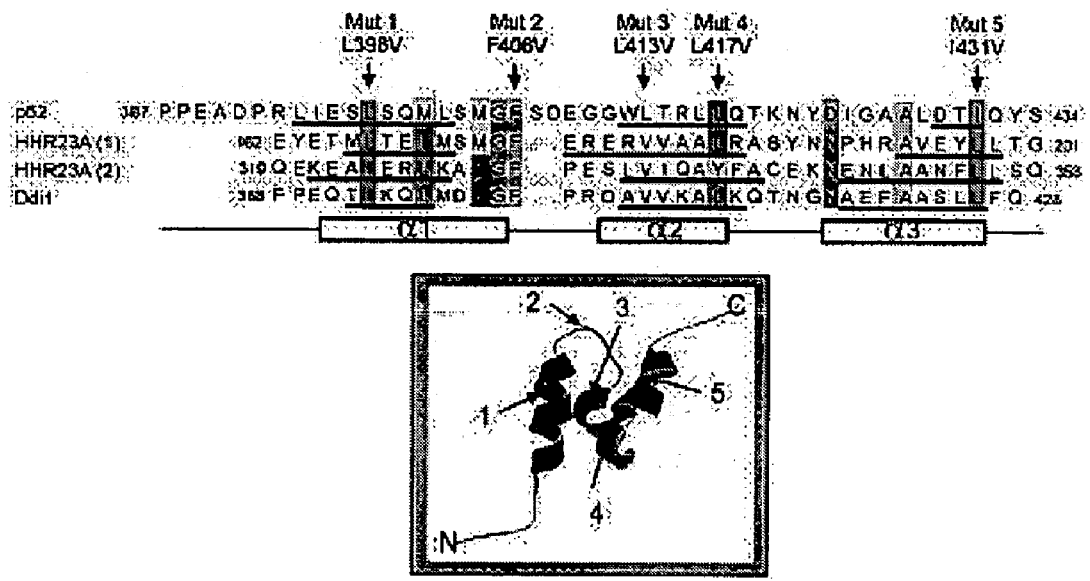
FIG. 3A shows the sequence alignment of UBA domains of p62 with other UBA containing proteins.

A series of mutations (L398V and F406V [helix 1], L413V and L417V [helix 2], and 1431V [helix 3]) within the p62 UBA domain were made (FIG. 3A) to assess residues that may be important for the structural integrity of the UBA domain and to determine which residues are necessary for polyubiquitin binding. FIG. 3A shows the sequence alignment of the UBA domain of p62 with UBA containing proteins hHR23A UBA1, hHR23A UBA2, and Ddi1, indicating conserved residues and a-helix formation. Arrows indicate residues mutated for analysis as well as their location on a three-dimensional model of the p62 UBA domain. In parallel, studies were undertaken to determine the effects that mutations in the UBA domain had upon the localization of p62 within aggregates and the ability of p62 to sequester polyubiquitin in vivo.

Figure 3B:
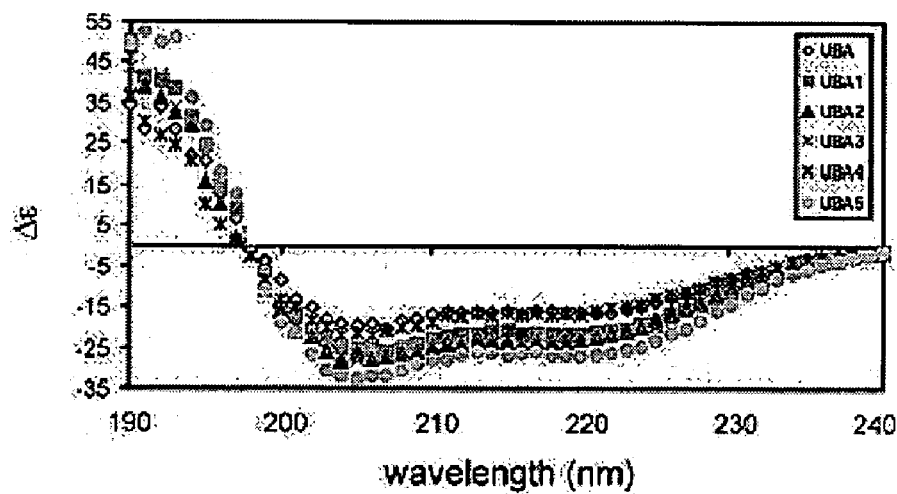
FIG. 3B shows circular dichroism spectra of UBA peptides.

As a means to explore the consequences which each mutation had on perturbation of the secondary structure within the UBA domain, wild-type p62 and the five UBA domain mutants were analyzed with CD spectroscopy. Since the UBA domain consists of three a-helical structures, the peptide from this domain was well suited for CD analysis. The CD spectrum of wild-type UBA has a band at 207 nm with $\Delta\epsilon_{max}$ equal to $-20.38$ $M^{-1}$ $cm^{-1}$ and a band at 220 nm with $\Delta\epsilon_{max}$ equal to $-16.59$ $M^{-1}$ $cm^{-1}$. This pattern is typical for proteins rich in helical content. The CD spectra of the mutants showed only small deviations from the wild-type UBA domain (FIG. 3B), indicating that the secondary structure of the mutants was not significantly perturbed. Consistent with this observation, secondary structural analyses of the experimental CD data using CDSSTR and CONTIN/LL programs resulted in essentially similar secondary structural contents for all the peptides (Table 2). Fits between the experimental CD data and the calculated data are good, with a root mean squared deviation, in the range of 0.9 to 1.6.

TABLE 2

Estimation of secondary structures in UBA peptides based on CD data

| Protein | Method of data analysis and average[b] | % of peptides with the following secondary structures[a] | | | | | |
|---|---|---|---|---|---|---|---|
| | | $H_r$ | $H_d$ | $B_r$ | $B_d$ | Turn | Coil |
| | CDSSTR | 52.2 | 15.3 | 3.6 | 7.6 | 4.4 | 16.7 |
| | CONTIN/LL | 51.0 | 18.6 | 0.0 | 2.1 | 5.3 | 23.1 |
| | Average | 51.6 | 17.0 | 1.8 | 4.9 | 4.9 | 19.9 |
| UBA1 | CDSSTR | 54.8 | 14.7 | 2.7 | 8.0 | 3.4 | 16.7 |
| | CONTIN/LL | 56.6 | 17.2 | 0.0 | 2.5 | 4.0 | 19.8 |
| | Average | 55.7 | 16.0 | 1.4 | 5.3 | 3.7 | 18.3 |
| UBA2 | CDSSTR | 48.4 | 12.5 | 6.1 | 10.5 | 3.3 | 19.1 |
| | CONTIN/LL | 49.6 | 11.9 | 0.0 | 3.0 | 7.8 | 27.8 |
| | Average | 49.0 | 12.2 | 3.1 | 6.8 | 5.6 | 23.5 |
| UBA3 | CDSSTR | 49.8 | 13.8 | 6.2 | 8.9 | 5.7 | 16.4 |
| | CONTIN/LL | 51.3 | 16.7 | 0.0 | 3.4 | 6.0 | 22.8 |
| | Average | 50.6 | 15.3 | 3.1 | 6.2 | 5.9 | 19.6 |
| UBA4 | CDSSTR | 53.6 | 14.0 | 4.6 | 8.6 | 3.5 | 15.4 |
| | CONTIN/LL | 43.8 | 11.9 | 0.0 | 3.1 | 6.9 | 33.4 |
| | Average | 48.7 | 13.0 | 2.3 | 5.9 | 5.2 | 24.4 |
| UBA5 | CDSSTR | 50.5 | 15.0 | 3.9 | 6.9 | 4.2 | 1.9.5 |
| | CONTIN/LL | 56.7 | 16.7 | 0.0 | 3.7 | 4.0 | 19.0 |
| | Average | 53.6 | 15.9 | 2.0 | 5.3 | 4.1 | 19.3 |

[a]Abbreviations: $H_r$, regular α-helix; $H_d$, distorted α-helix (number of amino acids equal to or less than 4); $B_r$, regular β-strand; $B_d$, distorted β-strand (number of residues equal to or less than 2).
[b]The readings of CONTIN/LL are the averages of the results from the CONTIN and CONTINLL programs. Average, average of the results from CDSSTR and CONTIN/LL methods.

Figure 3C:
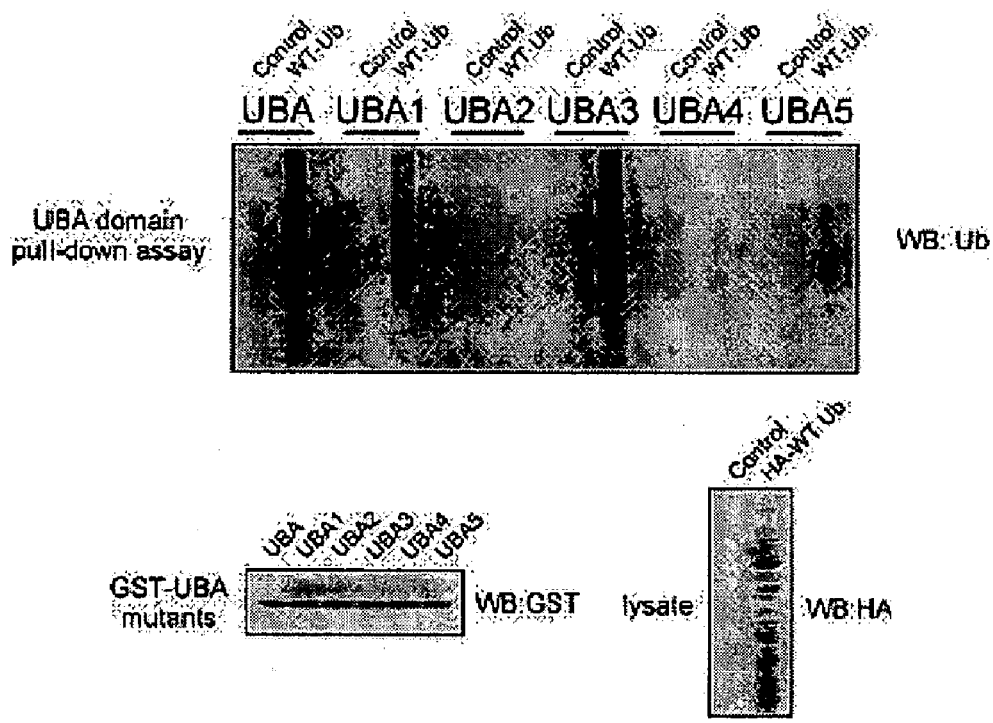
FIG. 3C shows an immunoblot of a UBA-domain pull-down assay.

The wild-type GST-p62 UBA domain along with the five UBA domain mutants were then employed in pull-down assays to assess their ability to interact, with polyubiquitinated proteins. HA-tagged polyubiquitin was expressed in HEK cells, and lysates were prepared and used as the source of polyubiquitinated substrates for a pull-down assay (FIG. 3C). The amount of the GST-tagged UBA domain mutants was equal in each pull-down, and the HA-lagged ubiquitin construct was effectively expressed. Mutant 2 (F406V) and mutant 4 (L417V) failed to bind polyubiquitin, with significantly reduced binding capacity exhibited by mutant 5 (I431V). Mutant 2 lies in the loop between helix 1 and helix 2 and is part of the MGF binding site while mutant 4 lies in helix 2, indicating that polyubiquitin binding is not conferred by a single site, but both hydrophobic surfaces within the UBA domain appear to serve as effective recognition surfaces for polyubiquitin binding. In the case of mutant 4, even though both leucine and valine have helix-forming potential, valine is weaker than leucine. Interestingly, the CD analysis shows that there is also a slight decrease (about 7%) in the total helical content for both mutants compared to that of the wild type (Table 2). Thus, the loss of interaction between polyubiquitin and the UBA domain might be due to a loss of some secondary structure.

Figure 4:
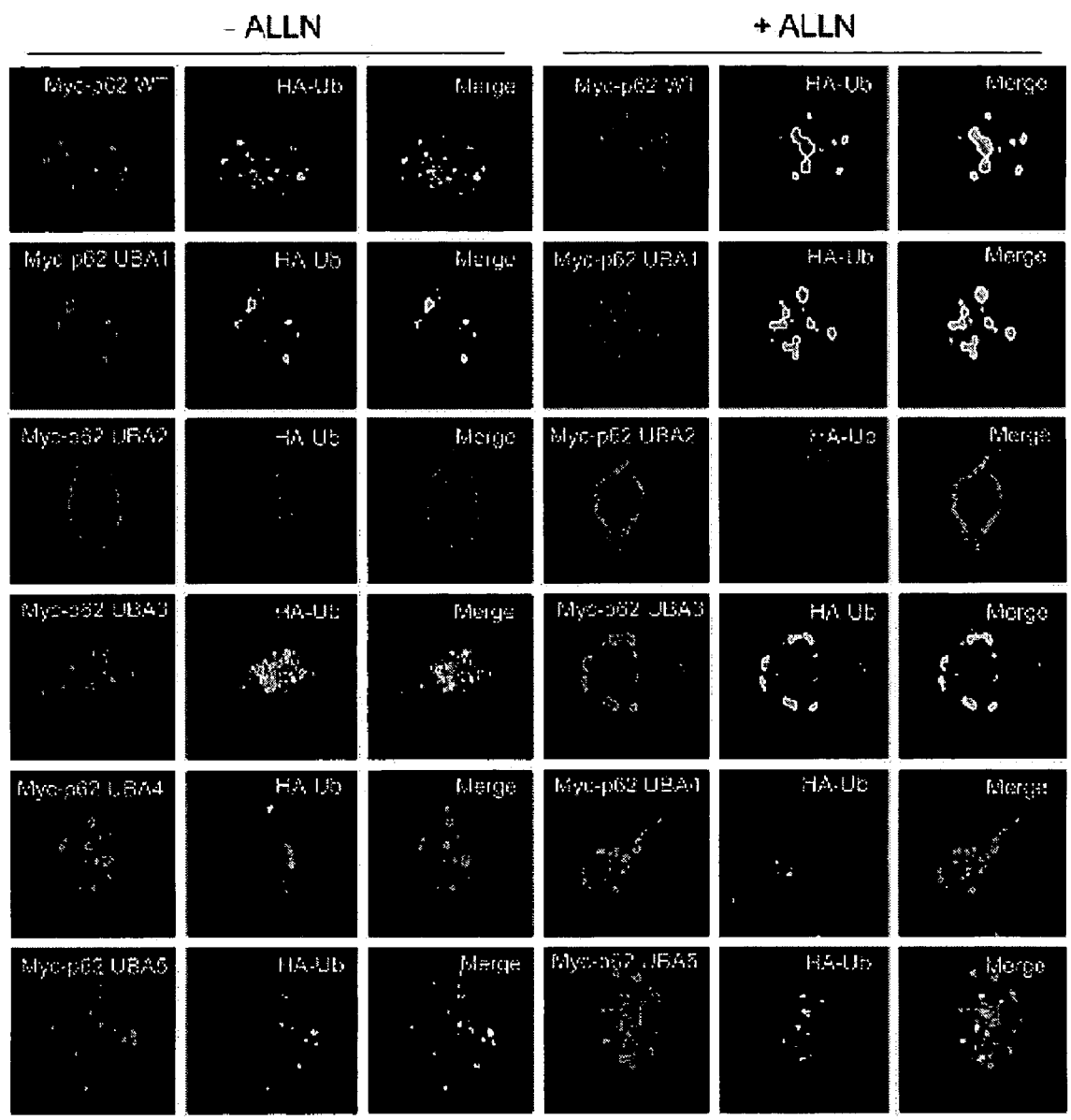
FIG. 4 shows a panel of immunofluorescence micrographs of HEK cells transfected with the indicated constructs.

Since the UBA domain is necessary for polyubiquitin binding and aggregate formation, the functional properties of the mutants could be assessed by examining their ability to sequester polyubiquitin along with the appearance of p62 within aggregates (FIG. 4). In FIG. 4 HEK cells were cotransfected with HA-tagged ubiquitin (HA-Ub) together with myc-tagged full-length and UBA mutants of p62 expression constructs treated with (+) or without (−) proteasomal inhibitor AL-LN (50 μM) for 24 h and then labeled with antibodies to HA and myc. Images of a representative cell are shown. Anti-myc labeling (red) detects wild-type (WT) myc-p62 and its UBA domain mutants. Anti-HA labeling (green) detects ubiquitin. Merged images show the overlap between the individual staining patterns as yellow. The findings are representative of two independent experiments.

Effects of the UBA mutations on aggregate formation, p62 targeting to aggregates, and polyubiquitin sequestration fell into several classes. Compared to wild-type p62, mutants 1 and 3 had no effect on aggregate formation and on sequestration of polyubiquitin (FIG. 4). This is consistent with the ability of mutants 1 and 3 to effectively interact with polyubiquitin (FIG. 3C). By comparison, mutation of the core MGF hydrophobic interaction patch (mutant 2) completely inhibited these effects (FIG. 4), as did mutation of the second hydrophobic patch located in helix 2 (mutant 4). Interestingly, the inability of both mutant 2 and 4 to bind polyubiquitin in vitro (FIG. 3C) was confirmed in vivo by the lack of polyubiquitin sequestration with these two mutants. Mutant 5 was able to sequester polyubiquitin to a degree but failed to form large aggregates upon inhibition of the proteasome with ALLN (FIG. 4). The lack of large aggregate formation with mutant 5 is likely due to its diminished interaction with polyubiquitin chains (FIG. 3C). Collectively, these findings (FIG. 4) are consistent with the results obtained with the in vitro pull-down assay (FIG. 3C) and further support the hypothesis that, large aggregates in proteasome-impaired cells result as a consequence of sequestration of K63-polyubiquitin substrates by the UBA domain of p62.

Example 4

P62 is Involved in Ubiquitintion

Figure 5A:
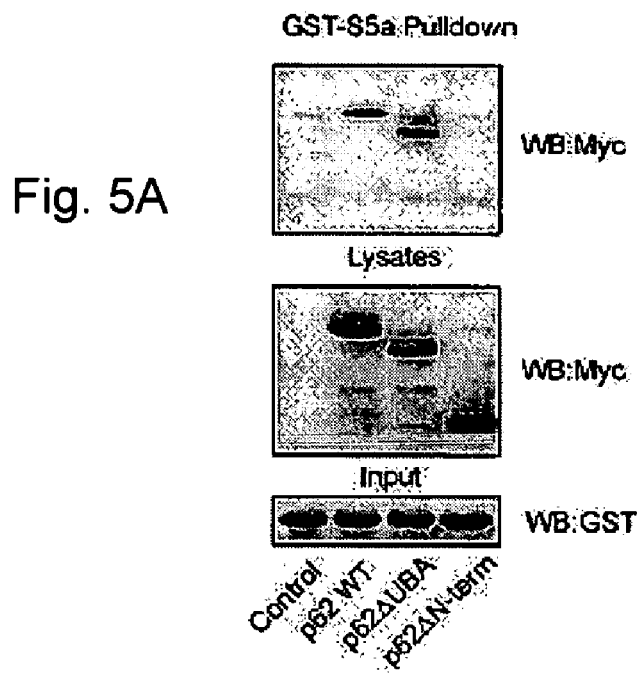
FIG. 5A shows a panel of immunoblots of a GST-S5a pull-down assay.
Figure 5B:
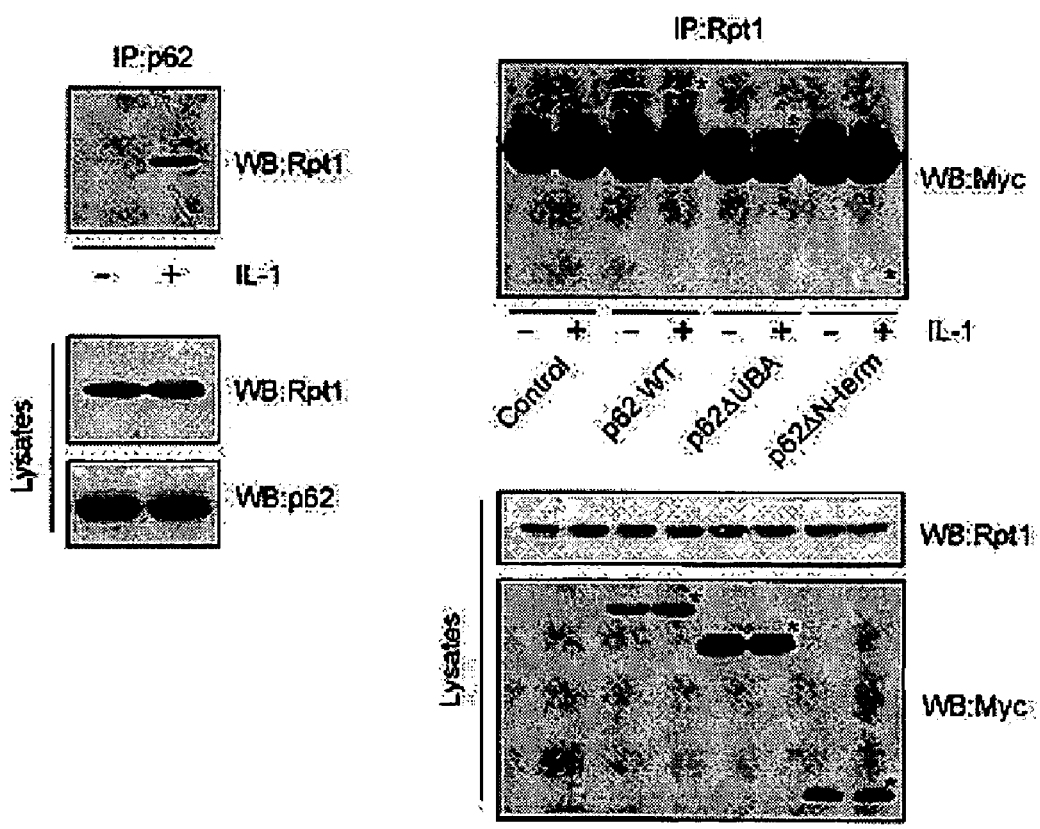
FIG. 5B is a panel of immunoblots of an anti-p62 immunoprecipitated cell lysates stimulated or not with IL-2.

Since aggregates have been reported to contain proteasomal components, it is possible that p62 may interact with the proteasome and be involved in the shuttling of substrates for degradation. To test this idea and to map the domain that might be involved in mediating this interaction, full-length p62. p62ΔN-term, and p62ΔUBA were transfected into HEK cells and lysates were prepared and used for interaction with GST-S5a (FIG. 5A). Full-length p62 or the p62 construct missing the UBA domain counteracted with S5a, whereas the N-terminal construct lacking the PB1 domain failed to interact with S5a. The PB1 domain within amino acids 1 to 229 enables p62 to interact with S5a, a subunit component of the hinge of the 19S proteasomal particle. This interaction may be indirect; therefore, additional experiments were undertaken to examine the ability of p62 to interact with the proteasome. p62 coprecipitated Rpt1 in a stimulus-dependent fashion (FIG. 5B, left). Alternatively, myc-tagged p62 constructs were transfected into HEK cells and the interaction of Rpt1 and p62 was mapped. Full-length p62 or p62 ΔUBA interacted with Rpt1, whereas p62ΔN-term did not (FIG. 5B, right). Thus, the p62 N terminus directs interaction with the proteasome.

Figure 5C:
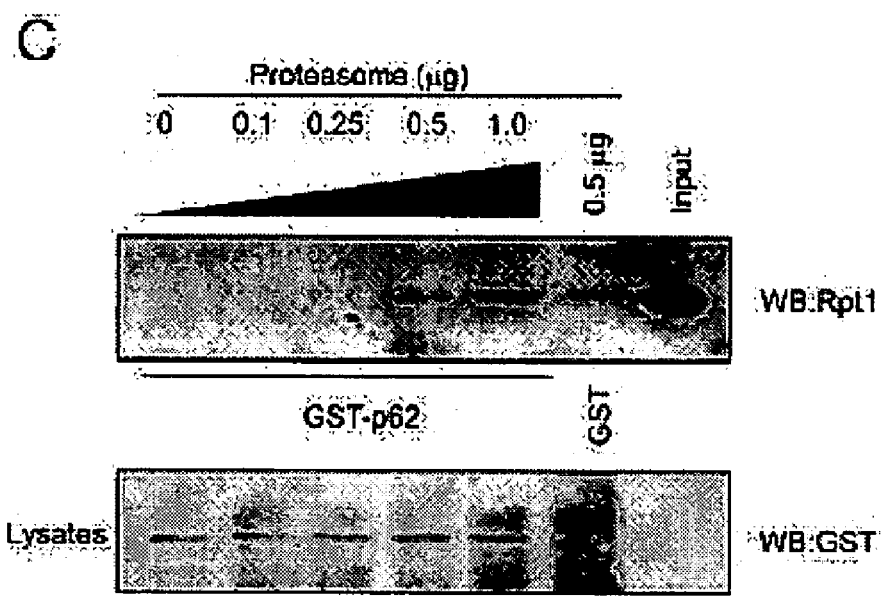
FIG. 5C shows a panel of immunoblots of GST-p62 showing p62 interacts directly with the proteasome.
Figure 5D:
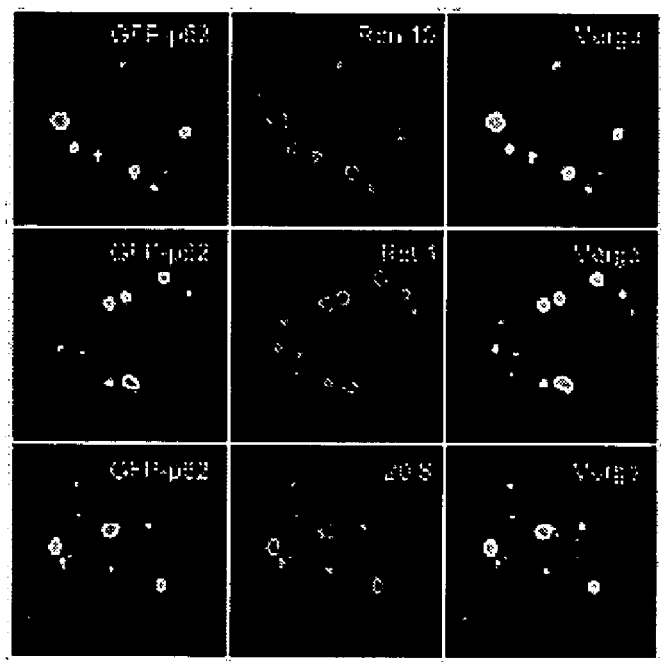
FIG. 5D is a panel of fluorescence micrographs showing p62 aggregates contain proteasomal subunits.

GST-p62 was able to directly interact with the proteasome as indicated by the pull-down of Rpt1 (FIG. 5C). Alternatively, GFP-p62-transfected cells treated with ALLN were costained with antibody to either Rpn10/S5a or Rpt1 or with antibody to the "core" subunits of the 20S particle (FIG. 5D) to establish colocalization of p62 with the proteasome. Staining with any of the three antibodies resulted in colocalization with p62, whereas staining with LAMP-1, a lysosomal marker, failed to colocalize with p62 (data not shown).

Figure 6A:
FIG. 6A is an immunoblot showing down-regulation of p62 with antisense nucleic acids.
Figure 6B:
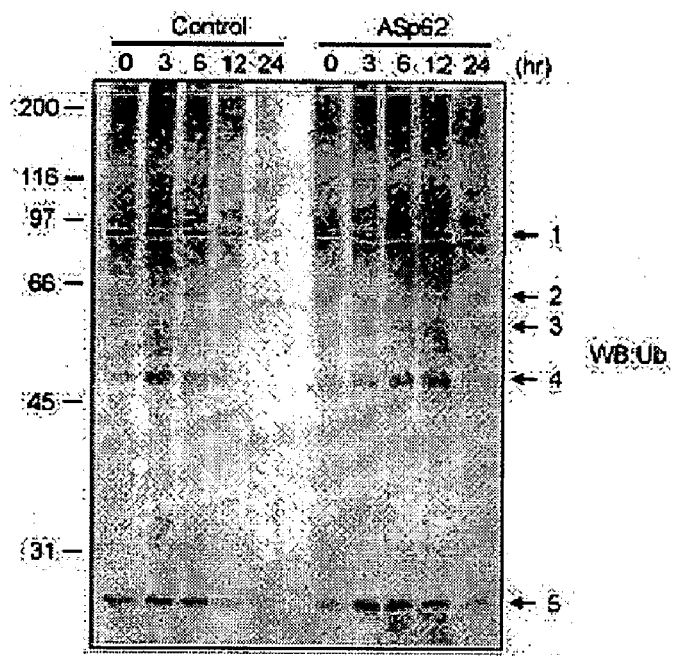
FIG. 6B shows an immunoblot of control or antisense p62-transfected HEK cells treated with 20 mg of cycloheximide/ml as indicated.
Figure 6C:
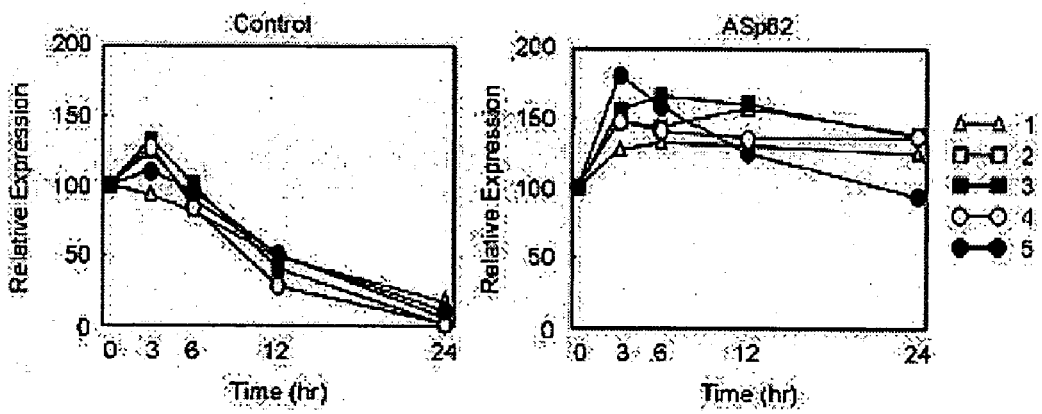
FIG. 6C shows a panel of line graphs indicating relative expression of five prominent polyubiquitinated proteins present in both control and antisense p62.

Since p62 captures polyubiquitinated substrates through its UBA domain and interacts with the proteasome through its N terminus, p62 may be involved in the shuttling of polyubiquitinated substrates for degradation by the proteasome. The depletion of p62 levels might therefore result in inhibition of ubiquitin proteasome-mediated degradation and an accumulation of ubiquitinated proteins. HEK cells were transfected with a full-length antisense p62 construct which was followed by treatment of cells with cycloheximide to prevent protein synthesis and examine protein turnover. Transfection of the anti-sense p62 construct reduced endogenous p62 levels by 80% (FIG. 6A). Control cells rapidly turned over several substrates (FIG. 2B and C). By comparison of five prominent polyubiquitinated substrates, depletion of p62 levels resulted in the accumulation of these proteins. These findings reveal that p62 serves a newly described role in ubiquitin-mediated proleolysis and may serve as a shuttling factor in the delivery of polyubiquitinated substrates for proteasomal degradation.

Example 5

Inclusions Isolated from AD Brain Possess p62, TRAF6 and UbcH7

Figure 7A:
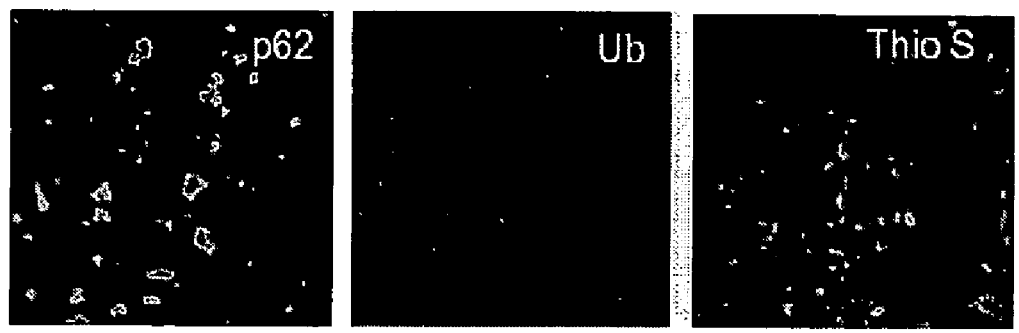
FIG. 7A shows confocal immunofluorescence images of AD inclusion bodies immunostained individually with antisera to p62, Ub, and thioflavin S.

Dual fluorescence labeling revealed that inclusions isolated from AD brain contain aggregates that double label with both p62 and ubiquitin (FIG. 7A). FIG. 7A shows confocal immunofluorescence images of AD inclusion bodies, immunostained individually with antisera to p62, Ub and thioflavin S. Both p62 and Ub which were visualized by secondary antibody to Texas red or Oregon green. In addition, these aggregates were positive for thioflavin S-staining, which detects proteins possessing beta pleated sheet structure.

Figure 7B:
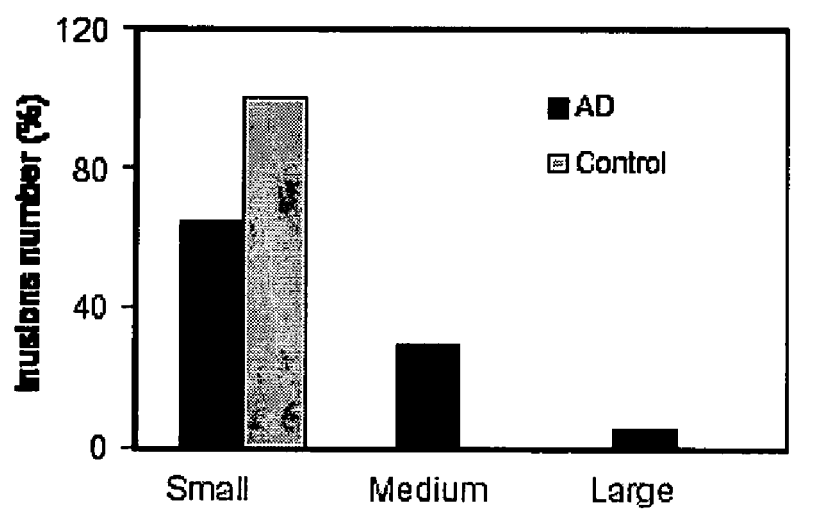
FIG. 7B shows a bar graph of the size of inclusion bodies in AD and distribution of inclusion size in AD.
Figure 7B:
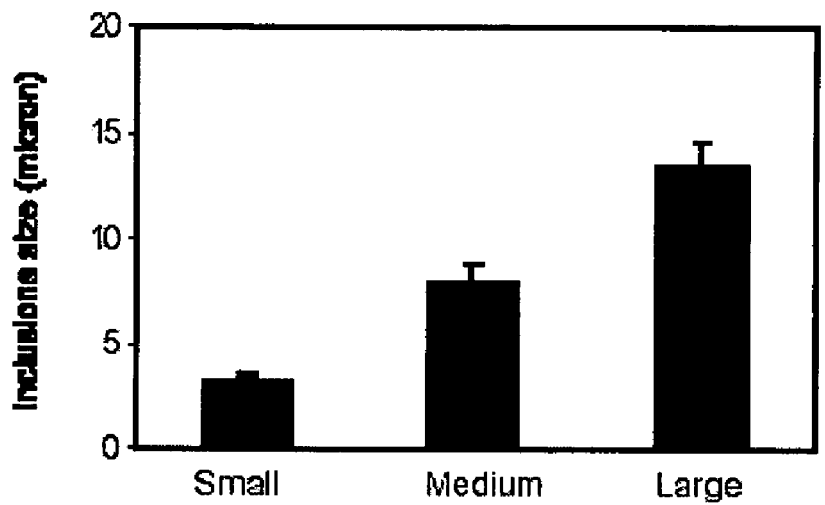
Figure 7C:
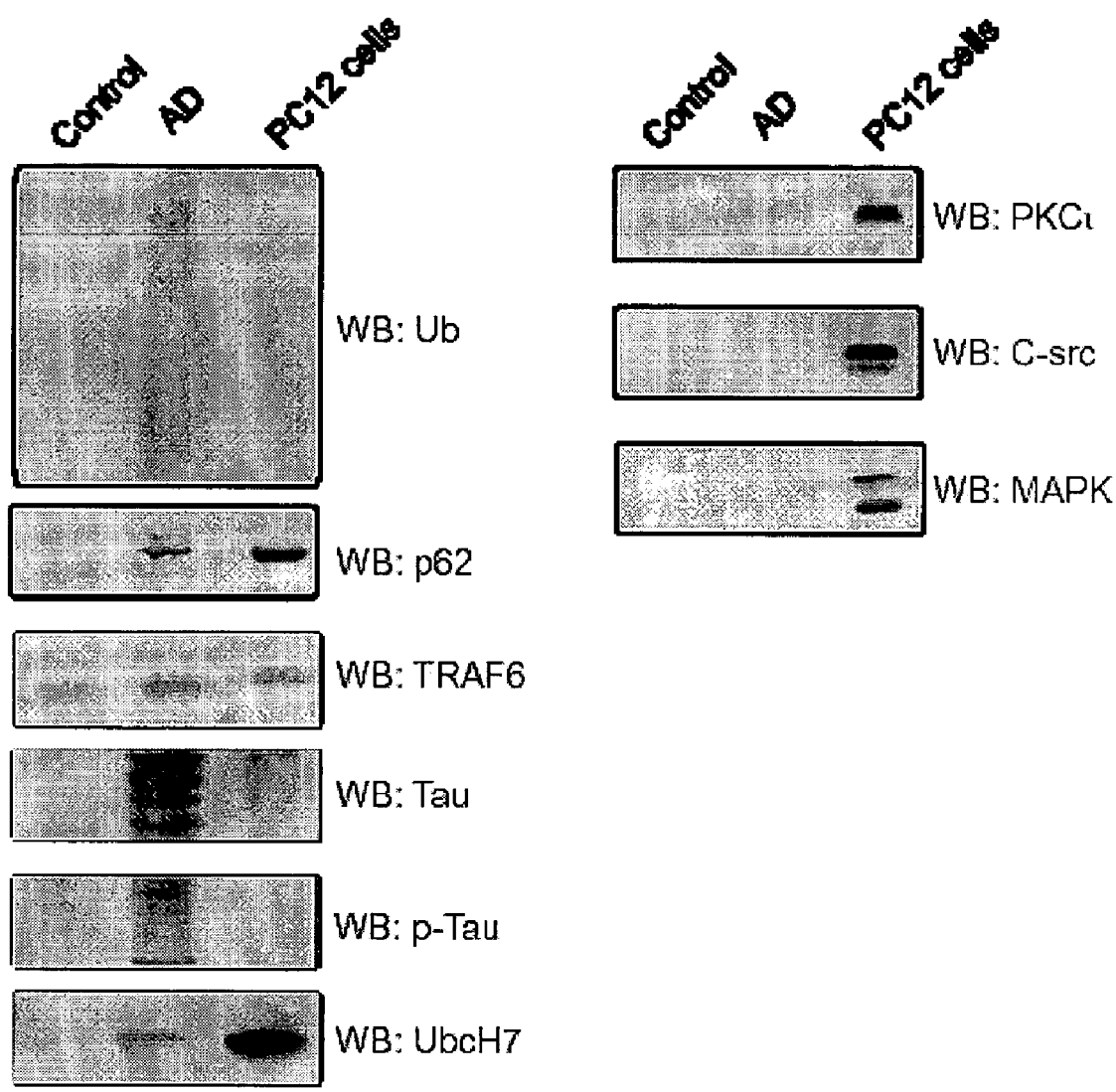
FIG. 7C shows a panel of immunoblots for the indicated proteins.

Using Metamorph, the heterogeneous nature of the preparation was quantitated (FIG. 7B). FIG. 7B shows the quantitative analysis of the inclusion bodies from both control and AD brain. Left—Three different sizes of inclusions were observed in AD samples. Right—Distribution of inclusion size in AD and control was determined. Twenty-five random fields were selected for counting for both AD and control inclusions. The inclusion preparation was predominantly composed of aggregates ranging in size from 12-15 microns. However, medium and smaller size aggregates were also present.

Inclusion preparation of samples obtained from normal aged-matched brain revealed an absence of the large/medium size aggregates, thus suggesting these may be a characteristic feature of AD brain. To further analyze the aggregates, their protein composition was analyzed by SDS-PAGE/western blot analysis (FIG. 1C) with various antibodies to proteins known to either coassociate with inclusions by immunohistochemistry (e.g. ubiquitin, tau, phosphorylated tau), or proteins known to interact with p62 directly (e.g. TRAF6, PKC iota), or with p62 indirectly (UbcHT through interaction with TRAF6, c-src through interaction with PKC iota or MAP kinase through interaction with PKC iota). C. Immunoblot analysis of the inclusion bodies from control individual, AD or PC12 cell lysates (antibody control). Equal concentration of protein (50 μg) from inclusions or PC12 cell lysates were loaded and separated by 12% SDS-PAGE and western blotted with antibody to ubiquitin, p62, TRAF6, tau, phospho-tau (12E8), UbcH7, PKC iota, c-src and MAPK as shown. Confirming the in situ immunofluorescence results, the inclusion preparation from AD brain possessed p62 and ubiquitin. In addition, TRAF6, tau, phosphorylated tau and UbcH7 were also present, whereas PKC iota, c-src and MAPK were absent. These findings reveal that specific proteins colocalize with p62 within the inclusion preparation.

Figure 8:
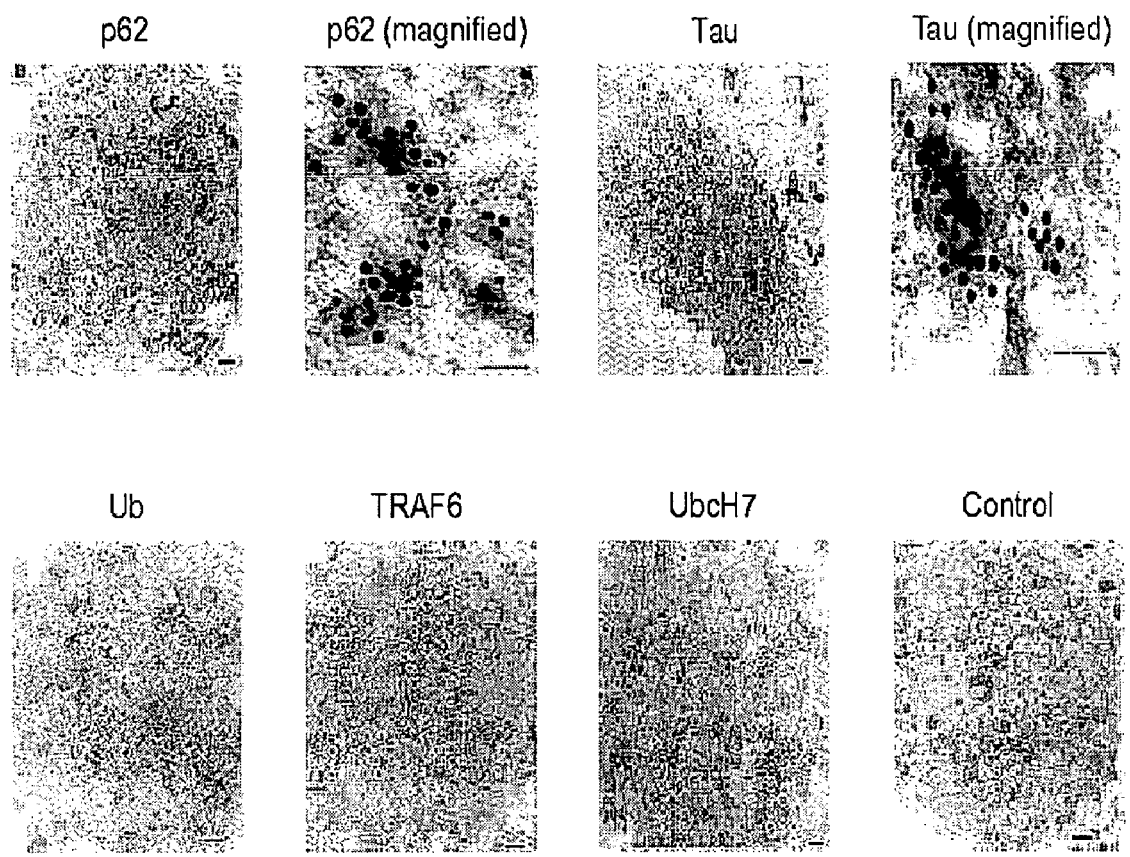
FIG. 8 shows a panel of electron micrographs of inclusion bodies isolated from AD brain.

The preparation was examined by immunoelectron microscopy (FIG. 8). The aggregates were irregular in shape and were filled with fibril structures. These aggregates stained with antibodies to p62, tau, ubiquitin, TRAF6 and UbcH7, whereas control sections without antibody did not possess any protein A binding.

Example 6

Colocalization of p62, Tau, Ubiquitin, TRAF6 and UbcH7 with Aggregates

Figure 9A:
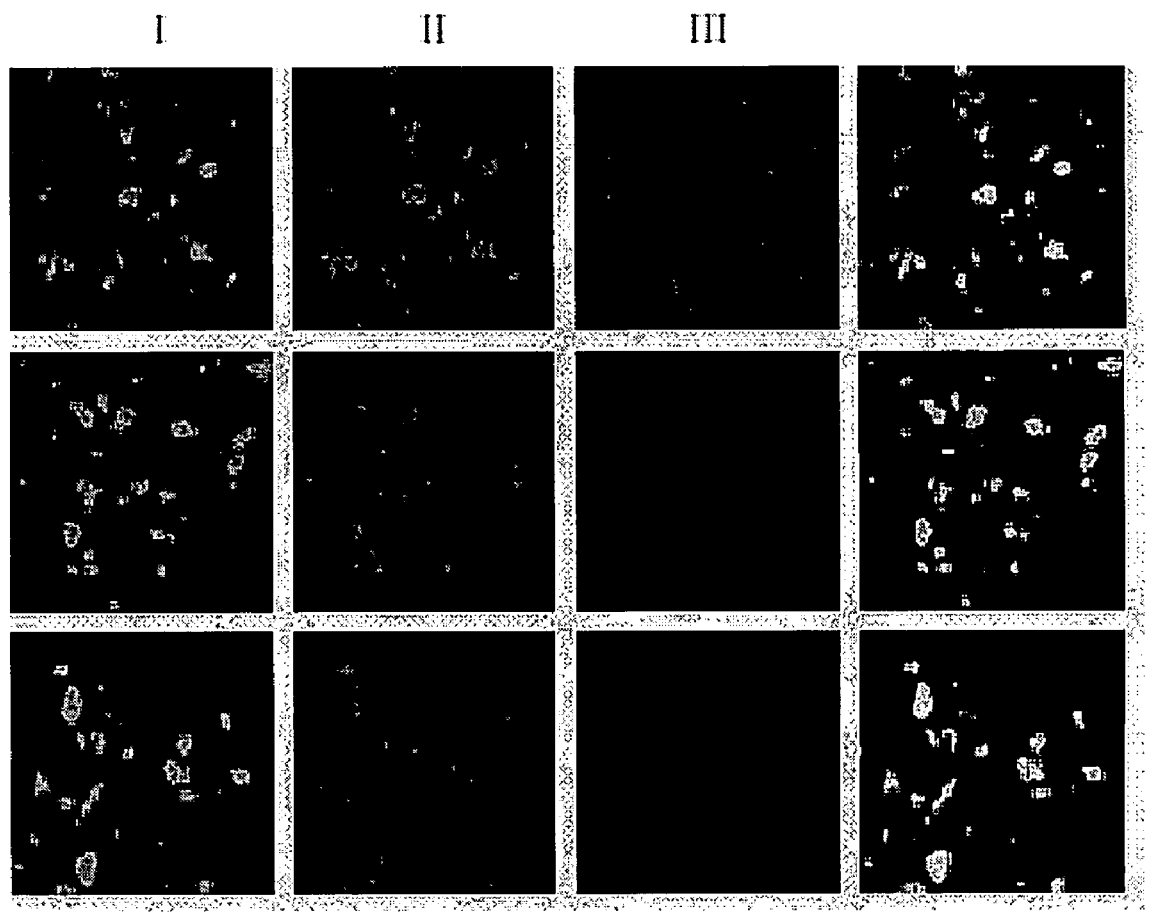
FIG. 9A shows triple immunofluorescence staining of inclusion bodies from AD patient's brain analyzed by using confocal microscopy.
Figure 9B:
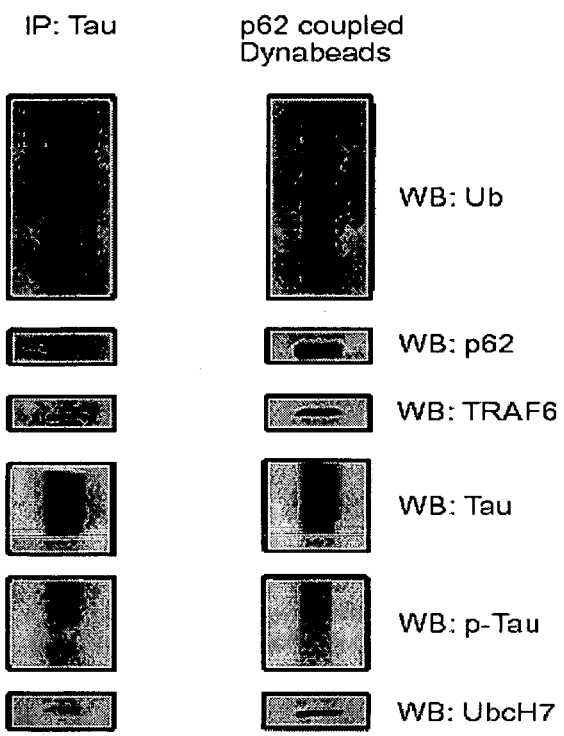
FIG. 9B shows a panel of immunoblots for the indicated proteins.

To investigate whether these proteins directly colocalized with aggregates, confocal immunofluorescent microscopy was undertaken (FIG. 9A). Colocalization of p62-tau-Ub, p62-tau-TRAF6, and UbcH7-tau-TRAF6 was observed. Employing a biochemical approach, immunoprecipitation of tau from the inclusion preparation revealed that ubiquitin, p62, TRAF6, tau, phosphorylated tau and UbcH7 likewise cointeracted (FIG. 9B, left). Alternatively, the inclusion preparation was further purified by immunomagentic affinity method, employing a p62 antibody. The proteins captured by p62-affinity purification of the inclusion preparation were the same as those captured by immunoprecipitation of tau from the aggregates (FIG. 9B, right compared to left).

Figure 9C:
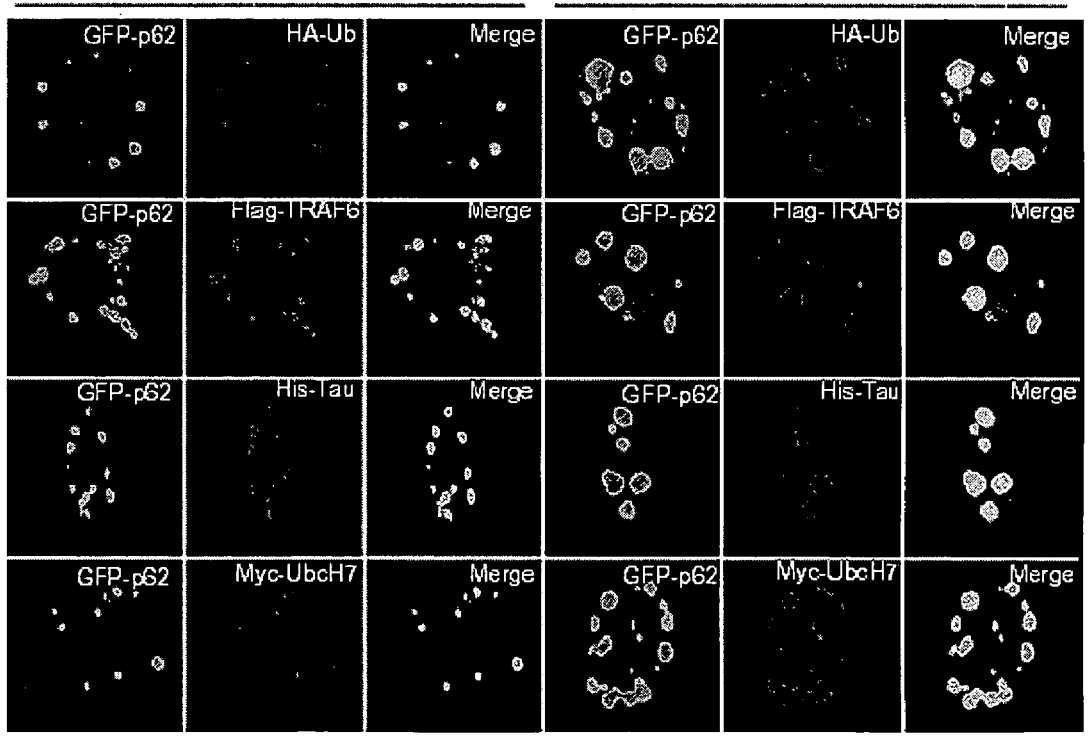
FIG. 9C shows images of cells visualized by confocal laser fluorescence microscopy after immunostaining with antibodies for the indicated proteins.
Figure 9D:
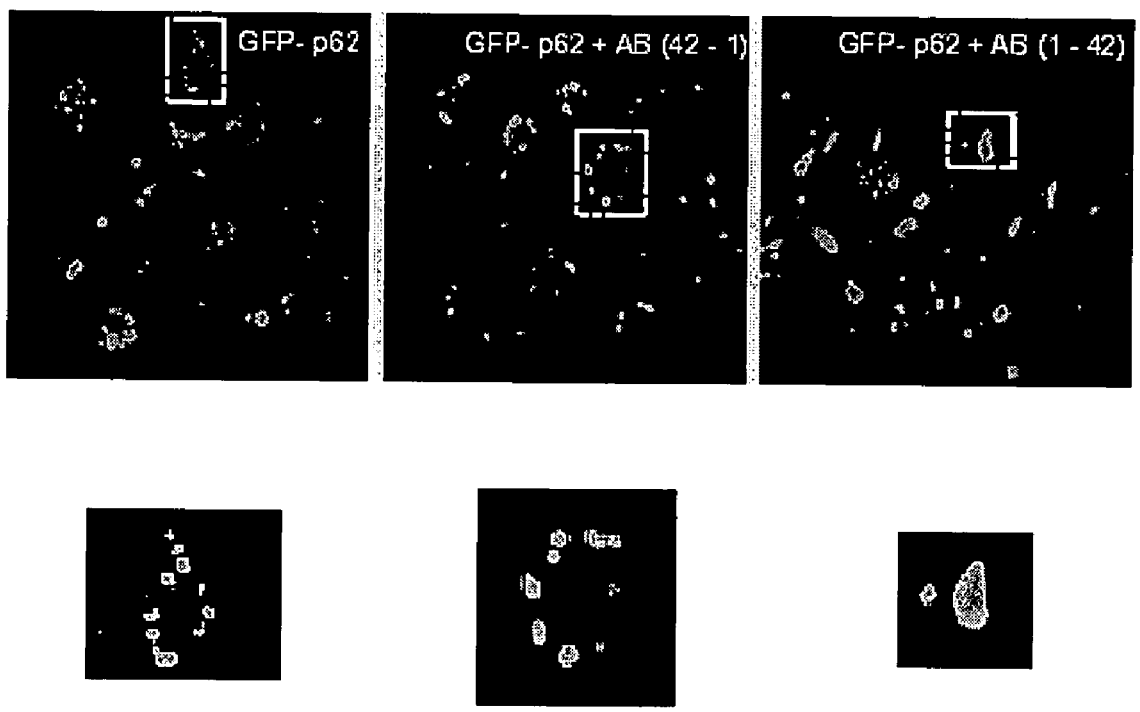
FIG. 9D shows a panel of immunofluorescence micrographs of cells incubated with or without $A\beta_{1-42}$ peptide.

To further determine if the coassociation of tau-p62-TRAF6 and UbcH7 could be recapitulated in vitro, a cotransfection approach was undertaken. Transfection of GFP-p62 along with HA-ubiquitin, Flag-TRAF6, His-tau and myc-UbcH7 followed by confocal immunofluorescent microscopy revealed that the proteins colocalize to discrete spherical aggregates (FIG. 9C). Inhibition of protein degradation by treatment with ALLN or MG132 (not shown) revealed that these aggregates increased in size, and the proteins retained their colocalized properties. Since the activity of the proteasome is decreased in AD and the neurotoxic peptide $A\beta_{1-42}$ has been shown to bind the proteasome and impair its activity, formation of p62-aggregates in vitro by Aβ peptide was determined (FIG. 9D). HEK cells were transfected with GFP-p62 followed by treatment or not with $A\beta_{1-42}$ and $A\beta_{42-1}$ peptides. The neurotoxic $A\beta_{1-42}$ peptide induced formation of p62 aggregates; whereas, the control peptide was without significant effect. Time-dependent analysis revealed that the small punctate aggregates appeared first, prior to formation of large fibrillar inclusions. This is consistent with the observation that microtubule dependent transport is important for the formation of p62 inclusions as assessed by treatment of the cells with nocodazole, a microtubule disrupting agent (9).

Moreover, these findings suggest that the smaller aggregates may be the precursors of large inclusions and reveal that a similar mechanism may account for aggregate formation during the course of AD.

Example 7

Tau is a K63-Polyubiquitinated Substrate of TRAF6 Interacting with the UBA Domain of p62

Figure 10A:
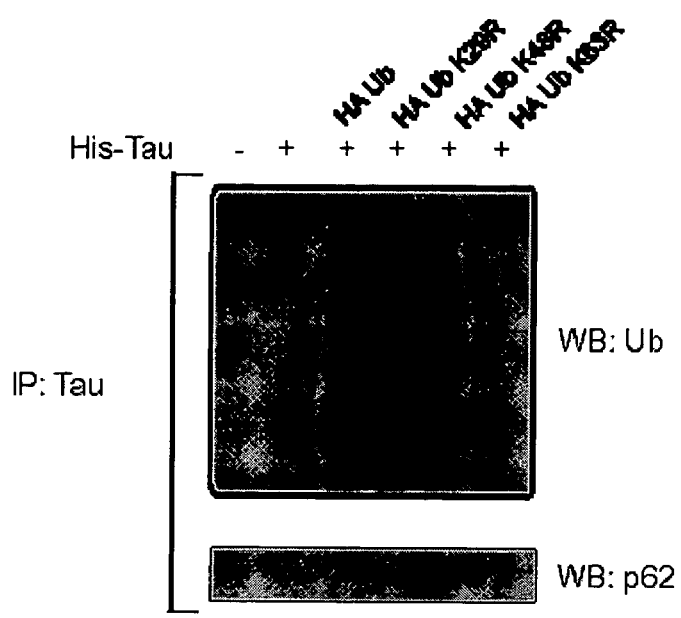
FIG. 10A shows immunoblots of tau antibody immunoprecipitates of lysates from HEK cells cotransfected either with HA-tagged wild-type Ub, K29R, K48R, or K63R point mutants of Ub along with WT-tau.
Figure 10B:
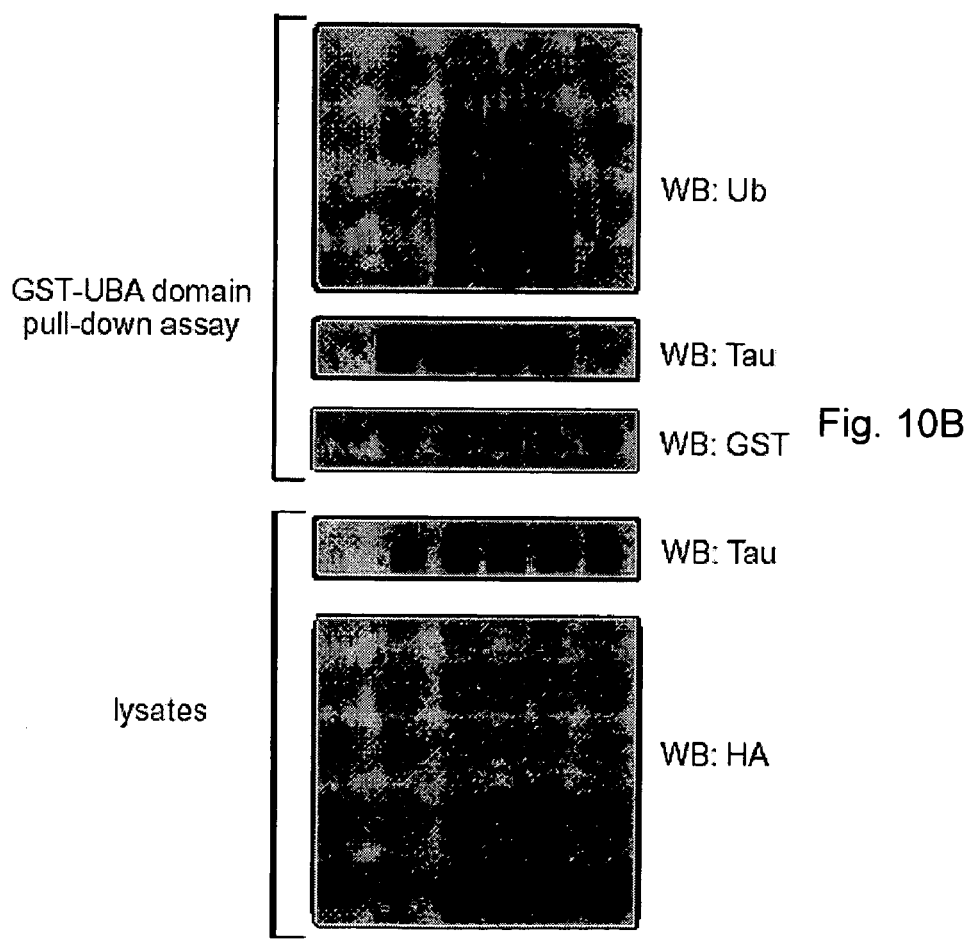
FIG. 10B shows a p62 GST-UBA domain pull-down assay from HEK cells cotransfected either with HA-tagged wild-type Ub, K29R, K48R, or K63R point mutants of Ub along with WT-tau.
Figure 10C:
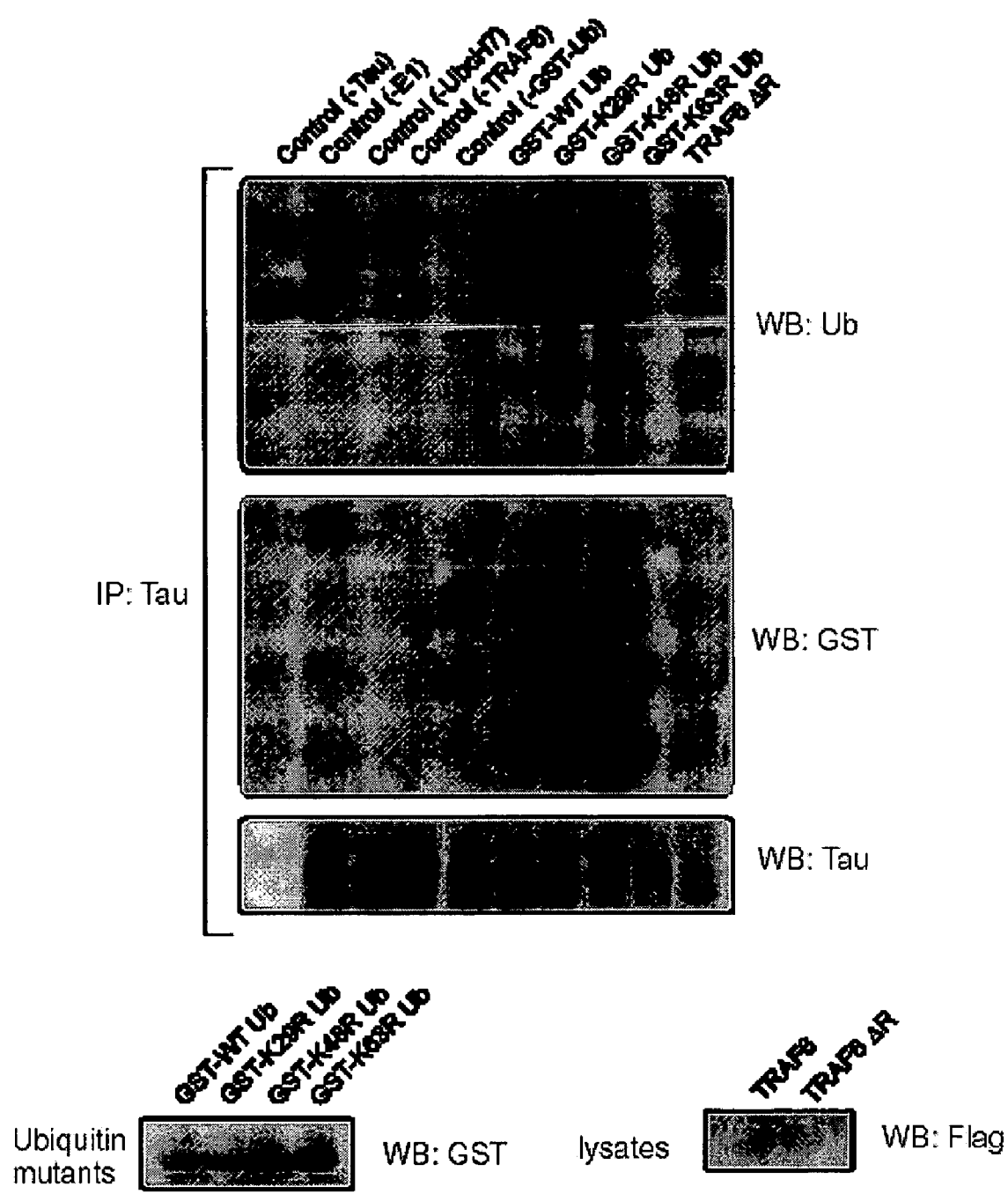
FIG. 10C shows an in vitro ubiquitination assay carried out in the presence or absence of E1, UbcH7 (E2), TRAF6 (E3) along with GST-tagged wild-type Ub or K29R, K48R, K63R point-mutants of Ub.
Figure 10D:
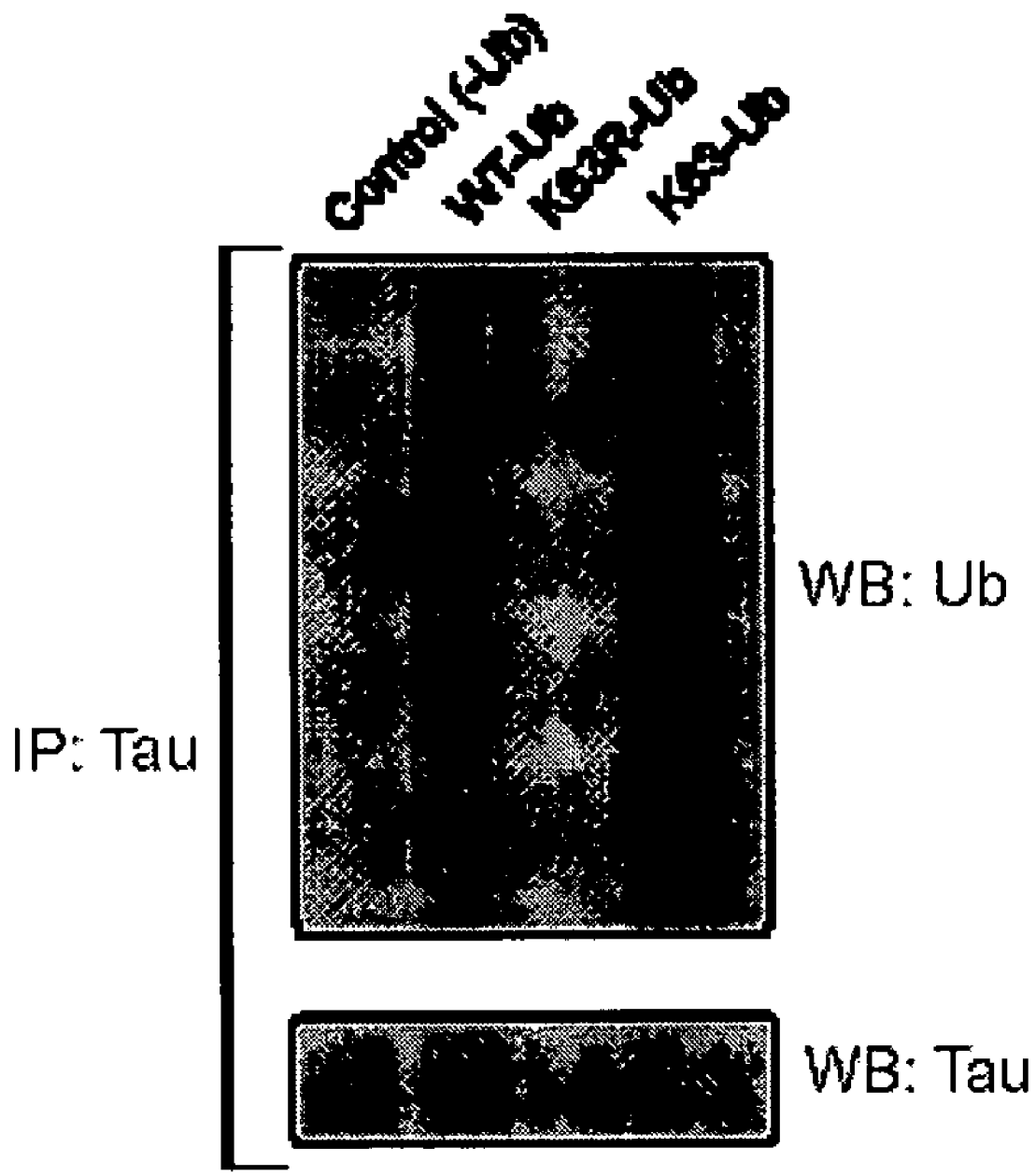
FIG. 10D shows an in vitro ubiquitination assay employing wild-type Ub, K63R Ub or only K63 linked Ub chains.

Because tau was ubiquitinated in samples recovered from AD brain, the type ubiquitin linked chains carried by tau in vitro were examined. HEK cells were transfected with His-tau along with wild-type and K/R mutants of ubiquitin at 29, 48 and 63. Tau was polyubiquitinated employing K63 polyubiquitin chains, since K63R mutant, completely abrogated polyubiquitination of tau (FIG. 10A). Additionally, impairment in the ubiquitination of tau, prevented its coassociation with p62. Lysates recovered from the transfected cells were employed in a GST-UBA pull down assay to determine if polyubiquitinated tau could interact with the UBA domain of p62. Indeed, polyubiquitinated tau effectively interacted with p62's UBA domain (FIG. 10B), and inhibition of ubiquitination prevented tau interaction with p62, thus confirming the coimmunoprecipitation results (FIG. 10A). Because TRAF6 exhibits E3-ubiquitin ligase activity, tau was immunoprecipitated from HEK cells and included it in an in vitro ubiquitination assay (FIG. 10C), along with TRAF6, UbcHT and various bacterially expressed GST ubiquitin constructs, wild type as well as K29R, K48R, and K63R mutants. When K63 was mutated to R, in vitro ubiquitination was completely abrogated (FIG. 10C). Alternatively, when tau was included in the ubiquitination assay along with wild type ubiquitin, or ubiquitin which can only generate K63 chains (FIG. 10D), polyubiquitin chain synthesis with tau as a substrate only took place with wild-type ubiquitin and K63 chains. Altogether, these results reveal that tau is K63 polyubiquitinated by the E2-UbcH7/E3-TRAF6 complex. Furthermore, coassociation of this E2/E3 pair could be detected in inclusions isolated from AD brain or recapitulated by cotransfection in HEK cells.

Example 8

Figure 11A:
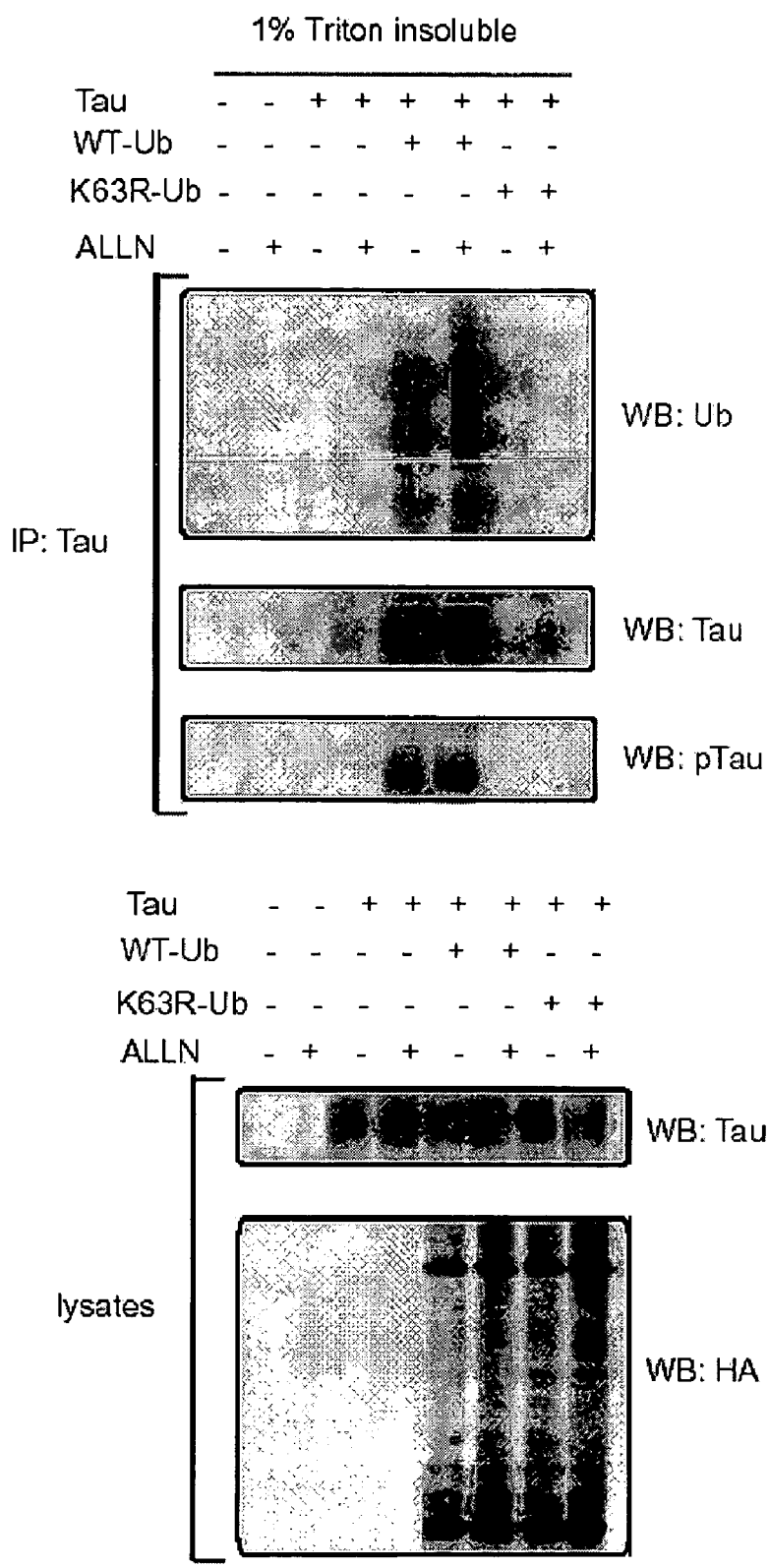
FIG. 11A shows immunoblots of cells transfected with WT-tau, along with WT-Ub or K63R ubiquitin mutant blotted for Ub, Tau, pTau, or HA.
Figure 11B:
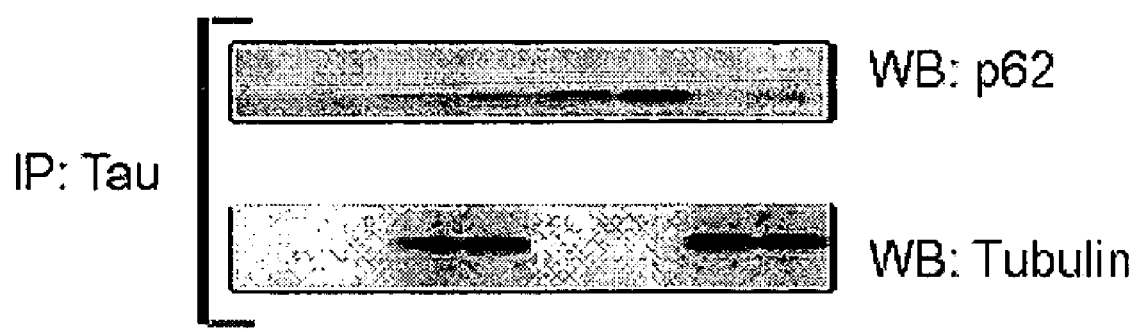
FIG. 11B shows immunoblots of cells transfected with WT-tau, along with WT-Ub or K63R ubiquitin mutant blotted for p62 and tubulin.

Polyubiquitinated Tau is Insoluble, Fails to Interact with Microtubules and is Cytotoxic To examine the effects of tau ubiquitination on its solubility properties, HEK cells were cotransfected with tau, ubiquitin or the K63R ubiquitin mutant, followed by treatment with ALLN or not (FIG. 11A). Cells were lysed and the triton soluble and insoluble fractions isolated. Tau was observed to be polyubiquitinated, sensitive to ALLN treatment and localized to the insoluble fraction. Expression of K63R mutant ubiquitin, prevented tau polyubiquitination and its association with the insoluble fraction. Interestingly, ubiquitinated tau was observed to be phosphorylated as well, whereas K63R prevented phosphorylation of tau. Sister cultures transfected in parallel were lysed and subjected to tau immunoprecipitation (FIG. 11B) followed by western blot analysis to both p62 and tubulin. Polyubiquitination of tau led to its association with p62, consistent with previous observations (FIG. 10A), with a concomitant decrease in tau's ability to interact with tubulin.

Example 9

Tau is Targeted for Degradation Through the Proteasome

Figure 12A:
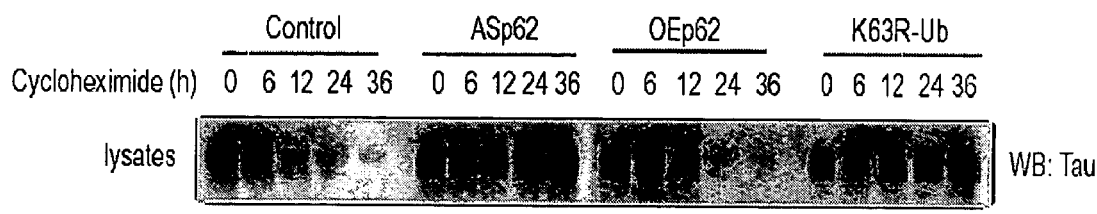
FIG. 12A shows immunoblots using HEK cells transfected with antisense (AS) p62, myc-p62 or K63R Ub mutant in addition to WT-tau and tau antibody.
Figure 12B:
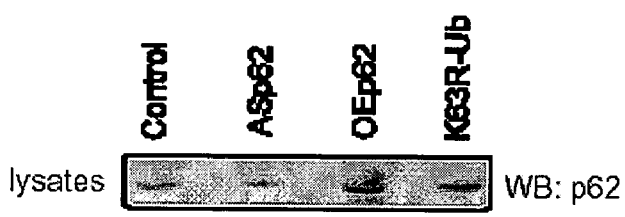
FIG. 12B shows a line graph quantifying the immunoblot of FIG. 6A.
Figure 12B:
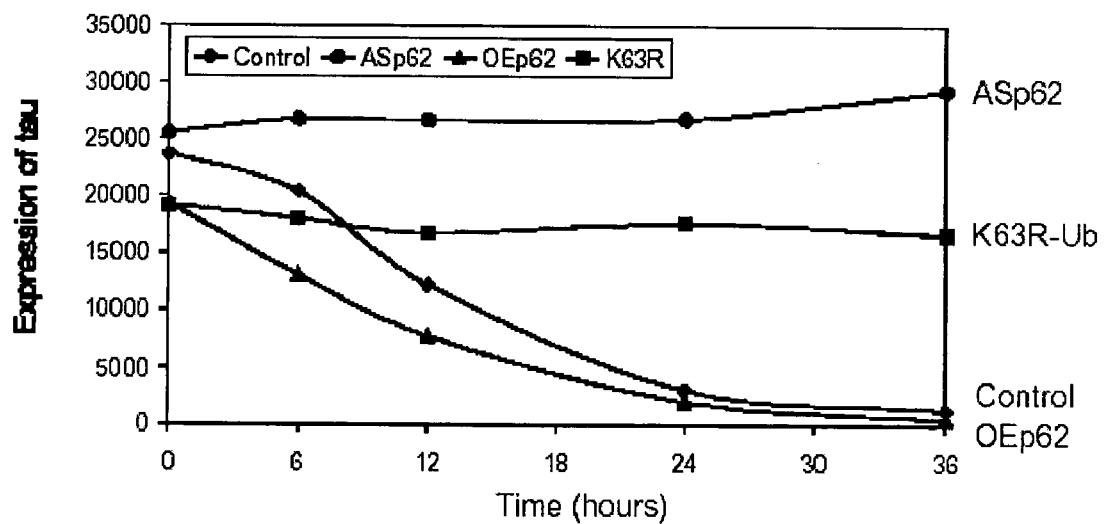
Figure 12C:
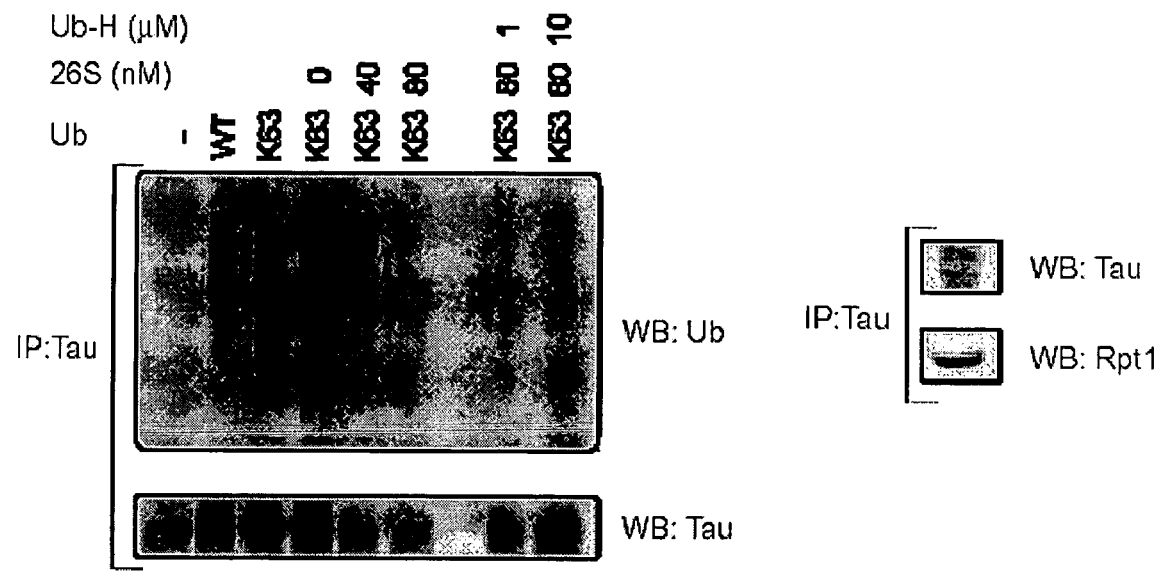
FIG. 12C shows an immunoblot of lysates from HEK 293 cells were transfected with WT-tau construct and blotted as indicated.
Figure 12D:
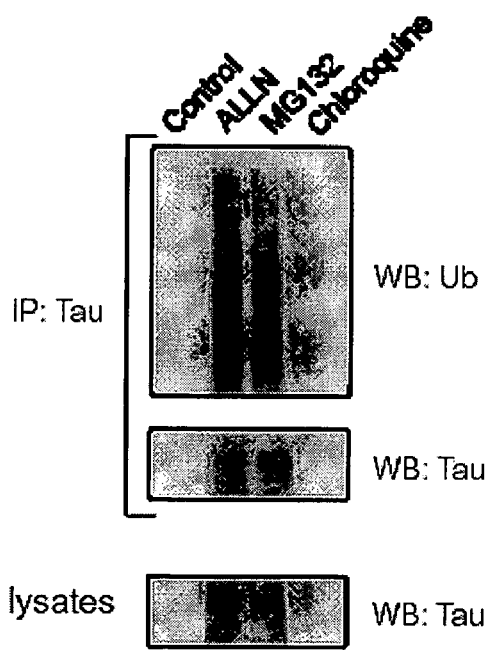
FIG. 12D shows immunoblots of HEK cells were transfected with WT-tau and treated with proteasomal inhibitors 50 μM of ALLN, 5 μM MG132 or 0.15 mM of lysosomal inhibitor chloroquine for 24 h at 37° C.

Depletion of p62 levels by transfection of antisense (AS) p62 retarded the turnover of p62 (FIG. 12A). By comparison p62 overexpression slightly enhanced the rate of turnover, whereas the K63R mutant ubiquitin also retarded the turnover of tau. Collectively these findings reveal that tau turnover is regulated by both the expression of p62 and the presence of K63 polyubiquitin chains carried by tau. The best known function of protein ubiquitination is to target proteins for degradation by the 26S proteasome. However, K63 chains have been hypothesized to play a role aside of targeting proteins to the proteasome. To test whether K63 chains are able to signal proteasomal degradation, tau was first ubiquitinylated in an in vitro reaction with K63 ubiquitin. The protein complex containing polyubiquitinated tau on beads was then incubated with 26S proteasome supplemented with $MgCl_2$ and ATP. The polyubiquitinated chains disappeared after incubation with purified 26S proteasome (FIG. 12B). To determine whether the observed disappearance of polyubiquitinated products is due to degradation or to the deubiquitinating activity in the 26S proteasome fraction, a deubiquitination inhibitor, Ub-H was added to the reaction. Polyubiquitin degradation was inhibited by the presence of Ub-H. These results confirm that K63 polyubiquitinated tau is deubiquitinated by the 26S proteasome. To test if ubiquitinated tau was targeted to the proteasome, HEK cells cotransfected with His-tau were treated with ALLN, MG132 or chloroquine. Both ALLN and MG132 block proteasome degradation, whereas chloroquine blocks degradation through the lysosome. It was observed that ubiquitinated tau accumulates in the presence of proteasome inhibitors, but not chloroquine, thus confirming that polyubiquitinated tau is degraded by the proteasome (FIG. 12C).

Example 10

Figure 13A:
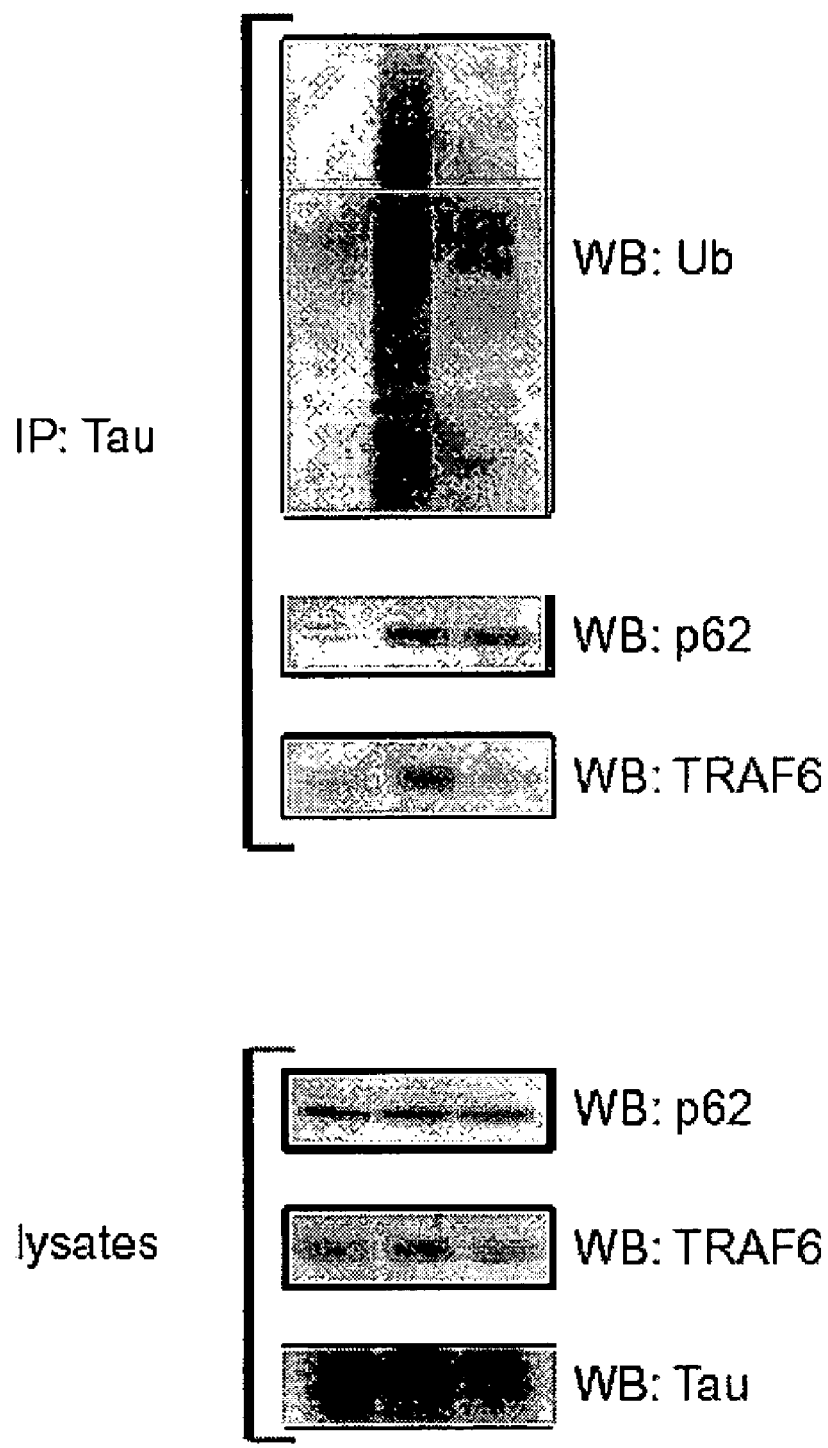
FIG. 13A shows immunoblots of PC 2 cells were treated with or without TRAF6 peptide.

Inhibition of TRAF6-p62 Interaction Prevents Tau Aggregation and Enhances Cell Survival Time/dose dependent studies revealed that tau polyubiquitination was maximum at 15 min treatment with NGF (50 ng/ml) (not shown). Peptide containing the TRAF6-binding motif (Pro-X-Glu-X-X) (SEQ ID NO. 7) has been shown to serve as a competitive inhibitor of TRAF6 signaling. The region spanning amino acids 225-251 is necessary for the interaction of p62 with TRAF6. The peptide containing TRAF6 binding motif in p62 along with the hydrophobic sequence containing the cell-permeable motif from Kaposi fibroblast growth factor sequence, AAVALLPAVLLALLAP-ESASGPSEDPSVNFLK (SEQ ID NO. 4) and control peptide AAVALLPAVLLALLAP-ESASGASADASVNFLK (SEQ ID NO. 5) was synthesized. As a preliminary step, PC12 cells were pretreated with various concentrations of peptide for 5 h, followed by NGF stimulation for 15 min and immunoprecipitation with TRAF6 and western blotted with p62. One hundred and fifty micromolar concentration of peptide was found to block TRAF6 interaction with p62 (not shown). The peptide was then tested for its ability to block NGF-induced tau polyubiquitination (FIG. 13A). Treatment with TRAF6 peptide, but not control (not shown), completely abrogated NGF-induced tau polyubiquitination and interaction of p62 with TRAF6.

Figure 13B:
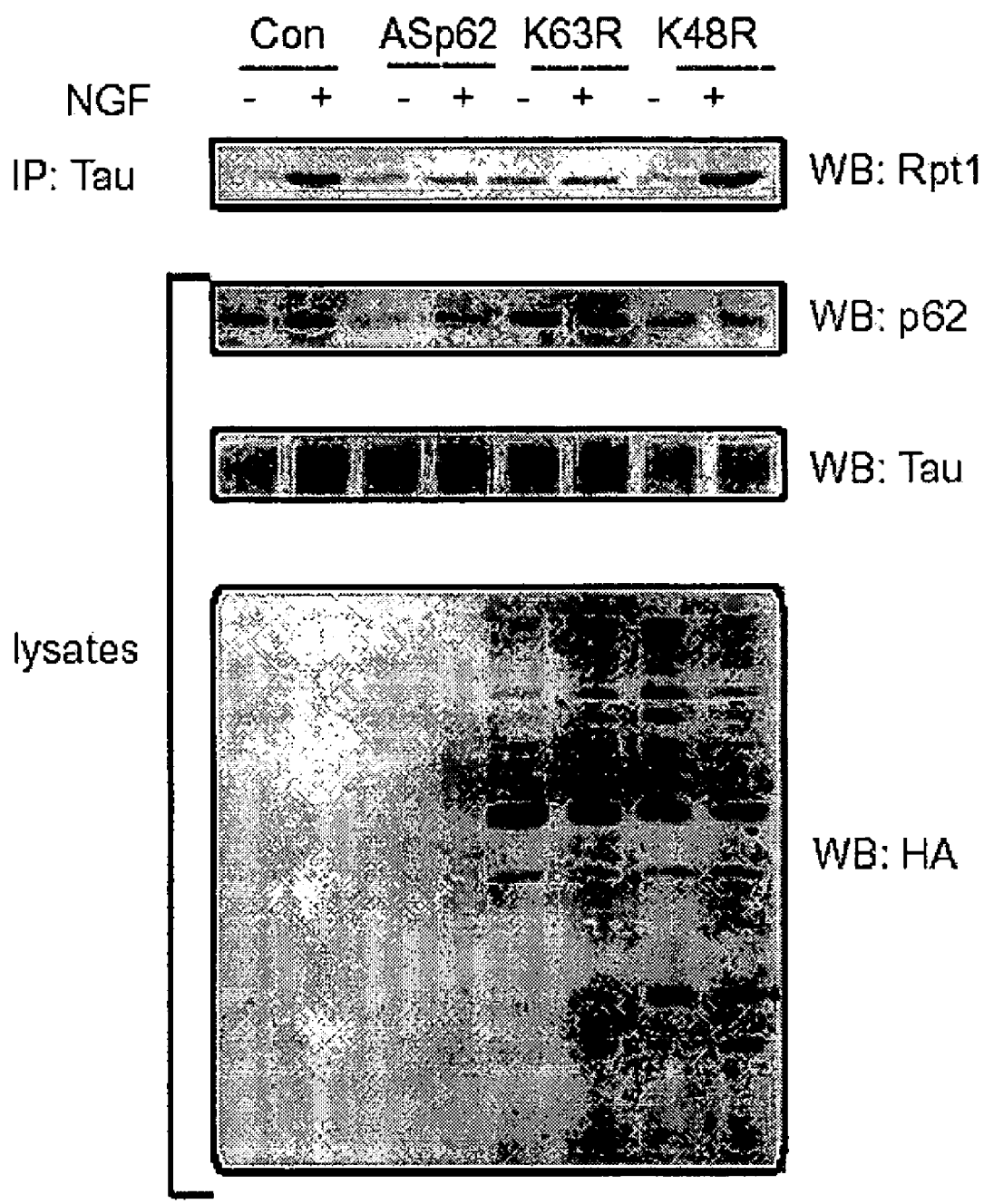
FIG. 13B shows immunoblots of PC12 cells were transfected with ASp62, HA-tag K63R or K48R mutant ubiquitin constructs blotted as indicated.

PC12 cells were first transfected with nothing, antisense (AS) p62, K63R or K48R ubiquitin mutants followed by NGF stimulation and immunoprecipitation of tau and western blot for Rpt1, an ATPase component of the 19S proteasome regulatory subunit. A robust interaction of tau with the proteasome upon NGF stimulation was observed; whereas, impaired tau polyubiquitination with K63R, but not K48R, prevented its interaction with the proteasome (FIG. 13B). Moreover, p62 was necessary for tau interaction with the proteasome. Collectively, these findings indicate that tau is targeted for degradation to the proteasome through K63 polyubiquitin chains, and p62 serves as a polyubiquitin binding protein involved in shuttling of tau for proteasomal degradation.

Example 11

Figure 14A:
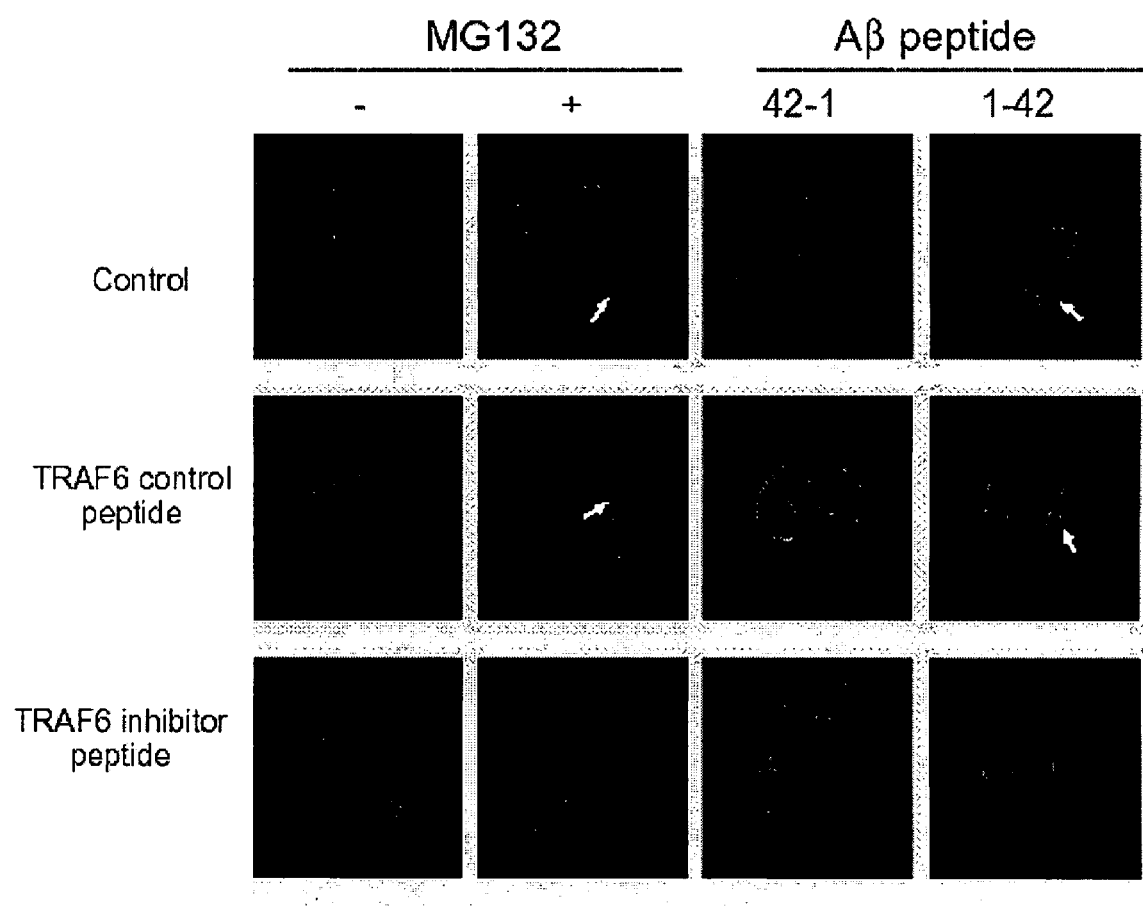
FIG. 14 is a diagram showing an exemplary tau ubiquitination pathway.
Figure 14B:
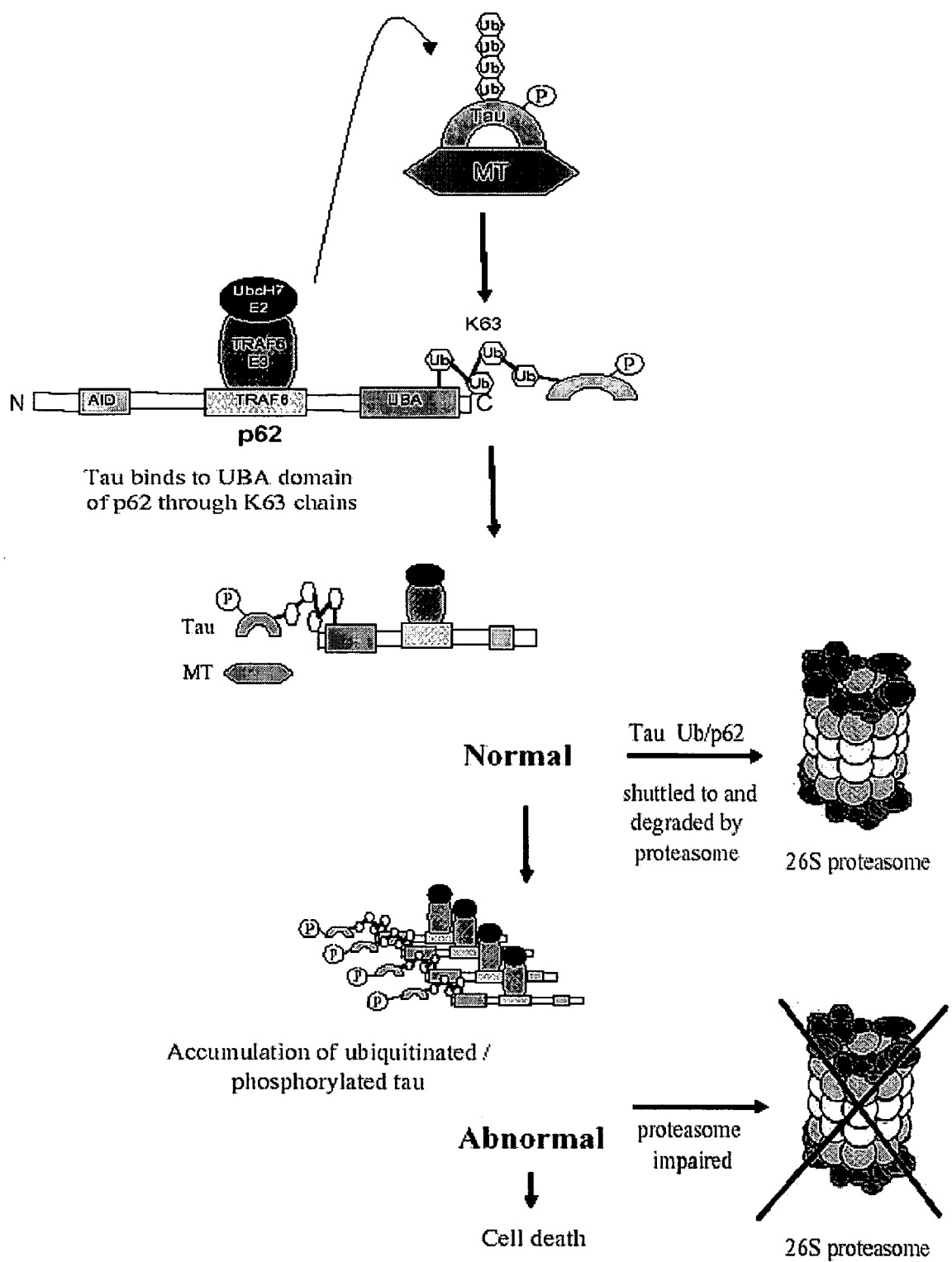

Inhibition of TRAF6-p62 Interaction/Tau Polyubiquitination Protects Cells from the Deleterious Effects of Tau Aggregate Accumulation PC12 cells were treated with NGF to induce tau polyubiquitination and treated or not with MG132 or Aβ and $A\beta_{1-42}$, $A\beta_{42-1}$. Only those cells treated with MG132 or $A\beta_{1-42}$, possessed large tau-ubiquitin aggregates (FIG. 14). The relationship between aggregate formation and cell death was assessed (Tables, 3 & 4). Tau aggregate formation was observed upon treatment with MG132 or $A\beta_{1-42}$ peptide. Treatment with TRAF6-p62 inhibitory peptide, which blocked tau ubiquitination (FIG. 13A), significantly reduced the formation of tau aggregates in cells treated with MG132 or $A\beta_{1-42}$, as compared to cells treated with TRAF6-control peptide (Table 3). Furthermore, aggregate formation correlated with enhanced cell survival (Table 4).

TABLE 3

Effects of proteasome inhibition and TRAF6 peptide on tail aggregate formation.

|  | −MG132 | +MG132 (25 μM) | Aβ42-1 (10 μM) | Aβ1-42 (10 μM) |
| --- | --- | --- | --- | --- |
| Control | 6% | 82% | 12% | 72% |
| TRAF6$^c$ (75 μM) | 4% | 78% | 16% | 80% |
| TRAF6$^I$ (75 μM) | 8% | 24% | 20% | 14% |

All cells were treated with NGF (50 ng/ml), followed by addition of control or inhibitory TRAF6 peptide +/−Aβ peptide. Cells were stained for tau and 300 cells from two independent experiments were scored for the presence of tau aggregates or not.

TABLE 4

Effects of proteasome inhibition and TRAF6 peptide on cell survival.

|  | −MG132 | +MG132 (25 μM) | Aβ42-1 (10 μM) | Aβ1-42 (10 μM) |
| --- | --- | --- | --- | --- |
| Control | 100% | 44.3% | 99.5% | 45.7% |
| TRAF6$^c$ (75 μM) | 98.4% | 44.9% | 98.2% | 46.0% |
| TRAF6$^I$ (75 μM) | 99.1% | 94.1% | 98.2% | 88.9% |

All cells were treated with NGF (50 ng/ml), followed by addition of control or inhibitory TRAF6 peptide +/−Aβ peptide. Survival was measured by MTS assay.

Example 12

Figure 15A:
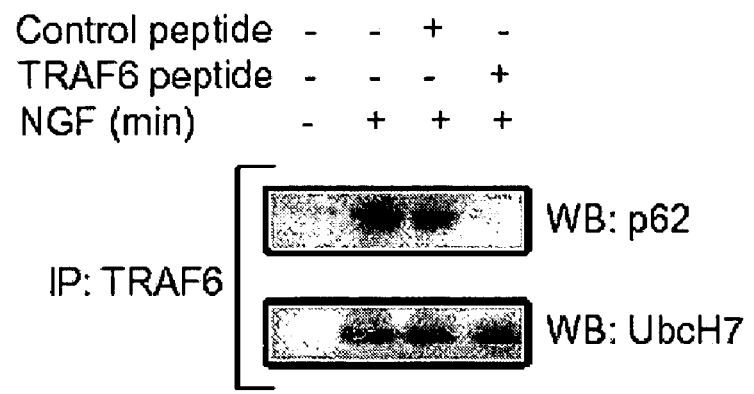
FIG. 15A shows immunoblots indicating TRAF6 peptide suppresses NGF-induced ubiquitination and internalization of TrkA.
Figure 15B:
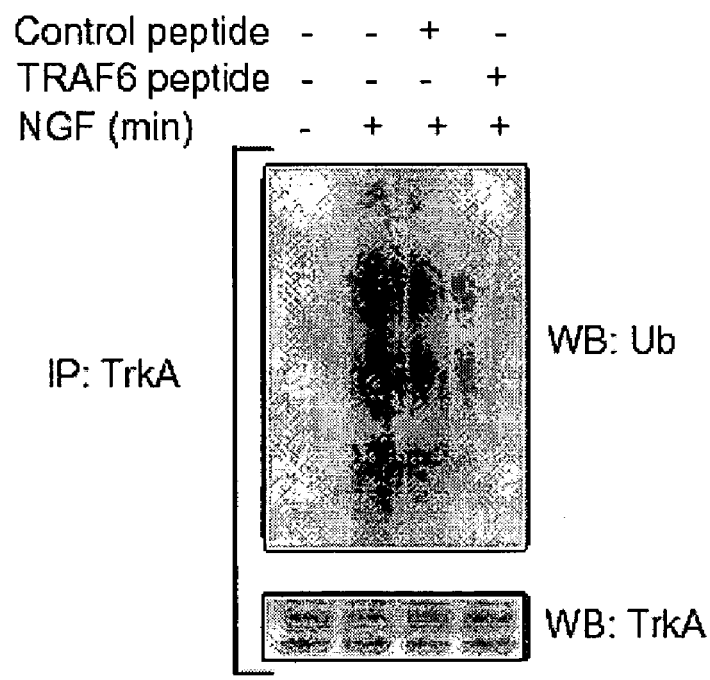
FIG. 15B shows immunoblots indicating the extent of ubiquitination of the indicated proteins in the presence of TRAF6 peptide.
Figure 15C:
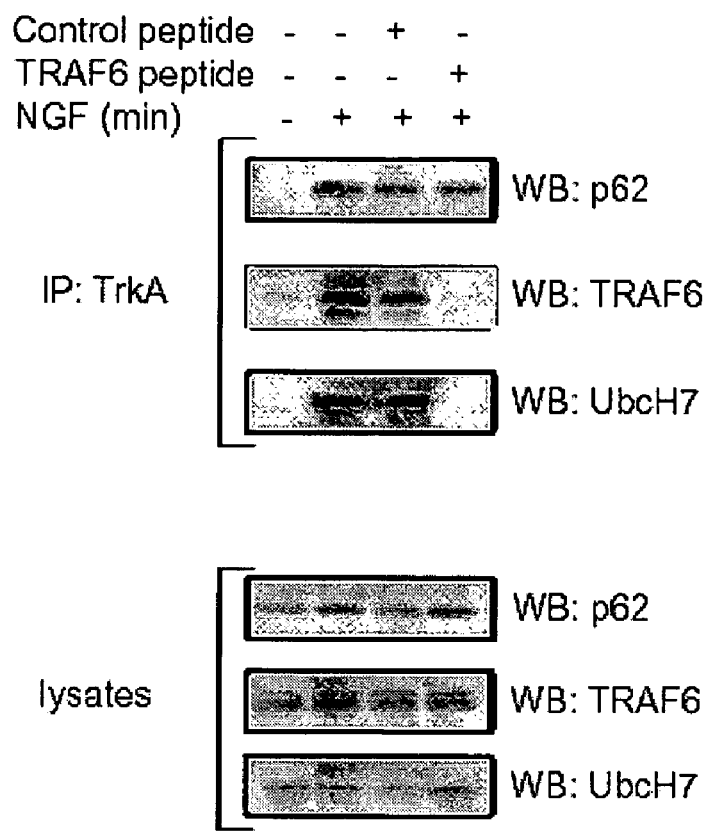
FIG. 15C shows immunoblots indicating the extent of interaction of the indicated proteins with TrkA in the presence of TRAF6 peptide.

TRAF6 Peptide Blocks TrkA Ubiquitination, Internalization and Differentiation The peptide containing the TRAF6-binding motif in p62 along with the hydrophobic sequence containing the cell-permeable motif from Kaposi fibroblast growth factor signal sequence AAVALLPAVLLALLAP-ESASG PSEDPSVNFLK (SEQ ID NO. 4) and control peptide AAVALLPAVLLALLAP-ESASGASADASVNFLK (SEQ ID NO. 5) was synthesized. As a preliminary step, PC12 cells were pretreated with different concentrations (75-300 µM) of TRAF6 peptide for 5 hours followed by NGF stimulation for 15 min and immunoprecipitation of TRAF6 followed by Western blotting for p62. 150 µM of TRAF6 peptide was found to be the optimum dose to block the interaction of p62 with TRAF6 (not shown). To address whether TRAF6 peptide affects the interaction of p62 and UbcH7 with TRAF6, PC12 cells were treated with or without 150 µM of control peptide or TRAF6 peptide for 5 hours and then stimulated with NGF for 15 min. By immunoprecipitating TRAF6, TRAF6 peptide (150 µM) abrogated the interaction of p62 with TRAF6, but not UbcH7, upon NGF treatment (FIG. 8A). Addition of control peptide was without effect. This finding suggests that TRAF6 peptide competes with TRAF6 to bind p62 and hence can be used as an inhibitor of TRAF6 signaling. The ability of the TRAF6 peptide to impair the ubiquitination process was investigated. Lysates recovered from NGF treated cells were immunoprecipitated with TrkA receptor antibody and blotted for ubiquitin or the receptor (FIG. 15B). Remarkably, the TRAF6 peptide was able to effectively abolish NGF-dependent ubiquitination of TrkA, whereas the control peptide has no effect. Interestingly, this finding confirms that TRAF6 ubiquitinates TrkA in vivo and suggests that the activity of TRAF6 is regulated by its interaction with p62. The ability of the peptide to interrupt the formation of the functional TrkA-p62-TRAF6-UbcH7 complex on NGF stimulation as well was also investigated. TrkA was immunoprecipitated and blotted for the presence of each protein in the complex (FIG. 15C). The TRAF6 peptide did not disrupt the interaction of p62 and TrkA, but eliminated TRAF6 and UbcH7 from interacting with TrkA. This result further confirms the specificity of the peptide as an inhibitor of TRAF6 signaling.

Figure 15D:
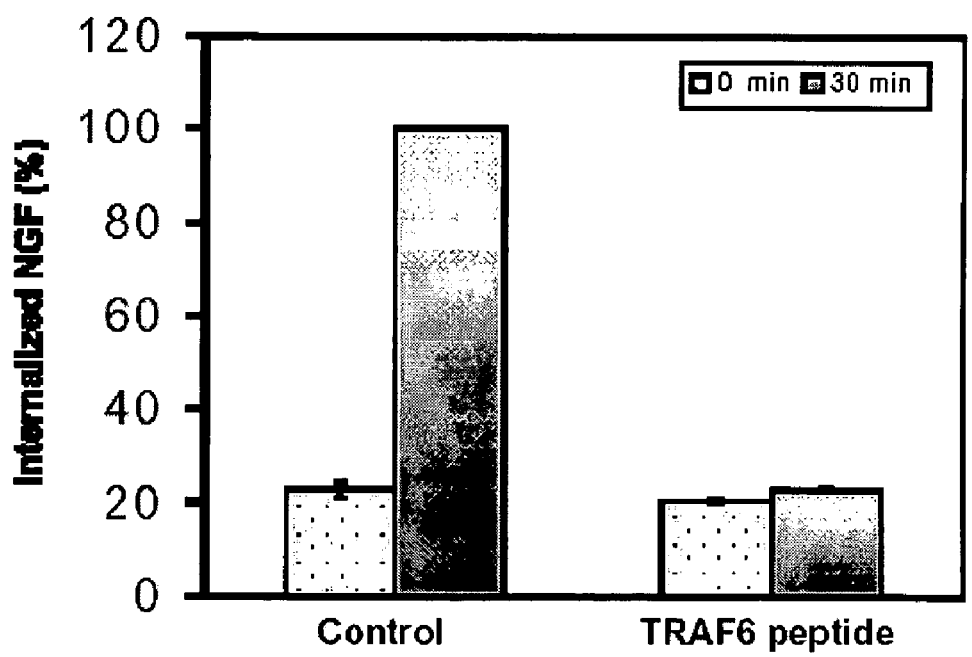
FIG. 15D shows a bar graph of the internalization of NGF by PC 2 cells pretreated with TRAF6 peptide (150 μM) for 5 h at 37° C.
Figure 15E:
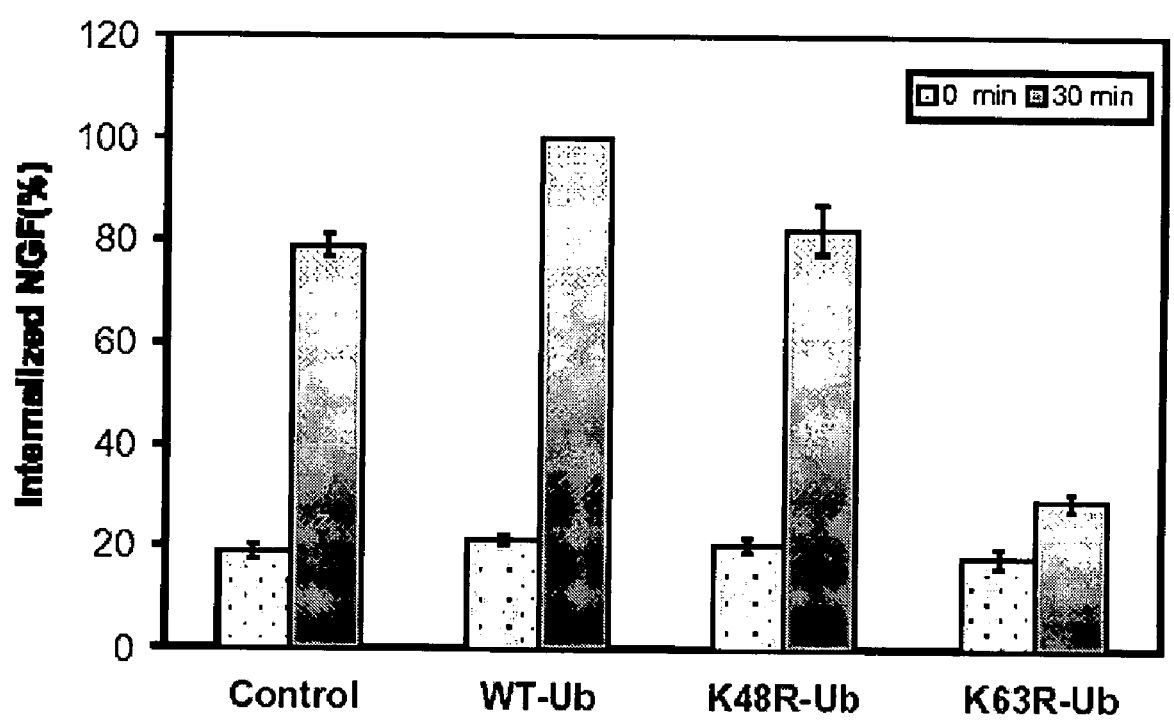
FIG. 15E shows a bar graph of the internalization of NGF by PC 2 cells transfected with exogenous HA-tag wild type ubiquitin, K48R or K63R mutants of ubiquitin.

Additionally, PC12 cells were pretreated or not with TRAF6 peptide (150 µM) followed by measurement of internalized receptor employing 125I-NGF binding assay (FIG. 15D). TRAF6 peptide, but not the control peptide, significantly blocked the internalization of NGF (not shown), concomitant with an absence in ubiquitination (FIG. 15B). Similarly, the level of internalized NGF was measured in PC12 cells transfected with wild-type ubiquitin, K48R or K63R ubiquitin mutants (FIG. 15E). Transfection of ubiquitin, or K48R mutant was without any effect on internalization of NGF. By comparison, transfection of K63R ubiquitin mutant totally abrogated internalization of the ligand. This result is consistent with K63-polyubiquitination of TrkA, a requirement for the UBA domain of p62 in regulating internalization of TrkA, and p62's ability to recognize K63-polyubiquitinated substrates (Seibenhener et al, 2004). Collectively, these findings reveal that TrkA is a bonafide substrate of TRAF6, possessing K63 polyubiquitin chains. Thus, p62 serves as an adaptor, as well as, a scaffold for TRAF6-directed ubiquitination and K63 chains play a signaling role for internalization and sorting of the receptor.

---

I claim:

1. A method for identifying a modulator of intracellular aggregate formation comprising:
   (a) determining binding of TRAF6 to p62 or a fragment thereof comprising amino acids 225-251 of SEQ ID NO: 1 in the presence of a test compound;
   (b) selecting the test compound that reduces or inhibits TRAF6 binding to p62 and reduces or inhibits intracellular aggregate formation.

2. The method of claim 1, wherein a cell expressing TRAF6 and p62 or fragment thereof is contacted with the test compound to determine binding of TRAF6 to p62 or the fragment thereof.

3. The method of claim 2, wherein the determination of binding is based on in vitro or in vivo data.

4. A method for identifying an inhibitor of intracellular aggregate formation comprising:
   (a) contacting a cell expressing TRAF6 and p62 or a fragment thereof comprising amino acids 225-251 of SEQ ID NO: 1 with a test compound;
   (b) contacting the cell with an aggregate inducing agent; and
   (c) selecting the test compound that reduces or inhibits the association of TRAF6 with p62 or the fragment thereof and reduces or inhibits aggregate formation.

5. The method of claim 4, wherein the cell is a neural cell.

6. The method of claim 4, wherein the aggregate formation comprises a K63 polyubiquinated substrate or a fragment thereof.

7. The method of claim 4, wherein the method is automated for a high through-put assay.

8. The method of claim 4, wherein the aggregate inducing agent comprises N-acetyl-Leu-Leu-norleucine-al.

9. A method for identifying an inhibitor of intracellular aggregate formation comprising:
   (a) contacting a cell engineered to express a GFP-p62 fusion protein with a test compound in the presence of an intracellular aggregate inducing agent;
   (b) detecting the formation of intracellular aggregates comprising GFP-p62 in the contacted cells;
   (c) selecting a test compound that
      (i) reduces or inhibits formation of intracellular aggregates comprising GFP-p62 fusion protein compared to intracellular aggregates comprising GFP-p62 fusion protein formed in the absence of the test compound, and
      (ii) reduces or inhibits TRAF6 binding to p62.

10. The method of claim 9, wherein the intracellular aggregate inducing agent comprises N-acetyl-Leu-Leu-norleucine-al.

11. The method of claim 9, wherein the intracellular aggregates comprise a K63 polyubiquinated substrate.

* * * * *